US007935532B2

(12) United States Patent
Azpiroz et al.

(10) Patent No.: US 7,935,532 B2
(45) Date of Patent: *May 3, 2011

(54) DWF4 POLYNUCLEOTIDES, POLYPEPTIDES AND USES THEREOF

(75) Inventors: Ricardo Azpiroz, Dallas, TX (US); Sunghwa Choe, Seoul (SK); Kenneth Feldmann, Newbury Park, CA (US)

(73) Assignee: Arizona Board of Regents for and on behalf of Arizona State University, Tucson, AZ (US)

( * ) Notice: Subject to any disclaimer, the term of this patent is extended or adjusted under 35 U.S.C. 154(b) by 65 days.

This patent is subject to a terminal disclaimer.

(21) Appl. No.: 12/388,110

(22) Filed: Feb. 18, 2009

(65) Prior Publication Data
US 2010/0205694 A1 Aug. 12, 2010

Related U.S. Application Data

(60) Continuation of application No. 11/333,636, filed on Jan. 17, 2006, now Pat. No. 7,589,255, which is a continuation of application No. 10/804,772, filed on Mar. 18, 2004, now Pat. No. 7,253,336, which is a division of application No. 09/502,426, filed on Feb. 11, 2000, now Pat. No. 6,987,025.

(60) Provisional application No. 60/119,657, filed on Feb. 11, 1999, provisional application No. 60/119,658, filed on Feb. 11, 1999.

(51) Int. Cl.
*A01H 5/00* (2006.01)
*C12N 5/10* (2006.01)
*C12N 15/82* (2006.01)

(52) U.S. Cl. ......... 435/468; 435/419; 800/287; 800/290

(58) Field of Classification Search .................. None
See application file for complete search history.

(56) References Cited

U.S. PATENT DOCUMENTS

| 5,204,253 | A | 4/1993 | Sanford et al. |
| 5,538,880 | A | 7/1996 | Lundquist et al. |
| 5,591,616 | A | 1/1997 | Hiei et al. |
| 5,859,326 | A | 1/1999 | An |
| 5,952,545 | A | 9/1999 | Koncz et al. |
| 6,329,571 | B1 | 12/2001 | Hiei |
| 6,545,200 | B1 | 4/2003 | Cahoon et al. |
| 6,987,025 | B1 | 1/2006 | Azpiroz et al. |
| 2006/0041952 | A1 | 2/2006 | Cook et al. |
| 2006/0057724 | A1 | 3/2006 | Alexandrov et al. |
| 2006/0150283 | A1 | 7/2006 | Alexandrov et al. |

FOREIGN PATENT DOCUMENTS

| WO | WO 97/35986 | 10/1997 |
| WO | WO 99/32619 | 7/1999 |
| WO | WO 99/53050 | 10/1999 |
| WO | WO 00/47715 | 8/2000 |
| WO | WO 01/75164 | 10/2001 |
| WO | WO 02/46449 | 6/2002 |

OTHER PUBLICATIONS

U.S. Appl. No. 10/957,569, filed Nov. 3, 2005, Zhihong et al.
U.S. Appl. No. 60/505,689, filed Sep. 23, 2003, Zhihong et al.
U.S. Appl. No. 60/544,771, filed Feb. 13, 2004, Zhihong et al.
U.S. Appl. No. 60/558,869, filed Apr. 1, 2004, Zhihong et al.
U.S. Appl. No. 60/583,691, filed Jun. 30, 2004, Alexandrov et al.
U.S. Appl. No. 60/637,140, filed Dec. 16, 2004, Feldmann et al.
U.S. Appl. No. 60/518,075, filed Nov. 6, 2003, Pennell et al.
Akama et al., "Efficient Transformation of *Arabidopsis thaliana*: Comparison of the Efficiences With Various Organs, Plant Ecotypes and Agrobacterium Strains," *Plant Cell Rep.*, 1997, 12:7-11.
Azpiroz et al., "An *Arabidopsis* Brassinosteroid-Dependent Mutant is Blocked in Cell Elongation," *Plant Cell*, 1998, 10:219-230.
Barendse et al., "The role of Endogenous Gibberellins During Fruit and Seed Development: Studies on Gibberellin-Deficient Genotypes of *Arabidopsis thaliana*," *Physiol. Plant*, 1986, 67:315-319.
Bishop et al., "The Tomato *Dwarf* Gene Isolated by Heterologous Transposon Tagging Encodes the First Member of a New Cytochrome P450 Family," *Plant Cell*, 1996, 8:959-969.
Branch, "A good antisense molecule is hard to find," *TIB*, 23:45-50, (1998).
Choe et al., "*Arabidopsis* dwarf mutants define eight genes involved in brassinosteroid biosynthesis and signal transduction," *Plant Biology*, 1998, p. 10, Annual Meeting of the American Society of Plant Physiologists, Madison, WI, Jun. 27-Jul. 1, 1998.
Choe et al., "*Arabidopsis* dwarf mutants define the genes involved in brassinosteroid biosynthesis," *Plant Biology*, 1998, p. 133, Annual Meeting of the American Society of Plant Physiologists, Madison, WI, Jun. 27-Jul. 1, 1998.
Choe et al., "The *Arabidopsis dwarf1* Mutant is Defective in the Conversion of 24-Methylenecholesterol to Campesterol in Brassinosteroid Biosynthesis," *Plant Physiol.*, 1999, 119:897-907.
Choe et al., "Overexpression of *DWARF4* in the brassinosteroid biosynthetic pathway results in increased vegetative growth and seed yield in *Arabidopsis*," *The Plant Journal*, 2001, 26(6):573-582.
Choe et al., "The *DWF4* Gene of *Arabidopsis* Encodes a Cytochrome P450 That Mediates Multiple $22_\alpha$-Hydroxylation Steps in Brassinosteroid Biosynthesis," *The Plant Cell*, 1998, 10(2):231-244.
Choi et al., "An Alternative Brassinolide Biosynthetic Pathway Via Late C-6 Oxidation," *Phytochemistry*, 1997, 44(4):609-613.
Chory et al., "A Role for Cytokinins in De-Etiolation in *Arabidopsis*," *Plant Physiol.*, 1994, 104:339-347.
Chory et al., "*Arabidopsis thaliana* Mutant That Develops as a Light-Grown Plant in the Absence of Light," *Cell*, 1989, 58:991-999.
Clouse et al., "A Brassinosteroid-Insensitive Mutant in *Arabidopsis thaliana* Exhibits Multiple Defects in Growth and Development," *Plant Physiol.*, 1996, 111:671-678.

(Continued)

*Primary Examiner* — Ashwin Mehta
(74) *Attorney, Agent, or Firm* — Fish & Richardson P.C.

(57) ABSTRACT

The present invention relates to novel, polynucleotides isolated from dwarf plants. The dwf4 polynucleotides that encode all, or a portion of, a DWF4 polypeptide, a cytochrome P450 enzyme that mediates multiple steps in synthesis of brassinosteriods. The present invention also relates to isolated polynucleotides that encode regulatory regions of dwf4. Uses of the dwf4 polypeptides and polynucleotides are also disclosed.

16 Claims, 25 Drawing Sheets

OTHER PUBLICATIONS

Deng, "Fresh View of Light Signal Transduction in Plants," *Cell*, 1994, 76:423-426.

Deng and Quail, "Genetic and Phenotype Characterization of *cop* 1 Mutants of *Arabidopsis thaliana*," *The Plant Journal*, 1992, 2(1):83-95.

Feldmann, "Cytochrome P450s as genes for crop improvement," *Current Opinion in Plant Biology*, 2001, 4:162-167.

Feldmann et al., "A Dwarf Mutant of *Arabidopsis* Generated by T-DNA Insertion Mutagenesis," *Science*, 1989, 243:1351-1354.

Fujioka et al., "The *Arabidopsis deetiolated2* Mutant is Blocked Early in Brassinosteroid Biosynthesis," *Plant Cell*, 1997, 9:1951-1962.

Fujioka et al., "Identification of Castasterone, 6-Deoxocastasterone, Typhasterol and 6-Deoxotyphasterol from the Shoots of *Arabidopsis thaliana*," *Plant Cell Physiol.*, 1996, 37(8):1201-1203.

Fujioka and Sakurai, "Brassinosteroids," *Nat. Prod. Rep.*, 1997a, 14:1-10.

Fujioka and Sakurai, "Biosynthesis and Metabolism of Brassinosteroids," *Physiologia Plantarum*, 1997b, 100:710-715

Gachotte et al., "An *Arabidopsis* mutant deficient in sterol biosynthesis: heterologous complementation by *ERG* 3 encoding a $\Delta^7$-sterol-C-5-desaturase from yeast," *The Plant Journal*, 1995, 8(3):407-416.

Grove et al., "Brassinolide, a Plant Growth-Promoting Steroid Isolated From *Brassica napus* Pollen," *Nature*, 1979, 281:216-217.

Hou et al., "A New Class of *Arabidopsis* Constitutive Photomorphogenic Genes Involved in Regulating Cotyledon Development," *Plant Cell*, 1993, 5:329-339.

Kauschmann et al., "Genetic Evidence for an Essential Role of Brassinosteroids in Plant Development," *Plant Journal*, 1996, 9:701-713.

Kim et al., "A 20 nucleotide upstream element is essential for the nopaline synthase (nos) promoter activity," *Plant Molecular Biology*, 24:105-117, (1994).

Koornneef et al., "A Gibberellin Insensitive Mutant of *Arabidopsis thaliana*," *Physiol. Plant*, 1985, 65:33-39.

Koornneef and Van der Veen, "Induction and Analysis of Gibberellin Sensitive Mutants in *Arabidopsis thaliana* (L.) Heynh," *Theor. Appl. Genet.*, 1980, 58:257-263.

Li et al., "A Role for Brassinosteroids in Light-Dependent Development of *Arabidopsis*," *Science*, 1996, 272:398-401.

Li et al., "Conservation Function Between Mammalian and Plant Steroid 5α-Reductases," *Proc. Natl. Acad. Sci.* USA, 1997, 94:3554-3559.

Li and Chory, "A Putative Leucine-Rich Repeat Receptor Kinase Involved in Brassinosteroid Signal Transduction," *Cell*, 1997, 90:929-938.

Mandava, "Plant Growth-Promoting Brassinosteroids," *Annu. Rev. Plant Physiol. Plant Mol. Biol.*, 1988, 39:23-52.

Mitchell et al., "Brassins—a New Family of Plant Hormones from Rape Pollen," *Nature*, 1970, 225:1065-1066.

Mushegian and Koonin, "A Putative FAD-Binding Domain in a Distinct Group of Oxidases Including a Protein Involved in Plant Development," *Protein Science*, 1995, 4:1243-1244.

Nebert et al., "P450 Gene Nomenclature Based on Evolution," *Methods Enzymol.*, 1991, 206:3-11.

Nebert et al., "The P450 Superfamily: Update on New Sequences, Gene Mapping, and Recommended Nomenclature," *DNA and Cell Biology*, 1991, 10(1):1-14.

Nebert et al., "CORRIGENDUM The P450 Superfamily: Update on New Sequences, Gene Mapping, and Recommended Nomenclature," *DNA and Cell Biology*, 1991, 10(5):397-398.

Nelson et al., "P450 superfamily: update on new sequences, gene mapping, accession numbers and nomenclature," *Pharmacogenetics*, 1996, 6:1-42.

Noguchi et al., "Biosynthetic Pathways of Brassinolide in *Arabidopsis*," *Plant Physiology*, 2000, 124:201-209.

Nomura et al., "Blockage of Brassinosteroid Biosynthesis and Sensitivity Causes Dwarfism in Garden Pea," *Plant Physiol.*, 1997, 113:31-37.

Paquette, et al., "Intron-Exon Organization and Phylogeny in a Large Superfamily, the Paralogous Cytochrome P450 Genes of *Arabidopsis thaliana*", *DNA and Cell Biology*, Nov. 5, 2000, 19:307-317.

Rees, "Biosynthesis of Ecdysone," *Comprehensive Insect Physiology, Biochemistry and Pharmacology*, 1985, Kerkut and Gilbert (eds. ), Oxford, Pergamon Press, pp. 249-293.

Sakurai and Fujioka, "Studies on Biosynthesis of Brassinosteroids, "*Biosci. Biotechnol. Biochem.*, 1997, 61:757-762.

Schuler et al., "Functional Genomics of P450s", *Annu. Rev. Plant Biol.*, 2003, 54:629-667.

Stam et al,. "The Silence of Genes in Transgenic Plants," *Annals of Botany*, 79:3-12, (1997).

Szekeres et al., "Brassinosteroids Rescue the Deficiency of CYP90, a Cytochrome P450, Controlling Cell Elongation and De-etiolation in *Arabidopsis*," *Cell*, 1996, 85:171-182.

Takahashi et al., "The Diminuto Gene of *Arabidopsis* is Involved in Regulating Cell Elongation," *Genes & Development*, 1995, 9:97-107.

Talon et al., "Endogenous Gibberellins in *Arabidopsis thaliana* and Possible Steps Blocked in the Biosynthetic Pathways of the Semidwarf *ga4* and *ga5* Mutants," *Proc. Natl. Acad. Sci.* USA, 1990, 87:7983-7987.

Timpte et al., "Effects of the *axr2* Mutation of *Arabidopsis* on Cell Shape in Hypocotyl and Inflorescence," *Planta*, 1992, 188:271-278.

Timpte et al., "The *axr2-1* Mutation of *Arabidopsis thaliana* is a Gain-of-Function Mutation that Disrupts an Early Step in Auxin Response," *Genetics*, 1994, 138:1239-1249.

Van der Krol et al., "Antisense genes in plants: an overview," *Gene*, 1988, 72:45-50.

Waycott et al., "Phenotypic Characterization of the *dwarf-4* Mutant of Lettuce," *Can. J. Bot.*, 1994, 72:1541-1549.

Wei et al., "*Arabidopsis COP8, COP10,* and *COP11* Genes are Involved in Repression of Photomorphogenic Development in Darkness," *Plant Cell*, 1994, 6:629-643.

Wei and Deng, "*COP9*: A New Genetic Locus Involved in Light-Regulated Development and Gene Expression in *Arabidopsis*," *Plant Cell*, 1992, 4:1507-1518.

Yokata, "The Structure, Biosynthesis and Function of Brassinosteroids," Trends Plant Sci., 1997, 2(4):137-143.

GenBank Accession No. AF044216, Mar. 1998.
GenBank Accession No. X87368, Oct. 1996.
GenBank Accession No. U54770, Oct. 1996.
GenBank Accession No. M13785, Apr. 1993.
GenBank Accession No. D64003, Oct. 1997.
GenBank Accession No. U32579, Sep. 1996.
GenBank Accession No. U68234, Nov. 1996.
GenBank Accession No. X70981, Jan. 1994.
GenBank Accession No. P48421, Oct. 2000.
GenBank Accession No. AL049659, Apr. 2000.
GenBank Accession No. P48418, Dec. 1998.
GenBank Accession No. X71658, Nov. 1993.
GenBank Accession No. AC104473, dated Oct. 30, 2002.

Adams et al. "Parent-of-origin effects on seed development in *Arabidopsis thaliana* require DNA methylation" *Development*, 2000, 127:2493-2502.

Armaleo et al., "Biolistic nuclear transformation of *Saccharomyces cervisiae* and other fungi" *Current Genetics*, 1990 17:97-103.

Asami et al. "Selective interaction of triazole derivative with DWF4, a cytochrome P450 monooxygenase of the brassinosteriod biosynthetic pathway, corresponses with brassinosteroid deficiently in plant" *The Journal of Biological Chemistry*, Jul. 13, 2001, 276(26):25687-25691.

Bateman et al., "Pfam 3.1: 1313 multiple alignments and profile HMMS match the majority of proteins" *Nucl. Acids Res.*, 1999, 27:260-262.

Bishop and Koncz, "Brassinosteroids and Plant Steroid Hormone Signaling," *The Plant Cell*, 2002, pp. S97-S110.

Bonner et al. "Reduction in the rate of DNA reassociation by sequence divergence" *J. Mol. Biol.*, 1973, 81:123.

Busk, "Regulatory elements in vivo in the promoter of the abscisic acid responsive gene rab17 from maize" *Plant J.*, 1997, 11:1285-1295.

Dhaubhadel et al., "Brassinosteroid functions to protect the translational machinery and heat-shock protein synthesis following thermal stress," *The Plant Journal*, 2002, 29(6):681-691.

Escudero et al., "T-DNA transfer in meristematic cells of maize provided with intracellular *Agrobacterium*" *The Plant Journal*, 1996, 10(2):355-360.

Guatelli et al., "Isothermal, in vitro amplification of nucleic acids by a multienzyme reation modeled after retroviral replication" *Proc. Natl. Acad. Sci. USA*, 1990, 87:1874-1878.

He et al., "BZR1 is a transcriptional repressor with dual roles in brassinosteroid homeostasis and growth responses," *Science*, 2005, 307:1634.

Herrea-Estrella et al., "Chimeric genes as dominant selectable markers in plant cells" *The EMBO Journal*, 1983, 2(6):987-995.

Hong et al., "A rice brassinosteroid-deficient mutant, ebisu dwarf (d2), is caused by a loss of function of a new member of cytochrome P450," *Plant Cell*, 2003, 15:2900-2910.

Hwang and Goodman, "An *Arabidopsis thaliana* root-specific kinase homolog is induced by dehydration, ABA, and NaCl" *Plant J.*, 1995, 8:37.

Hyrup et al., "Peptide Nucleic Acids (PNA): Synthesis, Properties and Potential Applications" *Bioorgan. Med. Chem.*, 1996, 4(1):5.

Ishida et al., "High efficiency transformation of maize (*Zea mays* L.) mediated by *Agrobacterium tumefaciens*" *Nature Biotechnology*, 1996, 14:745-750.

Kankel et al., "*Arabidopsis* MET1 Cytosine Methyltransferase Mutants," *Genetics*, 2003, 163:1109.

Lewis, *Genetic Engineering News*, 1992, 12:1.

May et al., "Generation of Transgenic Banana (*Musa acuminata*) Plants via *Agrobacterium*-Mediated Transformation" *Biotechnology*, 1995, 13:486-492.

Nair et al. "Identification of a CYP84 Family of Cytochrome P450-Dependent Mono-Oxygenase Genes in *Brassica napus* and Perturbation of Their Expression for Engineering Sinapine Reduction in the Seeds" *Plant Physiol.*, 123:1623-1634 (2000).

Purcell et al. "Antisense expression of a sucrose non-fermenting-1-related protein kinase sequence in potato results in decreased expression of sucrose synthase in tubers and loss of sucrose-inducibility of sucrose synthase transcripts in leaves" *Plant Journal*, 14:195-202 (1998).

Ronemus et al., "Demethylation-Induced Developmental Pleiotropy in *Arabidopsis*," *Science*, 1996, 273:654-656.

Salomon et al., "Genetic identification of functions of TR-DNA transcripts in octopine crown galls" The EMBO Journal, 1984, 3(1):141-146.

Sonnhammer et al., "Pfam: multiple sequence alignments and HMM—profiles of protein domains" *Nucl. Acids Res.*, 1998, 26: 320-322.

Sonnhammer et al., :Pfam: A Comprehensive Database of Protein Domain Families Based on Seed Alignments *Proteins*, 1997, 28:405-420.

Summerton and Weller, "Morpholino Antisense Oligomer: Design, Preparation, and Properties" *Antisense Nucleic Acid Drug Dev.*, 1997, 7(3):187-195.

Tanabe et al., "A novel cytochrome P450 is implicated in brassinosteroid biosynthesis via the characterization of a rice dwarf mutant, dwarf11, with reduced seed length," *Plant Cell*, 2005, 17:776-790.

Van der Meer et al. "Promoter analysis of the chalcone synthase (chsA) gene of Petunia hybrida: a 67 bp promoter region directs flower-specific expression" *Plant Mol. Biol.*, 15:95-109 (1990).

Vinkenoog et al., "Hypomethylation Promotes Autonomous Endosperm Development and Rescues Postfertilization Lethality in fie Mutants," *The Plant Cell*, 2000, 12:2271-2282.

Weiss, "Hot Prospect for New Gene Amplifier," *Science*, 1991, 254:1292-1293.

Chapple, C., "Molecular-Genetic Analysis of Plant Cytochrome P450-Dependent Monooxygenases," *Am. Rev. Plant Physiol. Plant Mol. Biol.*, 1998, 49:311-343.

Guo et al. "Protein tolerance to random amino acid charge" *PNAS*, 2004. 101: 9205-9210.

Lewis, Rick. "PCR's Competitors Are Alive and Well and Moving Rapidly Towards Commercialization" *Genetic Engineering News*, 1992, 12(9) 1, 7-9.

Nelson, David R., "Cytochrome P450 Nomenclature," Methods in Molecular Biology, 107, Cytochrome P450 Protocols, Edited by: I.R. Phillips & E.A. Shephard, Humana Press, Inc., Totowa, NJ, 1998.

Thornton et al. "From structure to function: Approaches and limitations" *Nature Structural Biology, Structural Genomics Supplement*, 2000 Nature America, Inc., http://structbio.nature.com., Nov. 2000.

```
  1 ATGTGGGTATTATATTGTTGGGTTCGGTTTGAGCTACACAATATAAATTTCGTGTTTCTGGT   60
 61 TATTCTGTTCACATGATTTGAGTTTGGTTCTCAATTTGGATTCCAAGATAATTAAATATT   120
121 AAAATTCATTTAAAAATATTTACAAGTAATTAATTATCTTTACATTGTATTGTTATAACAA   180
181 AATATCTATCTTTGGTATATGAGAAAAATATGGAGTTTGGAATTTATAATAATAAAGGAAA   240
241 TAATCGATTCCATTGGTTGGATTACACAGTTAAGTTTTTGTGTTTCTTTTGTTATATGT   300
301 ATATGAGTAAATCAAAAAGAGTATTGATTGAAGTGTAAACATATTTCGTTATGACCCCCA   360
361 AAAAAAAAAAAAAACAAACAAACCCCCCCGATATAGTTTTTGGTTCTGGATT   420
421 AGGTTTATTTGATCATAATTACATGCATCATTTCTTTGATTACTATGAAGATTTTCTTAC   480
481 CAATTAAAAATTTCGAATTCATATCTCTTGATTATTAAATTAAAATACGAGTGTGAATATCC   540
```

FIG. 10A

```
541  GTTTATCGATCACTCCAATCATGATTATGATTCTTGTGCTAATCCAGCAAATTATTAACA  600
601  AGAGTATTGAGAAAAACCGAAATAAGAAAAAGGGAAAGAGTAGTGACCCATGGAGTATG   660
661  TGAATAATTATCAAAGAGAATAAGAGATGACAACCAAAAGGTTGTGGAATAATGGTCCCT  720
721  GCCAGCTTTCTCTCACAATCAATATCGACCCTATTTGGATTTTCTGGATATTCGTTAAAA  780
781  TTTGCGGATAACGATTGTGAAAAATATTTTATTTGTTAGCTGATCTCAATATTATGTTCCA 840
841  GGTATTTGCATAATCTTCTGTTAAAGCATATATTTGTCTTTCTTTTTGTTCGTTCTCT    900
901  TAACTATATATTATCGCGGATATATGATAACAATGATATATCACAAAACAATTGTCTGGG 960
961  ACCATTTTGAATAAACTTTTTCTCAAACATTACGGGACACTGGACTGACCCCTTAAAATA 1020
```

FIG. 10B

1021 CGATTTTACAGGCGTCACTAGTTGAGATTACTAGCATAAAGGACCCGTTCAAGC 1080

1081 TATTTATACAAAGTTACAAACTGAATATAGCTTGAAATCCTTTAGAAAATTTTGGAATTA 1140

1141 CCGGTTGTTATGTAAATATAGATTTAGTGGTAAACAAATATGTTAATCAATTAGTGGTCA 1200

1201 ACATATACATAATTCCTTACAGAAAAACAAACTTAAGAGAAGTTAACATATCCATATAT 1260

1261 GGGTATGCTATACCTTTCAGTATGCTATACTAGAGACTAAAGAATAGTTATGTGATGTC 1320

1321 GATAAATGAAATTCACACGCGTGGTAATAATTATGGGACCGTATGTTACGATCACTGCAA 1380

1381 ATATCATTCTTGGTTGGTCAACAATAAAAACAAAAACAAGAAAAAAGAAAACGATTTTT 1440

1441 CTTGGATTCCATTCAATGATCTAAAATGCATAGATCTTTTGGGTTACAGTTTCGAAGTCC 1500

1501 TCTACAAGGCGTGTAACCATCTGCAACTATTAAAATTGCTTTCTTAATGCATCTTTAACAT 1560

FIG. 10C

1561 ATTTATTGTTAGTTGGAATTTAATAAGAGGCGAACTTGTAACATTACAATATTTATATTAG 1620

1621 ATACTAGTATGTGATTATTCCAAATACATACTTTGGATGTTTAAACTTAATCTTGTTTCT 1680

1681 TCCTACGGTATAAATATTAATCATCGAGGTAAAAAAAGTTTTGTCTTATTTTCGCGATGC 1740

1741 ATGAAGGATAAACCTAATGACTTTAATTTTTTGAAAATGTAACCCTTTTACTCATAGATT 1800

1801 AATTACCGTATGTTTTGTTGCCATAATGACAGCCTCTACAACTGTGATAGTCAATTTTT 1860

1861 TCTGCAAATATTAAATTAGGAATTCAATGCTACTATCAATAGAGAAACAGCTGAGTATT 1920

1921 ACATTTAATTTAAAGACAAAATTTTGAAAAATGTTATAATTCTAACAATATTATTAA 1980

1981 AATATGATGCCTATAATGTATTCCTATGTCTTAAAATATTTTTTTATATTAGTTA 2040

2041 TAAATACATTATGAACCAATAATAGTGGTGAATTCAAATATCTCCATTAATATTTTTG 2100

FIG. 10D

```
2101  AAATCTACAAATTATTAATATTTAGTCAATAACAATGCATAGAAAGTTCCAAAAAAATT  2160

2161  TTGTTAACAGAAACTTCCAAATTTTTTTTTTATGGAACAAGAGAAATAACAGATAGAAAA  2220

2221  CTATTTGTTGTGGAATGGAAGTAGTAATATACATTAAGCAAATTTAAAAAATTATATA  2280

2281  AGCCTATACGCGCTCAAAGTATGTTATCTAGTAGGTGTAATTAATAATGCATGGTGCGAT  2340

2341  TCAGAATTGGGACAACAATGAAAACGGAATTAAAATATTAACTTTAAAATAAATAAAAAT  2400

2401  TTGAGTAAATGTGTTTTCTGACTATTGAGGGGCAAAAAAAAGACAATGCCAAAAGTCTAC  2460

2461  GGGTTTGACTGTCCAGTTCGGTAATAATCTAATAACTCTGTCTTTGACCGGCACGCTCGTG  2520

2521  TAGGGGTCCTTCTGACATTTTCACTGTTCTACCCCTACTCGTGAGCCCACCCTTTTCCCA  2580

2581  TATCCTAAGGGTAATTTTGGAAATCCCAATTTAAACCGATTGAGACCGTACCGGACTTCC  2640
```

FIG. 10E

```
2641  TGGGATTCTGCTGGAGCATTTATCAAAAATTATTAGCACGGAATGGGTTTATTAATTTAAA  2700

2701  AACTCACAACTTGATCAGATAAAATTCATAAACACTTTACGATGGATTCGTACGATCT    2760

2761  ATCTAATGACTTTTTTTTTCTACCACGGTGGATGAAAGTTATAGTACTATTAGCCAGAG    2820

2821  ACAATTGATTATAGATATATCCATTAATCCATGATATTTATGATATAAATAGCTGTTAAA   2880

2881  CTATTTCAGCATCGCAGCTTTCTGCAACTTTTGTTTTTAATTTAAGAGTTTAATAAATAA   2940

2941  AAGTATTAAAAGGGAGCATAACGAGGCAACAAAAGTAATGAACACGGAGAAACAAAAGCCA  3000

3001  TGAAGCTCATTGGTTAGTTTAAGCTTAATAAGAAGATTTATTAAATTTAATGACGATG    3060

3061  ATAACAATTATATTTCTGACTTCTTTAAAACCCCTCTTACAAACAGAGCTCCCTTTT    3120

3121  TCAGTAGAAGTCCGATTCCCAATCTTAAAGACAAGCCATTAGAAAGAGAAAGTGAGTGA   3180
```

FIG. 10F

```
3181 GAGAGAGAGAGAAACTAGCTCCATGTTCGAAACAGAGCATCATACTCTCTTACCTCTTCT 3240
                              ─────────────────────────────────
                                          exon 1
3241 TCTTCTCCCATGGCTTTGTCTCTCTTCTCTTGAAGAGAAGAAATAG 3300
     ─────────────────────────────────────────────
3301 AAAAACCAGATTCAATCTACCTCCGGGTAAATCCGGTTGGCCATTTCTTGGTGAAACCAT 3360

3361 CGGTTATCTTAAACCGTACACCGCCACAACACTCGGTGACTTCATGCAACAACATGTCTC 3420

3421 CAAGTAAACAACAACATCTTCCAAAAAAATCAAAAAACTCAAAAAAATAAATCCTCGTTTTTGAAATTT 3480
     ───
3481 GACTAATGTGTTTATTTTACAGGTATGGTAAGATATATAGATCGAACTTGTTTGGAGAA 3540
                           ──────────────────────────────────────
                                         exon 2
3541 CCAACGATCGTATCAGCTGATGCTGGACTTAATAGATTCATATTACAAAACGAAGGAAGG 3600
     ─────────────────────────────────────────────────────────
3601 CTCTTTGAATGTAGTTATCCTAGAAGTATAGGTGGGATTCTTGGGAAATGGTCGATGCTT 3660
     ─────────────────────────────────────────────────────────
3661 GTTCTTGTTGGTGACATGCATAGAGATATGAGAAGTATCTCGCTTAACTTCTTAAGTCAC 3720
     ─────────────────────────────────────────────────────────
```

FIG. 10G

3721 GCACGTCTTAGAAACTATTCTACTTAAAGATGTTGAGAGACATACTTTGTTTGTTCTTGAT 3780

3781 TCTTGGCAACAAAACTCTATTTCTCTGCTCAAGAGGAGGCCAAAAAGGTTTTTATTTTT 3840

3841 ATCTTTTATTTGCTAAATTTTTTGTTTATGAATCTTTAGAGTTTCTAACTTTTTTTTT 3900

3901 TTTAATTGAACAGTTTACGTTTAATCTAATGGCGAAGCATATAATGAGTATGGATCCTGG 3960

3961 AGAAGAAGAAACAGAGCAATTAAAGAAAAGAGTATGTAACTTTCATGAAAGGAGTTGTCTC 4020

4021 TGCTCCTCTAAATCTACCAGGAACTGCTTATCATAAAGCTCTTCAGGTACATTTATTTTT 4080

4081 TTTTGCTGTGTAAAGTCACAAACTCTCATTATAGGTTTTAATTTTATTTATGTGTTAAAT 4140

4141 AAAATATCTAAAAATGGTTGTGTAGTCACGAGCAACGATATTGAAGTTCATTGAGAGGAAA 4200

4201 ATGGAAGAGAGAGAAATTGGATATCAAGGAAGAAGAGAAGATCAAGAAGAAGAAGAAGTGAAAACA 4260

FIG. 10H

4261 GAGGATGAAGCAGAGATGAGTAAGAGTGATCATGTTAGGAAACAAGAACAGAGACGATGAT 4320

4321 CTTTTGGGATGGGTTTTGAAACATTCGAATTTATCGACGGAGCAAATTCTGATCTCATT 4380

4381 CTTAGTTTGTTATTTGCCGGACATGAGAcTTCTTCTCTGTAGCCATTGCTCTCGCTATCTTC 4440

4441 TTCTTGCAAGCTTGCCCTAAAGCCGTTGAAGAGCTTAGGGTAAGATAATTATAACAGCAC 4500

4501 AAGTTAATTACTACCAAATTGTTACGTATTATATAAGTTATTATAGAATTATTCTATTAG 4560

4561 AATATACGATGAAAAAAGTATGTATATTTAATTGTCACTAATTTATGTTTATTGATTA 4620

4621 TACTTTTTGAAGGAAGAGCATCTTGAGATCgCGAGGGCCAAGAAGGAACTAGGAGAGTCAG 4680

4681 AATTAAAATTGGGGATGATTACAAGAAAAATGGACTTTACTCAATGTGTATGTTACTATCATT 4740

4741 CTCATTATTTATTCTATGTTCATATGATTTATGATGAAACCAAAATTATTGATTTTTTTT 4800

FIG. 10I

```
4801  TTGGTGTGTGTGTGAAGGTTATAAATGAAACTCTTCGATTGGGAAATGTAGTTAGGTTTTTG  4860
4861  CATCGCAAAGCACTCAAAGATGTTCGGTACAAAGGTAAAACTTTACGTACAAAATTTTTA   4920
4921  AATAATGAAATCCGGAATATTGAAATCTTATTGGATGAAAAATATTAAAATAATTTACAT  4980
4981  TTCTTAATGTTGGAAAAAAAGGATACGATATCCCTAGTGGGTGGAAAGTGTTACCGGTGAT  5040
5041  CTCAGCCGTACATTTGGATAATTCTCGTTATGACCAACCTAATCTCTTTAATCCTTGGAG  5100
5101  ATGGCAACAGGTAAATATAAAAGTTTCTCTCGTTAACTATCGAAAATTAGTGTATAGTTTT  5160
5161  TTCATCTATTGCATGAATAGATACGTCCTACGTGATTTACCTATCTATAGATACTATACG  5220
5221  AGAACTATTAATCTGGCAAAAACTTTTTATTATTATTATCTTTCAAGTTAGATCTTAACA  5280
5281  CGTCATGGATCATTGATCACATGAAAGCATATAAATTAAAAATAAGAGAGAGAAAGAGAC  5340
```

FIG. 10J

5341 GTGTTGGTGTGTAAGTGTACGTGAAGACAATTAATTAGTAGGATGGTATGTCTTTAATGACG 5400

5401 TAGGAGCTGCCTAAATATTCTTATAATCGTGACCGTTGATTATTATTAGTCACGGCTTT 5460

5461 GATACAATTTAAGATTTGACGGACGATGGTACCACGGCTTTGACGGATCTCACACGCCCG 5520

5521 ATGACTTGTACGTGCGTTAGATTCTGCCACGTTGACTGGTTTAATACTTAGATTTATAA 5580

5581 CTCTATTAATTATAACAACTATCAAATCGGCGAATTAGAGAAATATACTATATAGTATTA 5640

5641 TTATGATTATTATGAGATAATACTTTATGAAATAAGATAATAATGGTAGTCATGATGTTA 5700

5701 TAGTGAGTGGGGAAGGTAAGAGAGGTGGTGAGAGATGATTAATGACCCCACGTGGTGTGGTG 5760

5761 CCAACAAGCACGTGTTCTTCTCCTTTTTCTTCCCAACTTCTTTTTTGGGGGTTTATT 5820

5821 GTGATTTATAAAATCGGTTTGTCGTTTTTTTTGTGACGAGCAGCAAAACAACGGAGCGT 5880
                                                                    ═══════
                                                                    exon 8

FIG. 10K

```
5881  CATCGTCAGGAAGTGGTAGTTTTTCGACGTGGGGAAACAACTACATGCCGTTTGGAGGAG  5940
5941  GGCCAAGGCTATGTGCTGGTTCAGAGCTAGCCAAGTTAGAAATGGCAGTGTTATTCATC   6000
6001  ATCTAGTTCTTAAATTCAATTGGGAATTAGCAGAAGATGATCAACCATTGCTTTTCCTT   6060
6061  TTGTTGATTTTCCTAACGGTTTGCCTATTAGGGTTTCTCGTATTCTGTAAAAAAAAAAA   6120
6121  AGATGAAAGTATTTTTATTCTCTTCTTTTTTTGATAATTTAAATCATTTTTTGC        6180
6181  CCAATGATATATAAAAATTGGATAAATAATATTATTGGATATTCGTTTTTAGTTCGGG    6240
6241  TTTGAGAAAAGGGTTTCGACTTTTCGAAAGTGGACGATGTATATAGATTGGGAGCTAGGTT 6300
6301  GAGTCTTTGGACATTGTATTGGATGTGTTGATTATTAGTGTCGACACTATTAAACCTT    6360
6361  AAATGGGCTTTCTATAAGGCCCAATTATATTACGATTATAACAAAGTGACAACTTTTACT  6420
```

FIG. 10L

```
6421 TCGTTTTGATCCGAAGCAATAACAAATTGTCAAATACCAAACACAAGAATTATGTAAAC 6480

6481 ACTCGTGTGTCTAGTGGGAAATCATTGGGCTGGAGACTGAACATCAGAACACAAGAAA 6540

6541 CCTGTCAATTATGGATACACCTCCTATGACGGTTTCCAAACTTTATCTTGATTCTTATCG 6600

6601 TGTTACATTGACACAAAGAGTTAGGTGTCAAAAGGACTAAATGAATAACAATAGCTCTCA 6660

6661 GGATAAGAAGGTTCATAAAATGGTTTCTTTATTTTGAGAAGAAAGAGAGAGAGGAGCTTTA 6720

6721 CTGTTCTTGGGTCCTATTCCTTTAAATGAGAGGGTTTCGTTTTTACTTCTTCTATCTCA 6780

6781 TCATCTTTAGGATCCCTCTTCTAGACGAGTAAAGTAATCCTCGTTACCAAGCAATGGTCTC 6840

6841 ATCTTTTGAAGACAGGTCTTTTCCAAGTCCTAGTTCAGGCCAAAGCTT 6888
```

FIG. 10M

```
  1 MFETEHHTLL PLLLLPSLLS LLLFLILLKR RNRKTRFNLP PGKSGWPFLG ETIGYLKPYT
 61 ATTLGDFMQQ HVSKYGKIYR SNLFGEPTIV SADAGLNRFI LQNEGRLFEC SYPRSIGGIL
121 GKWSMLVLVG DMHRDMRSIS LNFLSHARLR TILLKDVERH TLFVLDSWQQ NSIFSAQDEA
181 KKFTFNLMAK HIMSMDPGEE ETEQLKKEYV TFMKGVVSAP LNLPGTAYHK ALQSRATILK
241 FIERKMEERK LDIKEEDQEE EEVKTEDEAE MSKSDHVRKQ RTDDDLLGWV LKHSNLSTEQ
301 ILDLILSLLF AGHETSSVAI ALAIFFLQAC PKAVEELREE HLEIARAKKE LGESELNWDD
361 YKKMDFTQCV INETLRLGNV VRFLHRKALK DVRYKGYDIP SGWKVLPVIS AVHLDNSRYD
421 QPNLFNPWRW QQQNNGASSS GSGSFSTWGN NYMPFGGGPR LCAGSELAKL EMAVFIHHLV
481 LKFNWELAED DQPFAFPPFVD FPNGLPIRVS RIL
```

FIG. 11

DWF4 POLYNUCLEOTIDES, POLYPEPTIDES AND USES THEREOF

CROSS-REFERENCE TO RELATED APPLICATIONS

This application is a continuation and claims the benefit of priority under 35 U.S.C. §120 of U.S. patent application Ser. No. 11/333,636, filed Jan. 17, 2006, now U.S. Pat. No. 7,589,255, which is a continuation of U.S. patent application Ser. No. 10/804,772, filed Mar. 18, 2004, now U.S. Pat. No. 7,253,336, which is a divisional of U.S. patent application Ser. No. 09/502,426, now U.S. Pat. No. 6,987,025, filed Feb. 11, 2000, which claims the benefit of U.S. Provisional Application No. 60/119,657, filed Feb. 11, 1999, and U.S. Provisional Application No. 60/119,658, filed Feb. 11, 1999, under 35 USC §119(e)(1). All such applications are incorporated herein by reference in their entireties.

STATEMENT AS TO FEDERALLY FUNDED RESEARCH

This invention was made with government support under IBN9604439 awarded by the National Science Foundation. The government has certain rights in the invention.

TECHNICAL FIELD

The present invention relates to novel polynucleotides isolated from dwarf plants. The dwf4 polynucleotides encode all, or a portion of, a DWF4 polypeptide, a cytochrome P450 enzyme that mediates multiple steps in synthesis of brassinosteroids. The present invention also relates to isolated polynucleotides that encode regulatory regions of dwf4. Uses of the dwf4 polypeptides and polynucleotides are also disclosed.

BACKGROUND

Plant growth is accomplished by orderly cell division and tightly regulated cell expansion. In plants, the contribution of cell expansion to growth is of much greater significance than in most other organisms; all plan organs owe their final size to a period of significant cell elongation, which usually follows active cell division. Further, the sessile nature of plants requires that they make fine but responsive adjustments in growth to survive harsh environmental conditions and to optimize their use of limited resources (Trewavas (1986) "Resource allocation under poor growth conditions: A major role for growth substances in developmental plasticity". In Plasticity in Plants, D. H. Jennings and A. J. Trewavas, eds (Cambridge, UK: Company of Biologists Ltd), pp. 31-76).

In *Arabidopsis*, cell elongation is largely responsible for hypocotyls grown in germinating seedlings and extension of inflorescences (bolting) at the end of vegetative growth. Coordinate control of plant growth is regulated by both external stimuli and internal mechanisms. Of the external signals, the most obvious is light (Deng, X.-W. (1994) *Cell* 76:423-426). Light inhibits hypocotyls elongation and promotes cotyledon expansion and leaf development in seedlings, and photoperiod is crucial for flower initiation in a large number of species.

The internal components of plant signaling are generally mediated by chemical growth regulators (phytohormones; reviewed in Klee, H. and Estelle, M. (1991) *Annu. Rev. Plant Physiol. Plant Mol. Biol.* 42:529-551). Thus, plant growth in response to environmental factors is modulated by plant hormones acting alone or in concert (Evans "Functions of hormones at the cellular level of organization" In Hormonal Regulation of Plant Physiology, T. K. Scott, ed (Berlin: Springer-Verlag), pp. 23-79), and growth depends on regulated cellular events, such as division, elongation, and differentiation.

Gibberellic acid (GA) and cytokinins promote flowering; in addition, GA stimulates stem elongation, whereas cytokinins have the opposite effect, reducing apical dominance by stimulating increased axillary shoot formation. Conversely, auxins promote apical dominance and stimulate elongation by a process postulated to require acidification of the cell wall by a K dependant $H^+$-pumping ATPase (Rayle, D. L., and Cleland, R. E. (1977) *Curr. Top. Dev. Biol.* 11:187-214).

In addition to the classic hormones, such as auxin and gibberellic acid (GA), brassinosteroids (BRs) have been discovered to be important in growth promotion (reviewed in Clouse (1996) *Plant J.* 10:1-8). The most recently discovered class of plant growth substances, the BRs, has been to date the least studied; however, rapid progress toward understanding BR biosynthesis and regulation is now being made (Yokota, T. (1997) *Trends Plant Sci.* 2:137-143). The term BRs collectively refers to the growth-promoting steroids found in plants (Grove et al. (1979) *Nature* 281:216-217. They are structurally very similar to the molting hormones of insects, ecdysteroids (Richter and Koolman (1991) "Antiecdysteroid effects of brassinosteroids in insects" in Brassinosteroids: Chemistry, Bioactivity, and Applications, H. G. Cutler, T. Yokota, and G. Adam, eds (Washington, D.C.: American Chemical Society); pp. 265-279), but active BRs have unique structural features. As shown in FIG. 1, a 6-oxolactone or 7-oxalactone in the B ring, 5α hydrogen, and multiple hydroxylations at four different positions with specific stereochemistry have been proposed as an essential configuration for BRs (reviewed in Marquardt and Adam (1991) "Recent advances in brassinosteroid research" in Chemistry of Plant Protections, W. Ebing, ed (Berlin: Springer-Verlag), pp. 103-139). Among>40 naturally occurring BRs, brassinolide (BL; 2α, 3α, 22(R), 23(R)-tetrahydroxy-24(S)-methyl-B-homo-7-oxa-5α-cholestan-6-one) has been shown to be the most biologically active (reviewed in Mandava (1988) *Annu. Rev. Plant Physiol. Plant Mol. Biol.* 39:23-52). As a major biological effect, BRs stimulate longitudinal growth of young tissues via cell elongation and cell division (reviewed in Clouse (1996), supra; Fujioka and Sakurai (1997a) *Nat. Prod. Rep.* 14:10).

Elucidating the BR biosynthetic pathways has been a major area of recent interest. Biochemical analyses have been used to elucidate the BR biosynthetic pathway (Fujioka et al. (1996) *Plant Cell Physiol.* 37:1201-1203; Choi et al. (1997), *Phytochemistry* 44:609-613), and mutational analyses are being used to confirm this pathway. Similar to the biosynthetic pathways of the human steroid hormones and insect ecdysteroids (Rees (1985) "Biosynthesis of ecdysone" in Comprehensive Insect Physiology, Biochemistry and Pharmacology, G. A. Kerkut and L. I. Gilbert, eds (Oxford, UK: Pergamon Press), pp. 249-293; Granner, D. K. (1996) "Hormones of the gonads" in Harper's Biochemistry, R. K. Murray, D. K. Granner, P. A. Mayes, and V. W. Rodwell, eds (Stamford, Conn.: Appleton and Lange press); pp. 566-580), BRs are synthesized via multiple parallel pathways (Fujioka et al. (1996) Plant *Cell Physiol.* 37:1201-1203; Choi et al. (1997) supra). Starting from the initial precursor, campesterol (CR), the BR intermediates undergo a series of hydroxylations, reductions, an epimerization, and a Baeyer-Villigerû-type oxidation leading to the most oxidized form, BL (Fujioka and Sakurai (1997b) *Physiol. Plant.* 100:710-715;

FIG. 1). Castasterone (CS oxidation, the last step in BR biosynthesis, is not found in some species, such as mung bean. In that case, CS plays a role as the major BR rather than BL (Yokota et al. (1991) "Metabolism and biosynthesis of brassinosteroids" in Brassinosteroids: Chemistry, Bioactivity, and Application, H>G>Cutler, T. Yokota, and G. Adam, eds (Washington, D.C.: American Chemical Society), pp. 86-96). Traditionally, BR biosynthetic pathways have been elucidated by feeding deuterio-labeled intermediates to BR-producing cell lines of Madagascar periwinkle (Sakurai and Fujioka (1996) "Catharanthus roseus (Vinca rosea): In vitro production of brassinosteroids" in Biotechnology in Agriculture and Forestry, Y. P. S. Bajaj, ed (Berlin: Springer-Verlag), pp. 87-96). The present model, including parallel branched pathways and early and late C-6 oxidation pathways, was established using these feeding studies (Fujioka and Sakurai (1997a) supra, Fujioka and Sakurai (1997b), supra; Sakurai and Fujioka (1997) Biosci. Biotechnol. Biochem. 61:757-762).

Although the brassinosteriod system is a less well understood class of plant growth substances (BRs Mitchell, et al. (1970) Nature 225:1065-1066; Grove et al. (1979) Nature 281:216-217; Mandava, N. B. (1988) Annu. Rev. Plant Physiol. Plant Mol. Biol. 39:23-52), several such compounds have been identified and are known to effect elongation of cells in various plant tissues, their biosynthesis, regulation, and mechanism of action have only recently begun to be elucidated (reviewed in Clouse, S. D. (1996) Plant J. 10:1-8; Fujioka, S., and Sakurai, A. (1997) Physiol. Plant 100:710-715).

Several types of dwarf or dwarflike mutants have been described in Arabidopsis. A number of mutations have been identified that affect either light-dependent (cop, det, and fusca [fus; another group of mutants with some members perturbed in light-regulated growth]) or hormone signaling (axr2) pathways and whose pleiotropic phenotypes include defects in cell elongation. The majority of these mutants also have other alterations in their phenotypes. At least five GA mutants have been described as being reduced in stature (Koornneef and Van der Veen (1980) Theor. Appl Genet. 58:257-263).

Another hormone mutation, auxin resistant2 (axr2), results in plants with a dwarf phenotype both in the light and in darkens as well as increased resistance to high levels of auxin, ethylene, and abscisic acid (Timpte et al. (1992) Planta 188: 271-278). An interesting relationship exists between light regulation and cytokinin levels. Arabidopsis seedlings grown in the dark in the presence of cytokinins have open cotyledons, initiate chloroplast differentiation and leaf development, and activate transcription from the chlorophyll a/b binding protein gene (CAB) promoter. Importantly, they also display a cytokinin dose-dependent dwarf phenotype.

Dwarf Arabidopsis mutants that are rescued by addition of BRs have also been described (Kauschmann et al. (1996) Plant J9:701-713; Li et al. (1996) Science 272:398-401; Szekeres et al. (1996) Cell 85:171-182; Azpiroz et al. (1998) Plant Cell 10:219-230), including the following three mutants: dwarf1 (dwf1; Kauschmann et al. (1996) Plant J. 9:701-713), constitutive photomorphogenesis and dwarfism (cpd; Szekeres et al. (1996) Cell 85:171-182), and det2 (Li et al. 91996) Science 272:398-401). These mutants have been shown to be defective in steroid biosynthesis. DWF1 (Feldmann et al. (1989) Science 243:1351-1354) was cloned first (GenBank accession number U12400). Takahashi et al. (1995) Genes Dev. 9:97-107 hypothesized that DWF1, which they isolated with an allele of dwf1, referred to as diminutol (dim 1), contains a potential nuclear targeting signal, which may confer a regulatory function to the protein. However, Mushegian and Koonin (1995) Protein Sci. 4:1243-1244 indicated that DWF1 displays limited homology with flavin adenine dinucleotide (FAD) independent oxidoreductase, suggesting an enzymatic function in BR biosynthesis. According to Kauschmann et al. (1996), supra (dwf1-6 described as cabbagel [cbb1]), dwf1 mutants were rescued by exogenous application of BRs.

DET2 was shown to encode a putative steroid 5α-reductase, mediating an early step in BR biosynthesis (Li et al. (1996) supra, Li et al. (1997) Proc. Natl. Acad. Sci. USA 94:3554-3559; Fujioka et al. (1997) Plant Cell 9:1951-1962; FIG. 1). Moreover det1 and det2 have a decreased requirement for cytokinins in tissue culture and appear to be saturated for a cytokinin-dependent delay in senescence (Chory et al. 91994) Plant Physiol. 104:339-347). CPD has been proposed to be a novel cytochrome P450 (CYP90A1; Szekeres et al. (1996), supra), encoding a putative 23α-hydroxylase that acts in BR biosynthesis. The range of phenotypes in the deetiolated (det) and constitutive photomorphogenic (cop) light-regulatory mutants is broad. Mutations in DET1, COP1, COP8, COP9, COP10, and COP11 result in constitutive derepression of substantial portions of the photomorphogenic program (Chory, et al. (1989b) Cell 58:991-999; Deng, X-W., and quail, P. H. (1992) Plant J. 2:83-95; Wei, N., and Deng, X-W (1992) Plant Cell 4:1507-1518; Wei et al. (1994) Plant Cell 6:629-643), whereas mutations in COP4 seem to affect only morphology and gene expression (Hou et al. (1993) Plant Cell 5:329-339). The only invariant phenotype in this class of light-regulatory mutants is a substantial reduction in height in both light and darkness.

There are additional dwarfs that are insensitive to one of these hormones, such as bri (brassinosteroid insensitive; Clouse et al. (1996) Plant Physiol. 111:671-678; Li and Chory (1997) Cell 90:929-938), gai (gibberellic acid insensitive, Koommeef et al. (1985) Physiol. Plant. 65:33-39), and axr2 (auxin resistant2; Timpte et al. (1994) Genetics 138: 1239-1249). Clouse et al. (1996), supra isolated bri by screening ethyl methanesulfonate-mutagenized populations for mutants whose root growth is not retarded at inhibitory concentrations of BR. Thus, the BR1 protein is proposed to be involved in BR signal perception or transduction (Clouse (1996), supra). Kauschmann et al. (1996), supra described a phenotypically similar mutant cbb2 that maps to the same location. In addition, the dwf2 alleles possess a phenotype similar to bri and map to the same region (Feldmann and Azpiroz (1994) "dwarf (dwj) and twisted dwarf (twd)" in Arabidopsis: An Atlas of Morphology and Development, J Bowman, ed (New York: Springer-Verlag), pp. 82-85). It seems likely that all of the BR-insensitive dwarf mutants described to date are allelic. Recently, BR1 has been cloned and shown to encode a leucine-rich-repeat receptor kinase, suggesting a role in the BR signal transduction pathway (Li and Chory (1997), supra).

Mutants defective in BR biosynthesis have also been isolated in other plant species. Bishop et al. (1996) Plant Cell 8:959-969 isolated a tomato dwarf mutant by transposon tagging. The tomato Dwarf gene encodes a pioneering member of the CYP85 family, and it appears to be involved in BR biosynthesis. In addition, Nomura et al. (1997) Plant Physiol. 113:31-37 reported that the lka and lkb mutants in garden pea are deficient in BR biosynthesis (lkb) or perception (lka).

Currently, little is known about the downstream events that occur in response to these signals and thereby directly control cell size. This is because the biochemical and cell biological processes involved have thus far been difficult to address. In addition, there is little information about the integration of regulatory signals converging at the cell form different signaling pathways and the ways they are coordinately controlled. In particular, the interaction of light and hormones in the control of cell elongation is not clear. Thus, there remains a need for the identification and characterization of additional mutants and polypeptides encoded thereby involved in these pathways of plant growth.

SUMMARY OF THE INVENTION

In one aspect the invention includes an isolated dwf4 polynucleotide comprising an open reading frame that encodes a polypeptide comprising (i) a sequence having greater than 43% identify to 10 contiguous amino acids of SEQUENCE ID NO:2; (ii) a sequence comprising at least about 10 contiguous amino acids that have greater than 43% identity to 10 contiguous amino acids of SEQUENCE ID NO:2, or a complement or reverse complement of said polynucleotide. In certain embodiments, the polynucleotide will have at least 70% identity to the DWF4 polypeptide-coding region of SEQ ID NO:1 or to complements and reverse complements of this region. In further embodiments, the isolated dwf4 polynucleotide comprises the nucleotide sequence of SEQ ID NO:1, complements and reverse complements thereof. The polynucleotide may also comprise at least 30 consecutive nucleotides of SEQ ID NO:1.

In another aspect, the invention includes an isolated dwf4 polynucleotide comprising (i) a sequence having at least 50% identity to SEQ ID NO:1, complements and reverse complements thereof or (ii) a sequence comprising at least about 15 contiguous nucleotides that has at least 50% identity to SEQ ID NO:1, complements and reverse complements thereof. In certain embodiments, the isolated dw4 polynucleotide has at least 50% identity to the DWF4 polypeptide-coding region of SEQ ID NO:1, complements and reverse complements thereof. In further embodiments, the isolated dwf4 polynucleotides described herein comprise the nucleotide sequence of SEQ ID NO:1, complements and reverse complements thereof or nucleotide sequences comprising at least 30 consecutive nucleotides of SEQ ID NO:1. Any of the dwf4 polynucleotides described herein may be genomic DNA and may include introns. Further, in other embodiments, the dwf4 polynucleotide includes a dwf4 control control element comprising a polynucleotide selected form the group consisting of (i) a sequence having at least 50% identity to nucleotides 1 to 3202 of SEQ ID NO:1; (ii) a fragment of (i) which includes a dwf4 control element; and (iii) complements and reverse complements of (i) or (ii). In still further embodiments, the polynucleotide includes a dwf4 control element comprising a polynucleotide selected from the group consisting of (i) a sequence having at least 50% identity to nucleotides 6111 to 6468 corresponding to the 3' UTR of SEQ ID NO:1; (ii) a fragment of (i) which includes a dwf4 3' UTR; and (iii) complements and reverse complements of (i) or (ii). IN certain embodiments, the polynucleotide includes a dwf4 polynucleotide selected from the group consisting of (i) a sequence having at least 50% identity to the sequences corresponding to the introns of SEQ ID NO:1; (ii) a fragment of (i) which includes a dwf4 intro; and (iii) complements and reverse complements of (i) and (ii) Introns are found, for example, in the following regions: nucleotides 3424 to 3503 of SE ID NO:1; nucleotides 3829 to 3913 of SEQ ID NO:1; nucleotides 4067 to 4164 of SEQ ID NO:1; nucleotides 4480 to 4531 of SEQ ID NO:1; nucleotides 4725 to 4815 of SEQ ID NO:1; nucleotides 4895 to 5000 of SEQ ID NO:1; and nucleotides 5111 to 5864 of SEQ ID NO:1. 54. In still further embodiments, any of the polynucleotides described herein can operably linked to a nucleic acid molecule encoding a heterologous polypeptide (e.g., a cytochrome P450 polypeptide), for example, as a chimeric polynucleotide.

In another aspect, the invention includes recombinant vectors comprising (i) one or more of the polynucleotides described above; and (ii) control elements operably linked to the one or more polynucleotides, whereby a coding sequence within said polynucleotide can be transcribed and translated in a host cell. In certain embodiments, the recombinant vector comprises (a) any of the polynucleotides which include a dwf4 control element described above (e.g., promoter or introns); and (b) a nucleic acid molecule comprising a coding sequence operably linked to the dwf4 control element.

Host cells comprising and/or transformed with any of the recombinant vectors described herein are also provided. In certain embodiments, the host cells are cultured ex vivo while in other embodiments, the dwf4 polynucleotide is provided the host cell in vivo. In certain embodiments the DWF4 polypeptide is provided in amounts such that a plant is regenerated.

In another aspect, the present invention includes a method of modulating a DWF4 polypeptide comprising the following steps: (a) providing a host cell as described herein; and (b) culturing said host cell under conditions whereby the dwf4 polynucleotide included in the host cell is transcribed. In certain embodiments, the dwf4 polynucleotide is overexpressed. Alternatively, in other embodiments, the polynucleotide included in the host cell inhibits expression of dwf4.

In yet another aspect, the present invention includes a transgenic plant comprising any of the recombinant vectors described herein.

In yet another aspect, the invention includes a method of producing a recombinant polypeptide comprising the following steps: (a) providing a host cell as described herein; and (b) culturing said host cell under conditions whereby the recombinant polypeptide encoded by the coding sequence present in said recombinant vector is expressed.

In a still further aspect, the invention includes a method of producing a transgenic plant comprising the steps of (a) introducing a polynucleotide described herein into a plant cell to produce a transformed plant cell; and (b) producing a transgenic plant form the transformed plant cell.

Methods for producing a transgenic plant having an altered phenotype relative to the wild-type plant comprising the following steps: introducing at least one polynucleotide described herein into a plant cell; and producing a transgenic plant from the plant cell, said transgenic plant having an altered phenotype relative to the wild-type plant are also included in the present invention. The altered phenotype includes altered morphological appearance and altered biochemical activity, for example, altered (reduced or increased) cell length in any cell or tissue, altered (extended or decreased) periods of flowering, altered (increased or decreased) branching, altered (increased or decreased) seed production, altered (increased or decreased) leaf size, altered (elongated or shortened) hypocotyls, altered (increased or decreased) plant height, altered heme-thiolate enzyme activity, altered monooxygenase activity, altered 22α-hydroxylase activity, regulation of brassinosteriod synthesis, regulation of gibberellic acid, regulation of cytokinins, regulation of auxins, altered resistance to plant pathogens, altered growth at low temperatures, altered growth in dark conditions and altered sterol composition. IN certain embodiments, the at least one polynucleotide is operably linked to a promoter selected from the group consisting of a tissue-specific promoter, an inducible promoter or a constitutive promoter. The polynucleotide can be overexpressed or it can inhibit expression of dwf4. In a still further embodiment, at least two polynucleotides are introduced into the plant cell. Each polynucleotide is operably linked to a different tissue-specific promoter such that one polynucleotide is overexpressed while the other inhibits express of dwf4.

In yet another aspect, the invention includes a method for altering the biochemical activity of a cell comprising the following steps: introducing at least one polynucleotide described herein; and culturing the cell under conditions such that the biochemical activity of the cell is altered. Biochemical activity includes, for example, altered heme-thiolate enzyme activity, altered monooxygenase activity, altered 2α-hydroxylase activity, regulation of gibberellic acid, regulation of cytokinins, regulation of auxins, and altered sterol composition. In certain embodiments, the cell is cultured ex vivo. In still other embodiments, more than one dwf4 polynucleotides are provided to the cell.

In yet another aspect, the invention includes a method for regulating the call cycle of a plant cell comprising the following steps providing a dwf4 polynucleotide to a plant cell; and expressing the dwf4 polynucleotide to provide a DWF4 polypeptide, wherein the DWF4 polypeptide is provided in amounts such that cell cycling is regulated. In certain embodiments; the plant cell is provided in vitro and is cultured under conditions suitable for providing the DWF4 polypeptide. In still other embodiments, the dwf4 polynucleotide is provided in vivo.

In yet another aspect, the invention includes an isolated DWF4 polypeptide comprising (i) a sequence having greater than 43% identity to SEQ ID NO:2 or (ii) fragments of (i) that confer a DWF4 phenotype when expressed in a host organism. In certain embodiments, the isolated DWF4 polypeptide comprises the amino acid sequence of SEQ ID NO:2. In certain embodiments, the invention includes a chimeric polypeptide comprising a DWF4 polypeptide as described herein and a heterologous polypeptide for example a cytochrome P450 polypeptide.

Any of the polynucleotides or polypeptides described herein can be used in diagnostic assays; to generate antibodies. Further, the antibodies and fragments thereof can also be used in diagnostic assays, to produce immunogenic compositions or the like.

These and other objects, aspects, embodiments and advantages of the present invention will readily occur to those of ordinary skill in the art in view of the disclosure herein.

BRIEF DESCRIPTION OF THE DRAWINGS

FIG. 2A depicts the DWF4 coding sequence (1542 bp) and shows that the coding sequence contains eight exons and seven introns. The exons and introns range in length from 93 to 604 and 84 to 754 bp, respectively. All of the introns are bordered by typical consensus splice junctions, 5'-GU and AG-3'. Closed rectangles indicate exons. The T-DNA position in dwf4-1 is marked with an arrow.

FIGS. 3A and 3B depict an alignment of cytochrome P450 proteins that exhibited the most similarity to DWF4 (SEQ. ID NO:2) in BLAST searches. GenBank accession numbers are AF044216 (DWF4; CYP90B) (SEQ. ID NO:2), X87368 (CPD; CYP90A, SEQ ID NO:19), U54770 (tomato; CYP85, SEQ ID NO:20), D64003 (cyanobacteria; CYP120, SEQ ID NO:21), U32579 (maize; CYP88, SEQ ID NO:22), U68234 (zebrafish; CYP26, SEQ ID NO:23), and M13785 (human; CYP3A3X, SEQ ID NO:24). The consensus sequence is set forth in SEQ ID NO:25. Dashes indicate gaps introduced to maximize alignment. Domains indicated in FIG. 2B are highlighted in a box. Amino acid residues that are conserved >50% between the compared sequences are highlighted by a reverse font, and identical residues between DWF4 and CPD are boxed and italicized. Open triangles are placed under the 100% conserved residues. Closed triangles locate functionally important amino acid residues, for example, threonine (T) at 369, which is thought to bind molecular oxygen, and cysteine (C) at 516, which links to a heme prosthetic group by a thiolate bond. X's indicate mutated residues in dwf4 alleles. Multiple sequence alignment was performed using PILEUP in the Genetics Computer Group package, and box shading was made possible by the ALSCRIPT package (Barton (1993) *Protein Eng.* 6:37-40).

FIGS. 10(A)-10(M) depict the nucleotide sequence of wild-type dwf4 (SEQ ID NO:1, see, also, GenBank Accession Number AF044216). The dwf4 polynucleotide includes a coding region between nucleotides 3203 and 6110, inclusive. The coding region includes the following eight exons: nucleotides 3203 to 3423, inclusive; nucleotides 3504 to 3828, inclusive; nucleotides 3914 to 4066, inclusive; nucleotides 4165 to 4479, inclusive; nucleotides 4632 to 4724, inclusive; nucleotides 4816 to 4894, inclusive; nucleotides 5001 to 5110, inclusive and nucleotides 5865 to 6110, inclusive. The exons are indicated by a bar beneath the nucleotide sequence. A 5' control region (e.g., promoter) extends from nucleotides 1 to 3202. A 3' untranslated region (UTR), corresponds to the region extending from nucleotide to 6011 to approximately nucleotide 6468 of FIG. 10 (SEQ ID NO:1) and a TATA signal extending approximately from nucleotides 3060 to 3125. As described in the Examples, mutant alleles of dwf4 have also been characterized. For example, dwf4-1 contains an approximately 20 kb insert between nucleotides 5202 and 5203. dwf4-2 has a 9 base pair deletion corresponding to amino acids 324-326. In mutant allele dwf4-3, the guanine (G) residue at position 4332 is replaced with an adenine (A) residue to create a premature stop codon and truncate the DWF4 protein at amino acid 289.

FIG. 11 depicts the amino acid sequence of the DWF4 polypeptide (GenBank Accession Number AAC05093, SEQ ID NO:2). The polypeptide is 513 amino acids in length.

DETAILED DESCRIPTION

Figure 1A:
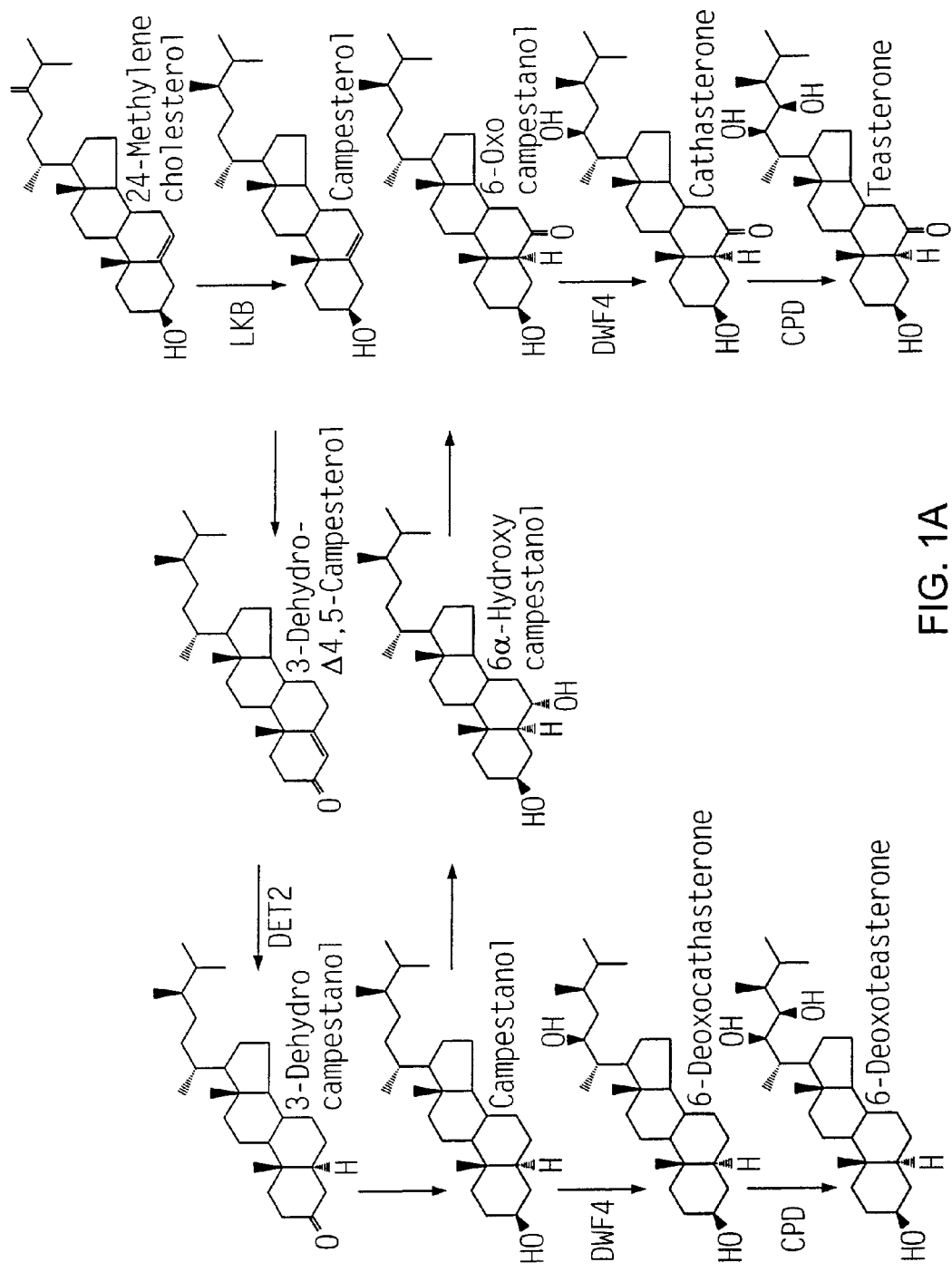
FIGS. 1A and 1B depict a proposed biosynthetic pathway for BL. CR goes through at least two different pathways, referred to as the early C-6 oxidation (right column) and late C-6 oxidation (left column) pathways. Steps mediated by DWF4, CPD (Szerkeres et al. (1996), supra), DET2 (Fujioka and Skaurai (1997a), infra; Li et al. (1997), supra) and LKB (Yokota et al. (1997), infra) are indicated.
Figure 1B:
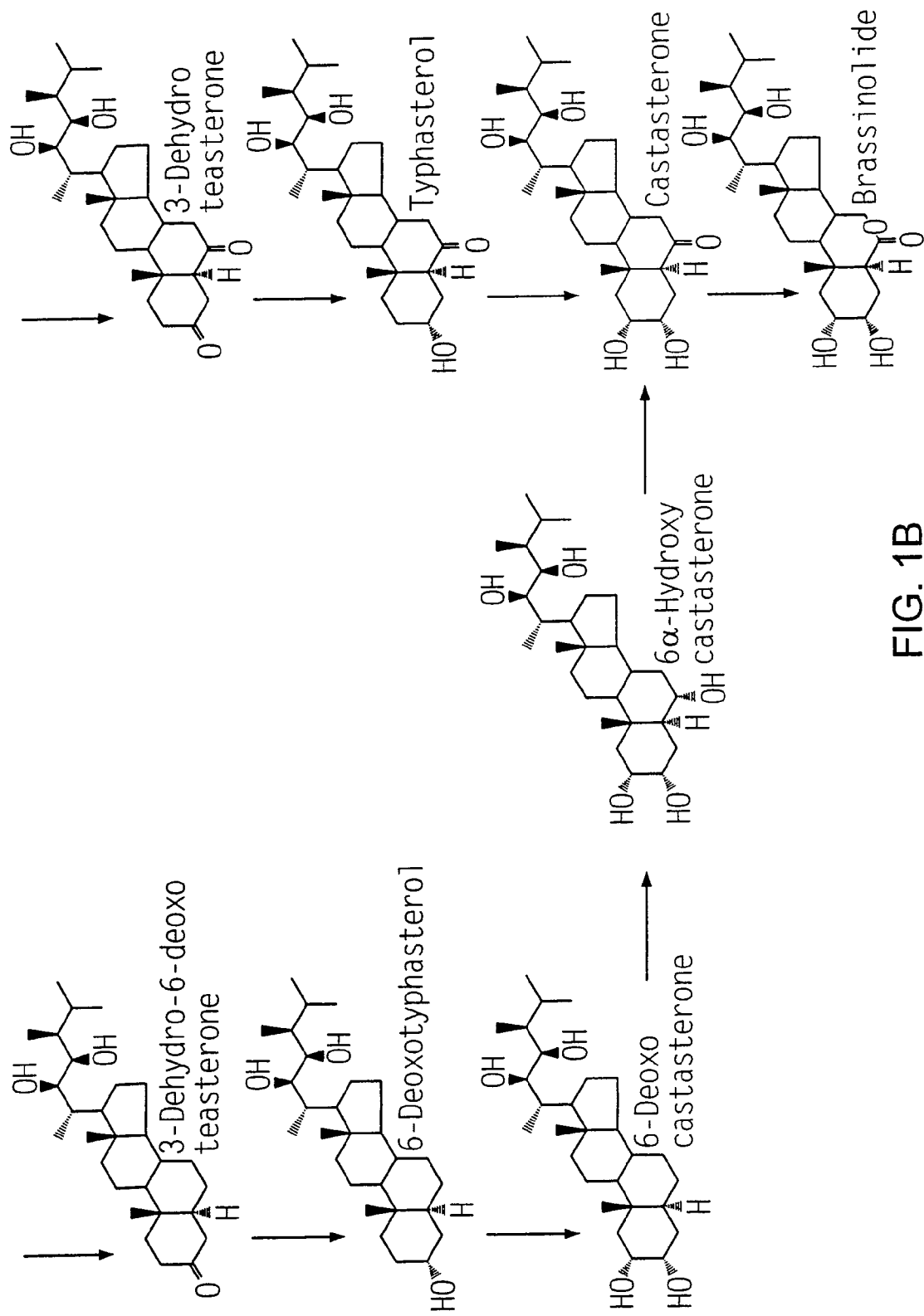

The novel dwf4 polynucleotides and DWF4 polypeptides described herein are important molecules in regulating cell growth and sterol synthesis. The present inventors have shown that dwf4 encodes a cytochrome P450 monooxygenase having 43% sequence identity to the protein term ed Constitutive Phoromorphogenesis and Dwfarism (CPD). As shown in FIG. 1 both CPD and DWF4 polypeptides appear to regulate biosynthesis of brassinosteriods, for example brassinolide (BL). However, unlike previously characterized proteins (e.g., CPD), DWF4 appears to act as a "gatekeeper" in these biosynthetic pathways in that its substrates (e.g., 6-Oxo campestanol and 6α-Hydroxy campestanol) are approximately 500 times more prevalent than the downstream molecules. Thus, the present invention represents an important discovery in understanding and regulating cell growth.

Before describing the present invention in detail, it is to be understood that this invention is not limited to particularly exemplified molecules or process parameters as such may, of course, vary. It is also to be understood that the terminology used herein is for the purpose of describing particular embodiments of the invention only, and is not intended to be limiting. In addition, the practice of the present invention will employ, unless otherwise indicated, conventional methods of plant biology, virology, microbiology, molecular biology, recombinant DNA techniques and immunology all of which are within the ordinary skill of the art. Such techniques are explained fully in the literature. See, e.g., Evans, et al., *Handbook of Plant Cell Culture* (1983, Macmillan Publishing Co.); Binding, *Regeneration of Plants, Plant Protoplasts* (1985, CRC Press); Sambrook, et al., *Molecular Cloning: A Laboratory Manual* ($2^{nd}$ Edition, 1989); *DNA Cloning: A Practical Approach*, vol. I and II (D. Glover, ed.); Oligonucleotide Synthesis (N. Gait, ed., 1984); *A Practical Guide to Molecular Cloning* (1984); and *Fundamental Virology*, $2^{nd}$ Edition, vol. I & II (B. N. Fields and D. M. Knipe, eds).

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "a polypeptide" includes a mixture of two or more polypeptides, and the like.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glue (E) | Glycine: Gly (G) |
| Histidine: His (H) | Isoleucine: Ile (I) |
| Leucine: Leu (L) | Llysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

Definitions

In describing the present invention, the following terms will be employed, and are intended to be defined as indicated below.

The terms "nucleic acid molecule" and polynucleotide" are used interchangeably and refer to a polymeric form of nucleotides of any length, either deoxyribonucleotides or ribonucleotides, or analogs thereof. This term refers only to the primary structure of the molecule and thus includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including e.g. nucleases, toxins, antibodies, signal peptides, poly-L-lysine, etc.), those with intercalators (e.g., acridine, psoralen, etc.), those containing chelates (e.g., metals, radioactive metals, boron, oxidative metals, etc.), those containing alkylators, those with modified linkages (e.g., alpha anomeric nucleic acids, etc.), as well as unmodified forms of the polynucleotide. Polynucleotides may have any three-dimensional structure, and may perform any function, known or unknown. Nonlimiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the alphabetical representation of a polynucleotide molecule. This alphabetical representation can be input into database in a computer having a central processing unit and used for bioinformatics applications such as functional genomics and homology searching.

Techniques for determining nucleic acid and amino acid "sequence identity" are known in the art. Typically, such techniques include determining the nucleotide sequence of the mRNA for a gene amino and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences I provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+Swiss protein+Spupdate+PIR. Details of these programs can be found at the following internet address: ncbi.nlm.gov/cgi-bin/BLAST.

Alternatively, the degree of sequence similarity between polynucleotides can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 43%-60%, preferably 60-70%, more preferably 70%-85%, more preferably at least about 85%-90%, more preferably at least about 90%-95%, and most preferably at least about 95%-98% sequence identity over a defined length of the molecules, or any percentage between the above-specified ranges, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning, supra; Nucleic Acid Hybridization*, supra.

The degree of sequence identity between two nucleic acid molecules affects the efficiency and strength of hybridization events between such molecules. A partially identical nucleic acid sequence will at least partially inhibit a completely identical sequence from hybridizing to a target molecule Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N>Y>). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chose that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Prac-*

*tical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g. formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

A "gene" as used in the context of the present invention is a sequence of nucleotides in a genetic nucleic acid (chromosome, plasmid, etc.) with which a genetic function is associated. A gene is a hereditary unit, for example of an organism, comprising a polynucleotide sequence that occupies a specific physical location (a "gene locus" or "genetic locus") within the genome of an organism. A gene can encode an expressed product, such as a polypeptide or a polynucleotide (e.g., tRNA). Alternatively, a gene may define a genomic location for a particular event/function, such as the binding of proteins and/or nucleic acids, wherein the gene does not encode an expressed product. Typically, a gene includes coding sequences, such as, polypeptide encoding sequences, and non-coding sequences, such as, promoter sequences, polyadenlyation sequences, transcriptional regulatory sequences (e.g., enhancer sequences). Many eukaryotic genes have "exons" (coding sequences) interrupted by "introns" (non-coding sequences). In certain cases, a gene may share sequences with another gene(s) (e.g., overlapping genes).

A "coding sequence" or a sequence which "encodes" a selected polypeptide, is a nucleic acid molecule which is transcribed (in the case of DNA)) and translated (in the case of mRNA) into a polypeptide, for example, in vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence. "Encoded by" refers to a nucleic acid sequence which codes for a polypeptide sequence, wherein the polypeptide sequence or a potion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), translation enhancing sequences, and translation termination sequences. Transcription promoters can include inducible promoters (where expression of a polynucleotide sequence operably linked to the promoter is induced by an analyte, cofactor, regulatory protein, etc.), tissue-specific promoters (where expression of a polynucleotide sequence operably linked to the promoter is induced only in selected tissue), repressible promoters (where expression of a polynucleotide seque4nce operably linked to the promoter is induced by an analyte, cofactor, regulatory protein, etc.), and constitutive promoters.

A control element, such as a promoter, "directs the transcription" of a coding sequence in a call when RNA polymerase will bind the promoter and transcribe the coding sequence into mRNA, which is then translated into the polypeptide encoded by the coding sequence.

"Expression enhancing sequences" typically refer to control elements that improve transcription or translation of a polynucleotide relative to the expression level in the absence of such control elements (for example, promoters, promoter enhancers, enhancer elements, and translational enhancers (e.g., Shine and Delagarno sequences).

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

A "heterologous sequence" as used herein typically refers to a nucleic acid sequence that is not normally found in the cell or organism of interest. For example, a DNA sequence encoding a polypeptide can be obtained from a plant cell and introduced into a bacterial cell. In this case the plant DNA sequence is "heterologous" to the native DNA of the bacterial cell.

The "native sequence" or "wild-type sequence" of a gene is the polynucleotide sequence that comprises the genetic locus corresponding to the gene, e.g., all regulatory and open-reading frame coding sequences required for expression of a completely functional gene product as they are present in the wild-type genome of an organism. The native sequence of a gene can include, for example, transcriptional promoter sequences, translation enhancing sequences, introns, exons, and poly-A processing signal sites. It is noted that in the general population, wild-type genes may include multiple prevalent versions that contain alterations in sequence relative to each other and yet do not cause a discernible pathological effect. These variations are designated "polymorphisms" or "allelic variations".

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide.

By "vector" is meant any genetic element, such as a plasmid, phage, transposon, cosmid, chromosome, virus etc., which is capable of transferring gene sequences to target cells. Generally, a vector is capable of replication when associated with the proper control elements. Thus, the term includes cloning an expression vehicles, as well as viral vectors and integrating vectors.

As used herein, the term "expression cassette" refers to a molecule comprising at least one coding sequence operably linked to a control sequence which includes all nucleotide sequences required for the transcription of cloned copies of the coding sequence and the translation of the mRNAs in an appropriate host cell. Such expression cassettes can be used to express eukaryotic genes in a variety of hosts such as bacteria, blue-green algae, plant cells, yeast cells, insect cells and animal cells. Under the invention, expression cassettes can include, but are not limited to, cloning vectors, specifically designed plasmids, viruses or virus particles. The cassettes may further include an origin of replication for autonomous replication in host cells, selectable markers, various restriction sites, a potential for high copy number and strong promoters.

A cell has been "transformed" by an exogenous polynucleotide when the polynucleotide has been introduced inside the cell. The exogenous polynucleotide may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cells containing the exogenous DNA.

"Recombinant host cells," "host cells," "cells," "cell lines," "cell cultures," and other such terms denoting prokaryotic microorganisms or eukaryotic cell lines cultured as unicellular entities, are used interchangeably, and refer to cells which can be, or have been, used as recipients for recombinant vectors or other transfer DNA, and include the progeny of the original cell which has been transfected. It is understood that ht progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

The term "dwf4 polynucleotide" refers to a polynucleotide derived from the dwf4 gene. The gene encodes the protein referred to herein as DWF4. DWF4 is a cytochrome P450 cytochrome P450 that mediates multiple 22α-hydroxylation steps in brassinosteriod biosynthesis (see, FIG. 1). The dwf4 polynucleotide sequence and corresponding amino acid sequence are shown in FIGS. 10 and 11 (SEQ ID NO:1, SEQ ID NO:2 and GenBank accession No. AF044216). As shown in FIG. 10, the dwf4 coding sequence spans the region from nucleotide positions 3203 to 6110 and the upstream 5' UTR, including the promoter region, spans nucleotide positions 1 to 3202. A functional 1.1 kb control element is also described in the Examples. A 3' UTR spans nucleotide positions 6111 to approximately 6468 of SEQ ID NO:1. The term as used herein encompasses a polynucleotide including a native sequence depicted in FIG. 10, as well as modifications and fragments thereof.

The term encompasses alterations to the polynucleotide sequence, so long as the alteration results in a plant displaying one or more dwf4 phenotypic traits (described below) when the polynucleotide is expressed in a plant. Such modifications typically include deletions, additions and substitutions, to the native dwf4I sequence, so long as the mutation results in a plant displaying a dwf4 phenotype as defined below. These modifications may be deliberate, as through site-directed mutagenesis, or may be accidental, such as through mutations of plants which express the dwf4 polynucleotide or errors due to PCR amplification. The term encompasses expressed allelic variants of the wild-type dwf4 sequence which may occur by normal genetic variation or are produced by genetic engineering methods and which result in a detectable change in the wild-type dwf4 phenotype.

The term "dwf4 phenotype" as used herein refers to any microscopic or macroscopic change in structure or morphology of a plant, such as a transgenic plant, as well as biochemical differences, which are characteristic of a dwf4 plant, compared to a progenitor, wild-type plant cultivated under the same conditions. Generally, morphological differences include multiple short stems, short rounded leaves, loss of fertility due to reduced stamen length, and delayed development. Dark-grown dwf4 seedlings possess short hypocotyls, open cotyledons, and developing leaves. The height of such plants will typically be 75% or less of the wild-type plant, more typically 50% or less of the wild-type plant, and even more typically 25% or less of the wild-type plant, or any integer in between. Additional phenotypic morphological attributes of the dwf4 mutant are summarized in Table 1 of the examples. Biochemically, dwf4 hypocotyls are converted to wild-type length with the application of BL.

A "polypeptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein. Full-length proteins, analogs, mutants and fragments thereof are encompassed by the definition. The terms also include postexpression modifications of the polypeptide, for example, glycosylation, acetylation, phosphorylation and the like. Furthermore, as ionizable amino and carboxyl groups are present in the molecule, a particular polypeptide may be obtained as an acidic or basic salt, or in neutral form. A polypeptide may be obtained directly from the source organism, or may be recombinantly or synthetically produced (see further below).

A "DWF4" polypeptide is a polypeptide as defined above, which is derived from a 22α-hydroxylase that functions in the brassinolide (BL) biosynthetic pathway (see, FIG. 1). The native sequence of full-length DWF4 is shown in FIG. 11 (SEQ ID NO:2). However, the term encompasses mutants and fragments of the native sequence so long as the protein functions for its intended purpose.

Te term "DWF4 analog" refers to derivatives of DWF4, or fragments of such derivatives, that retain desired function, e.g., as measured in assays as described further below. In general, the term "analog" refers to compounds having a native polypeptide sequence and structure with one or more amino acid additions, substitutions (generally conservative in nature) and/or deletions, relative to the native molecule, so long as the modifications do not destroy desired activity.

Preferably, the analog has at least the same activity as the native molecule. Methods for making polypeptide analogs are known in the art and are described further below.

Particularly preferred analogs include substitutions that are conservative in nature, i.e., those substations that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, praline, phenylalanine, methionine, tryptophan; and (4) uncharged polar—glycine, asparagines, glutamine, cysteine, serine threonine, tyrosine. Phenylalanine, tryptophan and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. It is to be understood that the terms include the various sequence polymorphisms that exist, wherein amino acid substitutions in the protein sequence do not affect the essential functions of the protein.

By "purified" and "isolated" is meant, when referring to a polypeptide or polynucleotide, that the molecule is separate and discrete from the whole organism with which the molecule is found in nature; or devoid, in whole or part, of sequences normally associated with it in nature; or a sequence, as it exists in nature, but having heterologous sequences (as defined below) in association therewith. It is to be understood that the term "isolated" with reference to a polynucleotide intends that the polynucleotide is separate and discrete from the chromosome from which the polynucleotide may derive. The term "purified" as used herein preferably means at least 75% by weight, more preferably at least 85% by weight, more preferably still at least 95% by weight, and most preferably at least 98% by weight, of biological macromolecules of the same type are present. An "isolated polynucleotide which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

By "fragment" is intended a polypeptide or polynucleotide consisting of only a part of the intact sequence and structure of the reference polypeptide or polynucleotide, respectively. The fragment can include a 3' or C-terminal deletion or a 5' or N-terminal deletion, or even an internal deletion, of the native molecule. A polynucleotide fragment of a dwf4 sequence will generally include at least about 15 contiguous bases of the molecule in question, more preferably 18-25 contiguous bases, even more preferably 30-50 or more contiguous bases of the dwf4 molecule, or any integer between 15 bases and the full-length sequence of the molecule. Fragments which provide at lest one dwf4 phenotype as defined above are useful in the production of transgenic plants. Fragments are also useful as oligonucleotide probes, to find additional dwf4 sequences.

Similarly, a polypeptide fragment of a DWF4 molecule will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length DWF4 molecule, or any integer between 10 amino acids and the full-length sequence of the molecule. Such fragments are useful for the production of antibodies and the like.

By "transgenic plant" is meant a plant into which one or more exogenous polynucleotides have been introduced. Examples of means by which this an be accomplished are described below, and include *Agrobacterium*-mediated transformation, biolistic methods, electroporation, and the like. In the context of the present invention, the transgenic plant contains a polynucleotide which is not normally present in the corresponding wild-type plant and which confers at least one dwf4 phenotypic trait to the plant. The transgenic plant therefore exhibits altered structure, morphology or biochemistry as compared with a progenitor plant which does not contain the transgene, when the transgenic plant and the progenitor plant are cultivated under similar or equivalent growth conditions. Such a plant containing the exogenous polynucleotide is referred to here as an $R_1$ generation transgenic plant. Transgenic plants may also arise from sexual cross or by selfing of transgenic plants into which exogenous polynucleotides have been introduced. Such a plant containing the exogenous nucleic acid is also referred to here as an $R_1$ generation transgenic plant. Transgenic plants which arise from a sexual cross with another parent line or by selfing are "descendants or the progeny" of a $R_1$ plant and are generally called $F_n$ plants or $S_n$ plants respectively, n meaning the number of generations.

General Overview

In this report, we present morphological, biochemical, and molecular analysis of a novel gene, dwf4, isolated from *Arabidopsis*. Morphologically, dwf4 plants display a dramatic reduction in the length of many different organs examined, and this size reduction is attributable to a defect in cell elongation. Biochemically, dwf4 hypocotyls were converted completely to wild-type length with the application of BL, suggesting a deficiency in BRs. In agreement with this, BR intermediate feeding analysis, indicated that dwf4 encodes a cytochrome P450 that mediates multiple $22\alpha$-hydroxylation steps in brassinosteriod biosynthesis. Sequencing of the dwf4 locus and analysis of the protein product are described.

The molecules of the present invention are therefore useful in the production of transgenic plants which display at least one dwf4 phenotype, so that the resulting plants have altered structure or morphology. The present invention particularly provides for altered structure or morphology. The present invention particularly provides for altered structure or morphology such as reduced cell length, extended flowering periods increased size of leaves or fruit, increased branching, increased seed production and altered sterol composition relative wild-type plants. The DWF4 polypeptides can be expressed to engineer a plant with desirable properties. The engineering is accomplished by transforming plants with nucleic acid constructs described herein which ay also comprise promoters and secretion signal peptides. The transformed plants or their progenies are screened for plants that express the desired polypeptide.

Engineered plants exhibiting the desired altered structure or morphology can be used in plant breeding or directly in agricultural production or industrial applications. Plants having the altered polypeptide can be crossed with other altered plants engineered with alterations in other growth modulation enzymes, proteins or polypeptides to produce lines with even further enhanced altered structural morphology characteristics compared to the parents or progenitor plants.

Isolation of Nucleic Acid Sequences from Plants

The isolation of dwf4 sequences from the polynucleotides of the invention may be accomplished by a number of techniques. For instance, oligonucleotide probes based on the sequences disclosed here can be used to identify the desired gene in a cDNA or genomic DNA library from a desired plant species. To construct genomic libraries, large segments f genomic DNA are generated by random fragmentation, e.g. using restriction endonucleases, and are ligated with vector DNA to form concatemers that can be packaged into the appropriate vector. To prepare a library of tissue-specific cDNAs, mRNA is isolated from tissues and a cDNA library which contains the gene transcripts is prepared form the mRNA.

The cDNA or genomic library can then be screened using a probe based upon the sequence of a cloned gene such as the polynucleotides disclosed here. Probes may be used to hybridize with genomic DNA or cDNA sequences to isolate homologous genes in the same or different plant species. Alternatively, the nucleic acids of interest can be amplified from nucleic acid samples using amplification techniques. For instance, polymerase chain reaction (PCR) technology to amplify the sequences of the genes directly from mRNA, from cDNA, from genomic libraries or cDNA libraries. PCR® and other in vitro amplification methods may also be useful, for example, to cone nucleic acid sequences that code for proteins to be expressed, to make nucleic acids to use as probes for detecting the presence of the desired mRNA in samples, for nucleic acid sequencing, or for other purposes.

Appropriate primers and probes for identifying dwf4-specific genes from plant tissues are generated form comparisons of the sequences provided herein. For a general overview of PCR see Innis et al. eds *PCR protocols: A Guide to Methods and Applications*, Academic Press, San Diego (1990). Appropriate primers for this invention include, for instance, those primers described in the Examples and Sequence Listings, as well as other primers derived from the dwf4 sequences disclosed herein. Suitable amplifications conditions may be readily determined by one of skill in the art in view of the teachings herein, for example, including reaction components and amplification conditions as follows: 10 mM Tris-HCl, pH 8.3, 50 mM potassium chloride, 1.5 mM magnesium chloride, 0.001% gelatin, 200 µM dATP, 200 µM dCTP, 200 µM dGTP, 200 µM dTTP, 0.4 µM primers, and 100 units per mL Taq polymerase; 96° C. for 3 min., 30 cycles of 96° C. for 45 seconds, 50° C. for 60 seconds, 72° C. for 60 seconds, followed by 72° C. for 5 min.

Polynucleotides may also be synthesized by well-known techniques as described in the technical literature. See, e.g., Carruthers, et al. (1982) *Cold Spring Harbor Symp. Quant. Biol.* 47:411-418, and Adams, et al. (1983) *J. Am. Chem. Soc.* 105:661. Double stranded DNA fragments may then be obtained either by synthesizing the complementary strand and annealing the strands together under appropriate conditions, or by adding the complementary strand using DNA polymerase with an appropriate primer sequence.

The polynucleotides of the present invention may also be used to isolate or create other mutant cell gene alleles. Mutagenesis consists primarily of site-directed mutagenesis followed by phenotypic testing of the altered gene product. Some of the more commonly employed site-directed mutagenesis protocols take advantage of vectors that can provide single stranded as well as double stranded DNA, as needed. Generally, the mutagenesis protocol with such vectors is as follows. A mutagenic primer, i.e., a primer complementary to the sequence to be changed, but consisting of one or a small number of altered, added, or deleted bases, is synthesized. The primer is extended in vitro by a DNA polymerase and, after some additional manipulations, the now double-stranded DNA is transfected into bacterial cells. Next, by a variety of methods, the desired mutated DNA is identified, and the desired protein is purified from clones containing the mutated sequence. For longer sequences, additional cloning steps are often required because long inserts (longer than 2 kilobases) are unstable in those vectors. Protocols are known to one skilled in the art and kits for site-directed mutagenesis are widely available from biotechnology supply companies, for example from Amersham Life Science, Inc. (Arlington Heights, Ill.) and Stratagene Cloning Systems (La Jolla, Calif.).

Control Elements

Regulatory regions can be isolated from the dwf4 gene and used in recombinant constructs for modulating the expression of the dwf4 gene or a heterologous gene in vitro and/or in vivo. As shown in FIG. 10, the coding region of the dwf4 gene (designated by the open bar) begins at nucleotide position 1133. The region of the gene spanning nucleotide positions 990-1132 of FIG. 10 includes the dwf4 promoter. This region may be used in its entirety or fragments of the region may be isolated which provide the ability to direct expression of a coding sequence linked thereto.

Thus, promoters can be identified by analyzing the 5' sequences of a genomic clone corresponding to the dwf4-specific genes described here. Sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. IN plants, further upstream from the TATA box, at positions −80 to −100, there is typically a promoter element with a series of adenines surrounding the trinucleotide G (or T) N G. (See, J. Messing et al., in *Genetic Engineering in Plants*, pp. 221-227 (Kosage, Meredith and Hollaender, eds. (1983)). Methods for identifying and characterizing promoter regions in plant genomic DNA are described, for example, in Jordano et al. (1989) *Plant Cell* 1:855-866; Bustos et al (1989) *Plant Cell* 1:839-854; Green et al. (1988) *EMBO J.* 7:4035-4044; Meier et al. (1991) *Plant Cell* 3:309-316; and Zhang et al (1996) *Plant Physiology* 110:1069-1079.

Additionally, the promoter region may include nucleotide substitutions, insertions, or deletions that do not substantially affect the binding of relevant DNA binding proteins and hence the promoter function. It may, at times, be desirable to decrease the binding of relevant DNA binding proteins to "silence" or "down-regulate" a promoter, or conversely to increase the binding of relevant DNA binding proteins to "enhance" or "up-regulate" a promoter. In such instances, the nucleotide sequence of the promoter region may be modified by, e.g., inserting additional nucleotides, changing the identify of relevant nucleotides, including use of chemically-modified bases, or by deleting one or more nucleotides.

Promoter function can be assayed by methods known in the art, preferably by measuring activity of a reporter gene operatively linked to the sequence being tested for promoter function. Examples of reporter genes include those encoding luciferase, green fluorescent protein, GUS, neo, cat and bar.

Polynucleotides comprising untranslated (UTR) sequences and introns/exon junctions are also within the scope of the invention. UTR sequences include introns and 5' or 3' untranslated regions (5' UTRs or 3' UTRs). As shown in FIGS. 2 and 10, the dwf4 gene sequence includes eight exons and seven introns. These portions of the dwf4 gene especially UTRs, can have regulatory functions related to, for example, translation rate and mRNA stability. Thus, these portions of the gene can be isolated for use as elements of gene constructs for expression of polynucleotides encoding desired polypeptides. The 5' control element region of dwf4 extends from nucleotides 1 through 3202 of SEQ ID NO:1. Further, as described in Example 11, a 1.1 kb portion of this region that is directly upstream of the translation initiation site contains elements necessary for transcriptional control of dwf4. In contrast, a 280 by fragment of the dwf4 control element region that includes the TATA-like region does not appear to contain all of the necessary transcriptional control elements (see, Example 11).

Introns of genomic DNA segments may also have regulatory functions. Sometimes promoter elements, especially transcription enhancer or suppressor elements, are found within introns. Also, elements related to stability of heteronuclear RNA and efficiency of transport to the cytoplasm for translation can be found in introns elements. Thus, these segments can also find use as elements of expression vectors intended for use to transform plants.

The introns, UTR sequences and introns/exon junctions can vary from the native sequence. Such changes from those sequences preferably will not affect the regulatory activity of the UTRs or introns or introns/exon junction sequences on expression, transcription, or translation. However, in some instances, down-regulation of such activity may be desired to modulate traits or phenotypic or in vitro activity.

Use of Nucleic Acids of the Invention to Inhibit Gene Expression

The isolated sequences prepared as described herein, can be used to prepare expression cassettes useful in a number of techniques. For example, expression cassettes of the invention can be used to suppress (underexpress) endogenous dwf4 gene expression. Inhibiting expression can be useful, for instance, in suppressing the phenotype (e.g., dwarf appearance, 22α-hydroxylase activity) exhibited by dwf4 plants. Further, the inhibitory polynucleotides of the present invention can also be used in combination with overexpressing constructs described below, for example, using suitable tissue-specific promoters linked to polynucleotides described herein. In this way, the polynucleotides can be used to promote dwf4 phenotypes (e.g., activity) in selected tissue and, at the same time, inhibit dwf4 phenotypes (e.g., activity) in different tissue(s).

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al. (1988) *Proc. Nat. Acad. Sci. USA* 85:8805-8809, and Hiatt et al., U.S. Pat. No. 4,801,340.

The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequenced. Furthermore, the introduced sequence need not have the same introns or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred. It is to be understood that any integer between the above-recited ranges is intended to be captured herein.

Catalytic RNA molecules or ribozymes can also be used to inhibit expression of dwf4 genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either along (viroid RNAs) or with a helper virus (satellite RNAs). Examples include RNAs from avocado sunblotch viroid and the satellite RNAs from tobacco ringspot virus, Lucerne transient streak virus, velvet tobacco mottle virus, *solanum* nodiflorum mottle virus and subterranean clover mottle virus. The design and use of target RNA-specific ribozymes is described in Haseloff et al (1988) *Nature* 334:585-591.

Another method of suppression is sense suppression. Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al. (1990) *The Plant Cell* 2:279-289 and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only introns or untranslated sequences homologous to sequences present in the primary transcript of the endogenous sequence. The introduced sequence generally will be substantially identical to the endogenous sequence intended to be repressed. This minimal identify will typically be greater than about 50%-65%, but a higher identify might exert a more effective repression of expression of the endogenous sequences. Substantially greater identity of more than about 80% is preferred, though about 95% to absolute identity would be most preferred. It is to be understood that any integer between the above-recited ranges is intended to be captured herein. As with antisense regulation, the effect should apply to any other proteins within a family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same introns or exon pattern, and identity of non-coding segments will be equally effective. Normally, a sequence of the size ranges noted above for antisense regulation is used.

Use of Nucleic Acids of the Invention to Enhance Gene Expression

In addition to inhibiting certain features of a plant, the polynucleotides of the invention can be used to increase certain features such as extending flowering, producing larger leaves or fruit, producing increased branching and increasing seed production. This can be accomplished by the overexpression of dwf4 polynucleotides.

The exogenous dwf4 polynucleotides do not have to code for exact copies of the endogenous dwf4 proteins. Modified DWF4 protein chains can also be readily designed utilizing various recombinant DNA techniques well known to those skilled in the art and described for instance, in Sambrook et al., supra. Hydroxylamine can also be used to introduce single base mutations into the coding region of the gene (Sikorski et al (1991) *Meth. Enzymol.* 194: 302-318). For example, the chains can vary from the naturally occurring sequence at the primary structure level by amino acid substitutions, additions, deletions, and the like. These modifications can be used in a number of combinations to produce the final modified protein chain.

It will be apparent that the polynucleotides described herein can be used in a variety of combinations. For example, the polynucleotides can be used to produce different phenotypes in the same organism, for instance by using tissue-specific promoters to overexpress a dwf4 polynucleotide in certain tissues (e.g., leaf tissue) while at the same time using tissue-specific promoters to inhibit expression of dwf4 in other tissues. In addition fusion proteins of the polynucleotides described herein with other known polynucleotides (e.g., polynucleotides encoding products involved in the BR pathway) can be constructed and employed to obtain desired phenotypes.

Any of the dwf4 polynucleotides described herein can also be used in standard diagnostic assays, for example, in assays mRNA levels (see, Sambrook et al., supra); as hybridization probes, e.g., in combination with appropriate means, such as a label, for detecting hybridization (see, Sambrook et al., supra); as primers, e.g., for PCR (see, Sambrook et al., supra); attached to solid phase supports and the like.

Preparation of Recombinant Vectors

To use isolated sequences in the above techniques, recombinant DNA vectors suitable for transformation of plant cells are prepared. Techniques for transforming a wide variety of higher plant species are well known and described further below as well as in the technical and scientific literature. See, for example, Weising et al (1988) *Ann. Rev. Genet.* 22:421-377. A DNA sequence coding for the desired polypeptide, for example a cDNA sequence encoding the full length DWF4 protein, will preferably be combined with transcriptional and translational initiation regulatory sequences which will direct the transcription of the sequence form the gene in the intended tissues of the transgenic plant.

Such regulatory elements include but are not limited to the promoters derived form the genome of plant cells (e.g., heat shock promoters such as soybean hsp17.5-E or hsp17.3-B (Gurley et al. (1986) *Mol. Cell. Biol.* 6:559-565); the promoter for the small subunit of RUBISCO (Coruzzi et al. (1984) *EMBO J.* 3:1671-1680; Broglie et al (1984) *Science* 224:838-843); the promoter for the chlorophyll a/b binding protein) or from plant viruses viral promoters such as the 35S RNA and 19S RNA promoters of CaMV (Brisson et al. (1984) *Nature* 310:511-514), or the coat protein promoter of TMV (Takamatsu et al. (1987) *EMBO J.* 6:307-311), cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, heat shock promoters (e.g., as described above) and the promoters of the yeast alpha-mating factors.

In construction of recombinant expression cassettes of the invention, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the T-DNA mannopine synthetase promoter (e.g., the 1'- or 2' promoter derived from T-DNA of *Agrobacterium tumafaciens*), and other transcription initiation regions form various plant genes known to those of skill.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers such as tissue- or developmental-specific promoter, such as, but not limited to the dwf4 promoter, the CHS promoter, the PATATIN promoter, etc. The tissue specific E8 promoter from tomato is particularly useful for direction gene expression so that a desired gene product is located in fruits.

Other suitable promoters include those from genes encoding embryonic storage proteins. Examples of environmental conditions that may affect transcription by inducible promoters include anaerobic conditions, elevated temperature, or the presence of light. If proper polypeptide expression is desired, a polyadenylation region at the 3'-end of the coding region should be included. The polyadenylation region can be derived from the natural gene, from a variety of other plant genes, or from T-DNA. In addition, the promoter itself can be derived from the dwf4 gene, as described above.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

Production of Transgenic Plants

DNA constructs of the invention may be introduced into the genome of the desired plant host by a variety of conventional techniques. For reviews of such techniques see, for example, Weissbach & Weissbach *Methods for Plant Molecular Biology* (1988, Academic Press, N. Y.) Section VIII, pp. 421-463; and Grierson & Corey, *Plant Molecular Biology* (1988, 2d Ed.) Blackie, London, Ch. 7-9. For example, the DNA construct may be introduced directly into the genomic DNA of the plant cell using techniques such as electroporation and microinjection of plant cell protoplasts, or the DNA constructs can be introduced directly to plant tissue using biolistic methods; such as DNA particle bombardment (see, e.g., Klein et al (1987) *Nature* 327:70-73). Alternatively, the DNA constructs may be combined with suitable T-DNA flanking regions and introduced into a conventional *Agrobacterium tumefaciens* host vector. *Agrobacterium tumefaciens*-mediated transformation techniques, including disarming and use of binary vectors, are well describe din the scientific literature. See, for example Horsch et al (1984) *Science* 233:

496-498, and Fraley et al (1983) *Proc. Nat'l Acad. Sci. USA* 80:4803. The virulence functions of the *Agrobacterium tumefaciens* host will direct the insertion of the construct and adjacent marker into the plant cell DNA when the cell is infected by the bacteria using binary T DNA vector (Bevan (1984) *Nuc. Acid Res.* 12:8711-8721) or the co-cultivation procedure (Horsch et al (1985) *Science* 227:1229-1231). Generally, the *Agrobacterium* transformation system is used to engineer dicotyledonous plants (Bevan et al (1982) *Ann. Rev. Genet.* 16:357-384; Rogers et al (1986) *Methods Enzymol.* 118:627-641). The *Agrobacterium* transformation system may also be used to transform, as well as transfer, DNA to monocotyledonous plants and plant cells. (see Hernalsteen et al (1984) *EMBO J* 3:3039-3041; Hooykass-Van Slogteren et al (1984) *Nature* 311:763-764; Grimsley et al (1987) *Nature* 325:1677-179; Boulton et al (1989) *Plant Mol. Biol.* 12:31-40.; and Gould et al (1991) *Plant Physiol.* 95:426-434).

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J.* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide mediated DNA uptake (Kaeppler et al. (1990) *Plant Cell Reporter* 9:415-418), and microprojectile bombardment (see Klein et al. 1988) *Proc. Nat. Acad. Sci. USA* 85:4305-4309; and Gordon-Kamm et al. (1990) *Plant Cell* 2:603-618).

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration form cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts* pp. 21-73, CRC Press, Boca Raton, 1985. Regeneration can also be obtained from plant callus, explants, organs, pollens, embryos or parts thereof. Such regeneration techniques are described generally in Klee et al (1987) *Ann. Rev. of Plant Phys.* 38:467-486.

The nucleic acids of the invention can be used to confer desired traits on essentially any plant. A wide variety of plants and plant cell systems may be engineered for the desired physiological and agronomic characteristics described herein using the nucleic acid constructs of the present invention and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the invention has use over a broad range of plants, including, but not limited to, species form the genera Asparagus, *Avena, Brassica, Citrus, Citrullus, Capsicum, Cucurbita, Daucus,* glycine, *Hordeum, Lactuca, Lycopersicon, Malus, Manihot, Nicotiana, Oryza, Persea, Pisum, Pyrus, Prunus, Raphanus, Secale, Solanum, Sorghum, Triticum, Vitis, Vigna,* and *Zea.*

One of skill in the art will recognize that after the expression cassette is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection may be performed by growing the engineered plant material on media containing an inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or Cl genes) that may be present on the recombinant nucleic acid constructs of the present invention. Such selection and screening methodologies are well known to those skilled in the art.

Physical and biochemical methods also may be used to identify plant or plant cell transformants containing the gene constructs of the present invention. These methods include but are not limited to: 1) Southern analysis or PCR amplification for detecting and determining the structure of the recombinant DNA insert; 2) Northern blot, 51 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods of this invention can be observed by, for example, northern blots of the RNA (e.g., mRNA) isolated form the tissues of interest. Typically, if the amount of mRNA has increased, it can be assumed that the endogenous dwf4 gene is being expressed at a greater rate than before. Other methods of measuring DWF4 activity can be used. For example, cell length can be measured at specific times. Because dwf4 affects the BR biosynthetic pathway, an assay that measures the amount of BL can also be used. Such assays are known in the art. Different types of enzymatic assays can be used, depending on the substrate used and the method of detecting the increase or decrease of a reaction product or by-product. IN addition, the levels of DWF4 protein expressed can be measured immunochemically, i.e., ELISA, RIA, EIA and other antibody based assays well known to those of skill in the art, by electrophoretic detection assays (either with staining or western blotting), and sterol (BL) detection assays.

The transgene may be selectively expressed in some tissues of the plant or at some developmental stages, or the transgene may be expressed in substantially all plant tissues, substantially along its entire life cycle. However, any combinatorial expression mode is also applicable.

The present invention also encompasses seeds of the transgenic plants described above wherein the seed has the transgene or gene construct. The present invention further encompasses the progeny, clones, cell liens or cells of the transgenic plants described above wherein said progeny, clone, cell line or cell has the transgene or gene construct.

Polypeptides

The present invention also includes DWF4 polypeptides, including such polypeptides as a fusion, or chimeric protein product (comprising the protein, fragment, analogue, mutant or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art.

As noted above, DWF4 phenotype includes any macroscopic, microscopic or biochemical changes which are characteristic of over- or under-expression of dwf4. Thus, DWF4 polypeptide phenotype (e.g., activities) can include any activity that is exhibited by the native DWF4 polypeptide including, for example, in vitro, in vivo, biological, enzymatic, immunological, substrate binding activities, etc. Non-limiting examples of DWF4 activities include:

(a) activities displayed by other heme-thiolate enzymes;

(b) characteristic Soret absorption peak at 40 nm when the substrate-bound reduced form is exposed to the lights (see, e.g., Jefcoate et al., infra);

(c) hydroxylation of various substrates via monooxygenase activity, which utilizes molecular oxygen and reducing equivalents from NAD(P)H;

(d) oxidation, dealkylation, deaminoation, dehalogenation, and sulfoxide formation that are involved in a variety of biological events in plants and animals (e.g., catabolism, anabolism, and xenobiotic activities);

(e) recognition of at two substrates: campestanol (CN) and 6-deoxocastasterone (6-deoxoCS);

(f) 22α-hydroxylase activity;

(g) DWF-4 phenotypic activities such as modulation of cell length, periods of flowering, branching, seed production, leaf size, and sterol composition in a plant;

(h) regulation of gibberellic acid, cytokinins and/or auxin;

(i) induce resistance to plant pathogens (see, e.g., U.S. Pat. No. 5,952,545);

(j) accelerating growth at low temperatures; and (k) accelerating growth in dark conditions.

A DWF4 analog, whether a derivative, fragment or fusion of native DWF4 polypeptides, is capable of at least one DWF4 activity. Preferably, the analogs exhibit at least 60% of the activity of the native protein, more preferably at least 70% and even more preferably at least 80%, 85%, 90% or 95% of at least one activity of the native protein.

Further, such analogs exhibit some sequence identity to the native DWF4 polypeptide sequence. Preferably, the variants will exhibit at least 35%, more preferably at least 59%, even more preferably 75% or 80% sequence identity, even more preferably 85% sequence identity, even more preferably, at least 90% sequence identity.

DWF4 analogs can include derivatives with increased or decreased activities as compared to the native DWF4 polypeptides. Such derivatives can include changes within the domains, motifs and/or consensus regions of the native DWF4 polypeptide, which are described in detail in Example 3.

Once class of analogs is those polypeptide sequences that differ from the native DWF4 polypeptide by changes, insertions, deletions, or substitution; at positions flanking the domain and/or conserved residues. For example, an analog can comprise (1) the domains of a DWF4 polypeptide and/or (2) residues conserved between the DWF4 polypeptide and other cytochrome P450 proteins, for example as shown in FIG. 3 and described in Example 3.

Another class of analogs includes those that comprise a DWF4 polypeptide sequence that differs from the native sequence in the domain of interest or conserved residues by a conservative substitution. For example, an analog that exhibits increased sterol binding can have optimized sterol binding domain sequences that differ from the native sequence.

Yet another class of analogs includes those that lack one of the in vitro activities or structural features of the native DWF4 polypeptides, for example, dominant negative mutants or analogs that comprise a heme-binding domain but contain an inactivated steroid binding domain.

DWF4 polypeptide fragments can comprise sequences from the native or analog sequences, for example fragments comprising one or more of the following P450 domains or regions: A, B, C, D, anchor binding, and proline rich. Such domains and regions are shown in FIGS. 2B, 3 and described in Example 3.

Fusion polypeptides comprising DWF4 polypeptides (e.g., native, analogs, or fragments thereof) can also be constructed. Non-limiting examples of other polypeptides that can be used in fusion proteins include chimeras of DWF4 polypeptides and fragments thereof; and P450 polypeptides or fragments thereof, such as those shown in FIG. 3.

In addition, DWF4 polypeptides, derivatives (including fragments and chimeric proteins), mutants and analogues can be chemically synthesized. See, e.g., Clark-Lewis et al. (1991) *Biochem.* 30:3128-3135 and Merrifield (1963) *J. Amer. Chem. Soc.* 85:2149-2156. For example, DWF4, derivatives, mutants and analogues can be synthesized by solid phase techniques, cleaved from the resin, and purified by preparative high performance liquid chromatography (e.g., see Creighton, 1983, Proteins, Structures and Molecular Principles, W.H. Freeman and Co. N.Y., pp. 50-60). DWF4, derivatives and analogues that are proteins can also be synthesized by use of a peptide synthesizer. The composition of the synthetic peptides may be confirmed by amino acid analysis or sequencing (e.g., the Edman degradation procedure; see Creighton, 1983, Proteins, Structures and Molecular Principles, W.H. Freeman and Co., N.Y., pp. 34-49).

Further, the dwf4 polynucleotides and DWF4 polypeptides described herein can be used to generate antibodies that specifically recognize and bind to the protein products of the dwf4 polynucleotides. (See, Harlow and Lane, eds. (1988) "Antibodies: A Laboratory Manual"). The DWF4 polypeptides and antibodies therefore can also be used in standard diagnostic assays, for example, radioimmunoassay, ELISA (enzyme linked immunoradiometric assays), "sandwich" immunoassays, immunoradiometric assays, in situ immunoassay, western blot analysis, immunoprecipitation assays, immunofluorescent assays and PAGE-SDS.

Applications

The present invention finds use in various applications, for example, including but not limited to those listed above.

The polynucleotide sequences may additionally be used to isolate mutant dwf4 gene alleles. Such mutant alleles may be isolated from plant species either known or proposed to have a genotype which contributes to altered plant morphology. Additionally, such plant dwf4 gene sequences can be used to detect plant dwf4 gene regulatory (e.g., promoter or promoter/enhancer) defects which can affect plant growth.

The molecules of the present invention can be used to provide plants with increased seed and/or fruit production, extended flowing periods and increased branching. The molecules described herein can be used to alter the sterol composition of a plant, thereby increasing or reducing cholesterol content in the plant. A still further utility of the molecules of the present invention is to provide a tool for studying the biosynthesis of brassinosteriods, both in vitro and in vivo.

The dwf4 gene of the invention also has utility as a transgene encoding a cytochrome P450 protein that mediates multiple 22α hydroxylation steps in brassinosteriod biosynthesis which results in a transgenic plant to alter plant structure or morphology. The dwf4 gene also has utility for encoding the DWF4 protein in recombinant vectors which may be inserted into host cells to express the DWF4 protein. Further, the dwf4 polynucleotides of the invention may be utilized (1) as nucleic acid probes to screen nucleic acid libraries to identify other enzymatic genes or mutants; (2) as nucleic acid sequences to be mutated or modified to produce DWF4 protein variants or derivatives; (3) as nucleic acids encoding 22α-hydroxylase in molecular biology techniques or industrial applications commonly known to those skilled in the art.

The dwf4 nucleic acid molecules may be used to design plant dwf4 antisense molecules, useful, for example, in plant dwf4 gene regulation or as antisense primers in amplification reactions of plant dwf4 gene nucleic acid sequences. With respect to plant dwf4 gene regulation, such techniques can be used to regulate, for example, plant growth, development or gene expression. Further, such sequences may be used as part of ribozyme and/or triple helix sequences, also useful for dwf4 gene regulation.

The dwf4 control element (e.g., promoter) of the present invention may be utilized as a plant promoter to express any protein, polypeptide or peptide of interest in a transgenic plant. In particular, the dwf4 promoter may be used to express a protein involve din brassinosteriod biosynthesis.

The *Arabidopsis* DWF4 protein of the invention can be used in any biochemical applications (experimental or industrial) where 22α-hydroxylase activity is desired, for example, but not limited to, regulation of BL synthesis, regulation of other sterol synthesis, modification of elongating plant structures, and experimental or industrial biochemical applications known to those skilled in the art.

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Materials and Methods

A. Plant Growth Conditions

The conditions used for plant growth were essentially as described previously (Feldmann (1991) *Plant J.* 1:71-82; Forsthoefel et al. (1992) *Aust. J. Plant Physiol.* 19:353-366), except that agar-solidified medium contained 0.5% sucrose. Seedlings up to 2 weeks of age (6 weeks of age for dark-growth experiments) were grown on 0.9% agar-solidified medium containing 1×Murashige and Skoog 1962 salts (Murashige, T., and Skoog, F. (1962) *Physiol. Plant,* 15:473-497) and 0.5% sucrose (w/v) and cold treated (4° C.) for 2 days in the dark before transfer to the light (24 hr light; 80 μmol $M^{-2}$ $sec^{-1}$); older plants were grown in potting soil. The plates were sealed with Parafilm (American National Can Co., Chicago, Ill.) for the entire experiment. For nucleic acid extraction, genetic analysis, and other experiments in which mature plants were required, seeds were sown on Metromix 350 (Grace Sierra, Milpitas, Calif.) presoaked with distilled water. The pots were covered with plastic wrap and cold treated (4° C.) for two days before transfer to a growth chamber (16:8, light [240 μmol $m^{-2}$ $sec^{-1}$]:dark; 22 and 21° C., respectively, and 75 to 90% humidity). The plastic wrap was removed 5 days after germination, and the pots were subirrigated in distilled water as required. Germination of seeds for dark growth experiments was induced by overnight exposure of the seeds to light immediately after removing the plates from incubation at 4° C. The dwf4-1 and dwf4-2 mutations were in the *Arabidopsis thaliana* ecotype Wassilewskija (Ws-2) background; the dwf4-3 and dwf4-4 mutations were in the Enkheim (En-2) background.

B. Analytical Methods

Protoplasts were obtained by overnight incubation of sliced leaves in 0.1% cellulysin, 0.1% driselase, 0.1% macerase (Calbiochem, San Diego, Calif.) in 125 mM Mes. pH 5.8, 0.5 M mannitol, and 7 mM CaCl2 (Galbraith et al. (1992) *Planta* 186:324-326. Immediately before observation, chloroplasts were stained with a solution of 1.5% KI and 1% $I_2$. Measurements were performed as described for tissue sections, and plane areas were calculated according to the formula $A=\pi r^2$.

Chlorophyll determinations were performed from 2-week-old soil-grown plants. Green tissue was weighed, frozen in liquid nitrogen, and extracted in dim light with 80% acetone in the presence of a mixture of equal parts sand, $NaHCO_3$, and $Na_2SO_4$. After brief centrifugation, the supernatant was collected and the extraction was repeated twice, pooling the supernatants from each sample. Chlorophylls a and b were measured spectrophotometrically, as described in Chory et al. (1991), supra.

C. Growth Signal Response Measurements

Gibberellic acid (GA) response was assayed on plants grown individually in 5.7-cm pots. Once inflorescences reached 1 to 2 mm in height, they were sprayed weekly with 1 mM GA3 (Sigma). Control plants were sprayed with water. One week after the third spraying, plants were collected, and the length of the main stem was measured between the top of the rosette and the base of the most distal pedicel; 13 to 18 plants of each line were measured per treatment. Auxin response was tested by growing seedlings for 10 days under 16 hr of light on vertically oriented agar plates containing various concentrations of 2,4-D (Gibco, Grand Island, N.Y.). Genetic interaction with the hy2 mutation was tested by growing seedlings under continuous light for 7 days. Brassinolide (BL) response was determined in liquid culture, as described by Clouse et al. (1993) supra, except that three or four seedlings were grown in each well of a 24-well culture plate for 7 days. Measurements were taken for 10 to 20 seedlings for each genotype and condition, under a dissection microscope fitted with an ocular micrometer.

D. Microscopy

Tissues were fixed in 2% glutaraldehyde and 0.05 M sodium cacodylate, pH 6.9, for 2 hr at room temperature or overnight at 4° C., followed by three washes in buffer. For light microscopy, 1% safranin was included in the first wash, and embedding was performed in Paraplast Plus (Oxford Labware, St. Louis, Mo.). Ten-millimeter sections from five individual plants per line were analyzed and photographed, and cell measurements were taken using a ruler on 5×7 inch prints. A print of a hemocytometer grid at the same final magnification was used for calibration. At least 25 cells were measured per sample, with a minimum of 150 cells per line. For electron microscopy, the tissues were treated after fixation with 1% tannic acid in buffer for 30 min, washed three times, and postfixed in 1% $OsO_4$ in buffer for 2 hr, followed by five washes and dehydration through an ethanol series. Samples for transmission electron microscopy were embedded in Spurr's resin. Sections (90 nm) were stained with saturated uranyl acetate followed by Reynolds's lead citrate (Reynolds (1963) *J. Cell Biol.* 17:208-212) and examined in a JEOL (Tokyo, Japan) 100-CX instrument. For scanning election microscopy, samples were transferred to Freon 113, critical point dried, and sputter-coated with 30 to 50 nm of gold. Analysis was performed in a microscope (ISI model DS130; Topcon Inc., Paramus, N.J.) with an accelerating voltage of 15 kV. Electron microscopy was performed at the Electron Microscope Facility, Division of Biotechnology, Arizona Research Laboratories, University of Arizona.

Example 2

Isolation of dwf4 Gene

A. Isolation of the DWF4 Gene

The dwf4-1 mutation was identified in a screen of 14,000 transformants of *Arabidopsis* resulting in a dwarfed phenotype similar to dwf1 (Feldmann and Marks(1987) *Mol. Gen. Genet.* 208:1-9; Feldmann et al. (1989) *Science* 243:1351-1354; referred to as diminuto in Takahashi et al. (1995) *Genes Dev.* 9:97-107 and Szekeres et al., supra) and det2 (Azpiroz et al. (1998), supra). Two independent lines were found that segregated for a similar phenotype: both were shorter than dwf1, but their rosette diameter was comparable to that mutant. These dwarfs were also essentially infertile. The most striking aspect of the morphology of these mutants is their similarity to det2 (Chory et al. (1991) *Plant Cell* 3:445-459). For this reason, further analysis was conducted with these lines. After being found to be allelic to each other, both were designated as dwf4.

Dwf4-1 segregated for a single kanamycin resistance marker, and gel blot analysis with DNA from single plants of this family confirmed that the pattern is consistent with a single insert. The dwf4 mutation was subsequently shown to be inherited as a monogenic, recessive Mendelian trait that, in dwf4-1, cosegregates with the dominant kanamycin resistance marker contained in the T-DNA, suggesting that the mutation in this line may be a disrupted, tagged allele. Dwf4-2 also contains a single kanamycin resistance marker, but it failed to cosegregate with the dwarf phenotype. Two additional alleles (dwf4-3 and dwf4-4) were identified among dwarf mutant obtained from the Nottingham *Arabidopsis* Resource Centre (Nottingham, UK; N365 and N374). Unless otherwise indicated, all experiments presented below were performed with dwf4-1.

Standard molecular techniques were performed as described previously (Sambrook et al. 1989). The plant DNA flanking the T-DNA was cloned using the plasmid rescue technique as described by Dilkes and Feldmann (1988) "Cloning genes from T-DNA tagged mutants" in Methods in Molecular Biology: *Arabidopsis* Protocol, J. Martinez-Zapater and J. Salinas, eds (Totowa, N.J.: Humana Press), pp. 339-351. Briefly, dwf4-1 genomic DNA was digested with EcoRI (for the right border) or SalI (for the left border), ligated under conditions to maximize intramolecular events, and instructed into competent *Escherichia coli* cells. The resulting colonies were screened on ampicillin. Five colonies from the left border transformation contained plant DNA flanking the insertion site. The restriction pattern displayed two different types of plant DNA. Three contained a 5.6-kb insert, whereas the other two contained a 1.1-kb insert. This result suggested that the T-DNA insert in dwf4-1 was flanked by two left border sequences. The existence of two left border sequences was confirmed by gel blot analysis with genomic DNA, using the putative plant flanking DNAs as probes. A single wild-type EcoRI fragment was split into two fragments in dwf4-1.

Wild-type genomic clones were isolated from a library made from Ws-2 DNA by using the 5.6-kb fragment as a probe. The library was constructed using X, DASH-II arms (Stratagene, La Jolla, Calif.). Approximately 10,000 primary plaques were screened. Duplicate-filter screening resulted din 12 positives. Restriction mapping of the secondary clones revealed that some contained part of the DWF4 locus. In fact, one of the clones, D4G12-1, contained an intact 13-kb DNA spanning the T-DNA insertion site. The 13-kb insert in D4G12-1 was subcloned into pBluescript SK-(Stratagene). Subclones were sequenced from each end of the insert by using the universal primers in the plasmid. DNA sequencing was performed using an ABI 377 (Perkin-Elmer, Norwalk, Conn.) automated sequencer at the Arizona Research Laboratories (Tucson, Ariz.).

Reverse transcriptase-polymerase chain reaction (RT-PCR) was used to isolate a cDNA clone. RNA was isolated from 5-day-old dark- and light-grown seedlings. Superscript II reverse transcriptase (BRL, Gaithersburg, Md.) was used for the cDNA synthesis, according to the manufacturer's protocol. Briefly, 7 μg of total RNA was mixed with the reverse primer, D4R3. To the heat-denatured RNA-primer mix, the RT mixture was added and incubated for 1 hr at 43° C. Two microliters of RT product was used for PCR amplification by using different primers sets intended to cover all of the putative coding region. RT-PCR products were fractionated on an 9.8% agarose gel (Sambrook et al. 1989); the expected bands were purified using a Geneclean kit (BIO 101, Inc., Vista, Calif.), further amplified, and sequenced to determine the coding region.

B. Sequencing

Dwf4-2 was isolated from a T-DNA mutant population was an untagged allele, whereas dwf4-3 and dwf4-4 were obtained from plants obtained from the Nottingham *Arabidopsis* Stock Centre (University of Nottingham, UK; stock nos. N365 and N374); the mutagenesis method for these two lines is not known. Based on the DNA sequence of wild-type genomic DNA, pairs of primers were designed to amplify-1-kb stretches of genomic DNA. Oligonucleotide sequences are shown 5' to 3'. The numbers shown correspond to positions in the genomic sequence, with the adenine base in the translation initiation codon set as position. D40VERF, 1-ATGTTC-GAAACAGAGCATCATACT-24 (SEQ ID NO:3); D4PRM, (-1)-CCTCGATCAAAGAGAGAGAGA-(-21) (SEQ ID NO:4); D4RTF, 143-TTCTTGGTGAAACCATCGGT-TATCTTAAA-171 (SEQ ID NO:5); D4RTR, 853-TAT-GATAAGCAGTTCCTGGTAGATTT-828 (SEQ ID NO:6); D4F1, (-242)-CGAGGCAAC-AAAAGTAATGAA-(-222) (SEQ ID NO: 7); D4R1, 689-GTTAGAAACTCTAAAGAT-TCA-669 (SEQ ID NO:8); D4F2, 576-GATTCTTGGCAA-CAAAACTCTAT-598 (SEQ ID NO:9); D4R2, 1685-CCGAACATCTTTGAGTGCTT-1666 (SEQ ID NO:10); D4F3, 1606-GTGTGAAGGTTATAAATGAAACTCTT-1631 (SEQ ID NO:11); D4R3,3156-GGTTTAATAGTGTC-GACACTAATA-3132 (SEQ ID NO:12); D4F4, 2316-

CCGATGACTTGTACGTGCGTTA-2337 (SEQ ID NO:13); D4F5, 730-GCGAAGCATATAATGAGTATGGAT-753 (SEQ ID NO:14); AND D4R5, 1876-GTTGGTCATAAC-GAGAATTATCCAAA-1851 (SEQ ID NO:15). Because the two stock center lines were in a different genetic background than the wild-type gene that we had sequenced (WS), priers were based primarily on the exon sequence to avoid sequence variation between introns. Genomic DNA isolated from the mutants was subjected to PCR, using these primer sets. The amplified DNA fragments were fractionated on 0.8% TAE agarose gel (Sambrook et al. 1989), purified using Geneclean (BIO 101, Inc.) Qiaquick™ columns (Qiagen Inc., Chatsworth, Calif.), and sequenced. Putative mutations were identified by comparing the mutant DNA sequence with the wild-type sequence. The sequence was confirmed by sequencing independently amplified fragments at least three times for each mutation to eliminate PCR misincorporation.

C. Sequence Analysis

Annotations in multiple sequence alignment were performed using the ALSCRIPT package provided by Barton, G. J. (1993) *Protein Eng.* 6:37-40. Searches for similar protein sequence were performed with the BLAST program (Altschul et al. (1990), supra). In addition, useful packages, available on the internet, such as promoter, protein targeting, polyadenylation site, and splice site, have been employed to characterize the DNA and protein sequence (consolidated in the search launcher Baylor College of Medicine, Baylor, Tex.). All other sequence analysis was performed using the Genetics Computer Group (Madison, Wis.) software package.

Analysis of the complete genomic sequence, starting at the EcoRI site, with the promoter prediction by neural network (NNPP) package (hgc.lbl.gove/projects/promoter.html), indicated that the gene included a putative promoter (TATAT is found in the putative promoter region between nucleotides -143 to -78) and polyadenylation signal sequences (AATAA near a position at 3238 by and a putative GU-rich signature from 3283 to 3290 bp).

Unsuccessful attempts to detect mRNA by tissue-specific RNA gel blot analysis, using the 4.8-kb fragment as a probe, suggested that DWF4 encoded a rare message. In addition, there were no matching expressed sequence tags in the *Arabidopsis* database. Therefore, we screened two different cDNA libraries made with either normalized mRNA from different tissues or RNA from floral tissues, using the 4.8-kb fragment as a probe (ABRC stock numbers CD4-7 and CD4-6, respectively). After finding no positives in 109 clones screened, we chose to directly amplify DWF4 cDNA from total RNA made from 5-day-old seedlings, using reverse transcriptase-polymerase chain reaction (RT-PCR). Whereas RNA from both light-grown and dark-grown seedlings yielded the expected RT-PCR products, RNA from dark-grown seedlings generated significantly more. The bands were gel purified and sequenced. Alignment of the genomic and cDNA sequences indicated that the DWF4 gene was composed of eight exons and seven introns (FIG. 2A; FIG. 10).

Figure 2A:
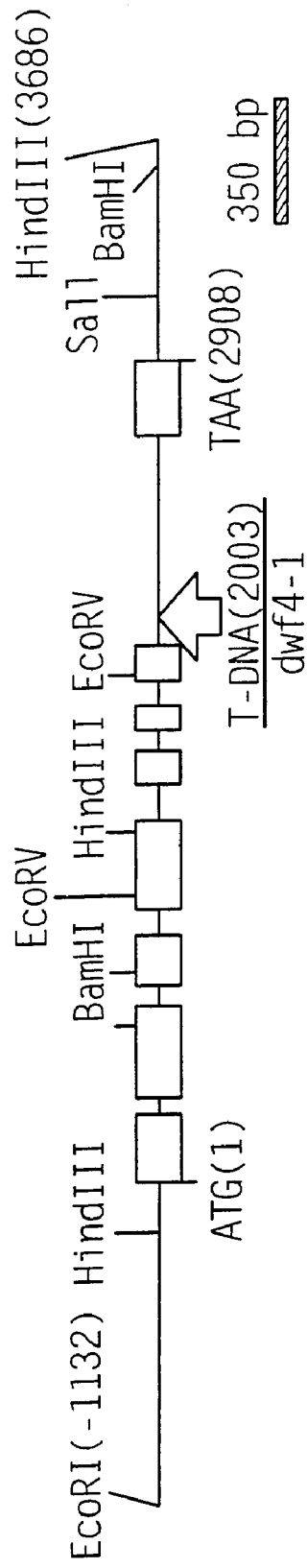
FIGS. 2A and B depict schematic representations of the DWF4 gene and protein.
Figure 2B:
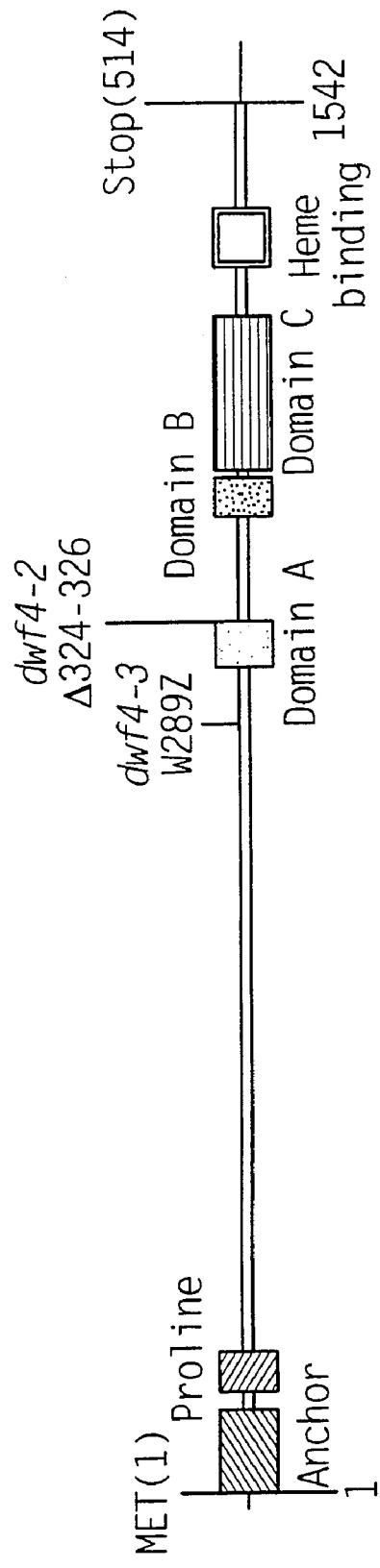
FIG. 2B shows the relative positions of the major domains in DWF4 cythochrome P450. All of the major domains found in the cytochrome P450 superfamily are conserved in DWF4. The estimated molecular mass and isoelectric point of the DWF4 protein were 58 kD and 7.28, respectively. Hydropathy plotting and protein localization prediction by the PSORT software package (Nakai and Kaneshia (1992) *Genomics* 14:897-911) suggested that he protein may reside in a membrane of the endoplasmic reticulum as an integral protein. Mutations identified in the other dwf4 alleles are indicated.

Sequence analysis of the dwf4-1 allele revealed that the T-DNA was inserted in the 5' end of introns 7 (FIG. 2A). In addition, sequence analysis of the left border plant junctions indicated that at one junction (5'), 75 by of unknown DNA was inserted, whereas at the other junction (3'), 24 by of left border and 19 by of plant DNA were deleted. To prove that DWF4 had been cloned, two other dwf4 alleles (dwf4-2 and dwf4-3) were sequenced to identify possible lesions. As shown in FIG. 2B, dwf4-2 contained a deletion of three conserved amino acids (324 to 326) caused by a 9-bp deletion, and dwf4-3 contained a premature stop codon (289) caused by changing a tryptophan codon (UGG) to a nonsense codon (UGA). Due to a premature stop codon, translation is predicted to be terminated before the heme binding domain, which is essential for cytochrome P450 function (Poulos et al. (1985) *J. Biol. Chem.* 260:16122-16130). Because T-DNA-generated alleles dwf4-1 and dwf4-2 and an additional mutant allele all possess loss-of-function mutations affecting the same protein, we conclude that we have cloned the DWF4 gene.

Example 3

The DWF4 Gene Encodes a Cytochrome P450

The open reading frame of DWF4 encodes a protein composed of 513 amino acids. BLAST database searches (Altschul et al. (1990) *J. Mol. Boil.* 215:403-410) for similar sequences yielded a superfamily of cytochrome P450 proteins as significant high-scoring segment pairs. Cytochrome P450s are heme-thiolate enzymes. They display a characteristic Soret absorption peak at 450 nm when the substrate-bound, reduced form is exposed to the light (Jefcoate (1978) "Measurement of substrate an inhibitor binding to microsomal cytochrome P-450 by optical-difference spectroscopy" in Methods in Enzymology, Vol. 52, S. Fleischer and L. Packer, eds (London: Academic Press), pp. 258-279). Typical microsomal cytochrome P450s hydroxylate various substrates via their monooxygenase activity, which utilizes molecular oxygen and reducing equivalents from NAD(P)H. In addition to the hydroxylation, other activities of cytochrome P450 enzymes, such as oxidation, dealkylation, deamination, dehalogenation, and sulfoxide formation, are involved in a variety of biological events in catabolism, anabolism, and xenobiotic metabolism in plants as well as animals (reviewed in West (1980) "Hydroxylases, monooxygenases, and cytochrome P-450" in The Biochemistry of Plants: A Comprehensive Treatise, Vol. 2, Metabolism and Respiration, D. D. Davies, ed (New York: Academic Press), pp. 317-365; Nebert and Gonzalez (1987), supra; Guengerich (1990) *Crit. Rev. Biochem. Mol. Biol.* 25:97-152, Guengerich (1993) *Am. Sci.* 81:440-447; Durst (1991) "Biochemistry and physiology of plant cytochrome P-450" in Microbial and Plant Cytochromes P-450: Biochemical Characteristics, Genetic Engineering and Practical Implications, K. Ruckpaul and H. Rein, eds (London: Taylor and Francis), pp. 191-232; Bolwell et al. (1994) *Phytochemistry* 37:1491-1506; Durst and Nelson (1995), supra; Schuler (1996) *CRC Crit. Rev. Plant Sci.* 15:235-284). Evolutionarily, cytochrome P450s have been found in a broad spectrum of living organisms, and they share significant homology at the amino acid sequence level. Thus, it has been proposed that all known cytochrome P450s were derived from a common ancestor (Nelson and Strobel (1987) *Mol. Biol. Evol.* 4:572-593).

Typical cytochrome P450s contain four characteristic domains as defined by Kalb and Loper 1988. Of the four domains, A, B, C, and D, at least two of them have been assigned specific functions. Domain A binds a substrate and molecular oxygen, and domain D has been shown to bind heme-prosthetic groups via a thiolate bond (Poulos et al. 1985). Thus, typically, microsomal cytochrome P450 enzymes can be identified by their characteristic signature sequences, including the heme binding domain, domain A (also referred to as dioxygen binding), domain B (steroid binding), and domain C (Nebert and Gonzalez (1987) *Annu. Rev. Biochem.* 56:945-993; Kalb and Loper (1988) *Proc. Natl. Acad. Sci. USA* 85:7221-7225). All of these signature sequences were found in DWF4; the relative positions of the domains are indicated in FIG. 2B.

Durst and Nelson (1995) *Drug Metab. Drug Interact.* 12:189-206 classified plant cytochrome P450s into two distinct groups based on their clustering nature in a phylogenetic tree. All of the group A families cluster and are assumed to originate from a common plant P450 ancestor. The group A cytochrome P450s conform to the characteristic consensus sequences (A/G)GX(D/E)T(T/S) in domain A (also called helix I) and PFG(A/S/V)GRRXC(P/A/V)G (SEQ ID NO:26) of the heme binding domain (D) with only a few exceptions. Group A cytochrome P450s appear to catalyze plant-specific reactions such as lignin biosynthesis (FIG. 6; GenBank accession number P48421). By contrast, P450s that do not belong to group A (non-A P450s) are scattered in the phylogenetic tree. They share more amino acid identity/similarity with P450s found in animals, microbes, and fungi than with those found in plants. The non-A P450s possess functions, such as steroid metabolism, that are not limited to plants. Generally, non-A P450s have limited homology with known domains described for group A.

The most similar protein to DWF4 is the *Arabidopsis* CPD protein, a non-A P450 A mutation in CPD also caused dwarfism (Szekeres et al. 1996; CYP90A1, GenBank accession number X87368). DWF4 and CPD share 43% identity and 66% similarity. Conforming to the recommended nomenclature for cytochrome P450 enzymes, DWF4 and CPD (CYP90A1) are grouped into the same family within different subgroups (Durst and Nelson (1995) *Drug Metab. Drug Interact.* 12:189-206). As such DWF4 represents a second member of the CYP90 family and is designated CYP90B1. Sequence similarity between the two proteins occurs throughout their length, with the greatest similarity in the classically conserved domains. Residues conserved between DWF4 and CYP90A are boxed and italicized in FIG. 3. The second most similar protein is the tomato CYP85 (Bishop et al. (1996), supra; GenBank accession number U54770). A mutation in this gene also results in dwarfism. DWF4 and CYP85 share 35% identity and 59% similarity in their overall protein sequences.

Six cytochrome P450 sequences with the greatest homology to DWF4, CYP90A1, CYP85, CYP88 (Winkler and Helentjaris (1995) *Plant Cell* 7:1307-1317; GenBank accession number U32579), cyanobacteria CYP120 (Kaneko et al. (1996) *DNA Res.* 3:109-136; GenBank accession number D64003), human CYP3A3X (Molowa et al. (1986) *Proc. Natl. Acad. Sci. USA* 83:5311-5315; GenBank accession number M13785), and zebrafish CYP26 (White et al. White (1996) *J. Biol. Chem.* 271:29922-29927; GenBank accession number U68234), were chosen for multiple sequence alignment. Putative domains defined by Kalb and Loper (1988), supra are boxed and labeled in FIG. 3. First, the heme binding domain pFGgFpRlCpGkel (SEQ ID NO:27) matches completely the sequence defined previously. Uppercase letters in the domain indicate amino acids conserved at all seven sequences in the alignment, and lower-case letters represent residues conserved in at least half of the proteins. Of the amino acids conserved in the heme binding domain, the function of the cysteinyl is established as a thiolate ligand to the heme (Poulos et al. (1985), supra).

Domain A is defined by xllfaGhEttssxIxxa (SEQ ID NO:28). Lowercase x's indicate variable amino acids. An invariant glutamate (E) preceded threonine (T) at position 314, T314, which is believed to bind dioxygen, was conserved in all proteins compared except CYP88 of maize. The second signature sequence, domain B, is also conserved in DWF4 with significant similarity. A valine at position 370 is conserved in all of the proteins, but is does not appear in Kalb and Loper's classic report (1988) on conserved domains. Again, DWF4 matches the domain C consensus sequence. Finally, the anchoring domain in the N-terminal end was distinguished by a repeat of the hydrophobic residue leucine. In addition, in DWF4, two acidic (glutamate) and two basic (histidine) residues precede the repeated leucine in the N-terminal leader sequence. These charged residues may add more stability to the membrane topology of the protein as a strong start-stop transfer peptide (von Heijne (1988) *Biochim. Biophys. Acta* 947:307-333).

Figure 4:
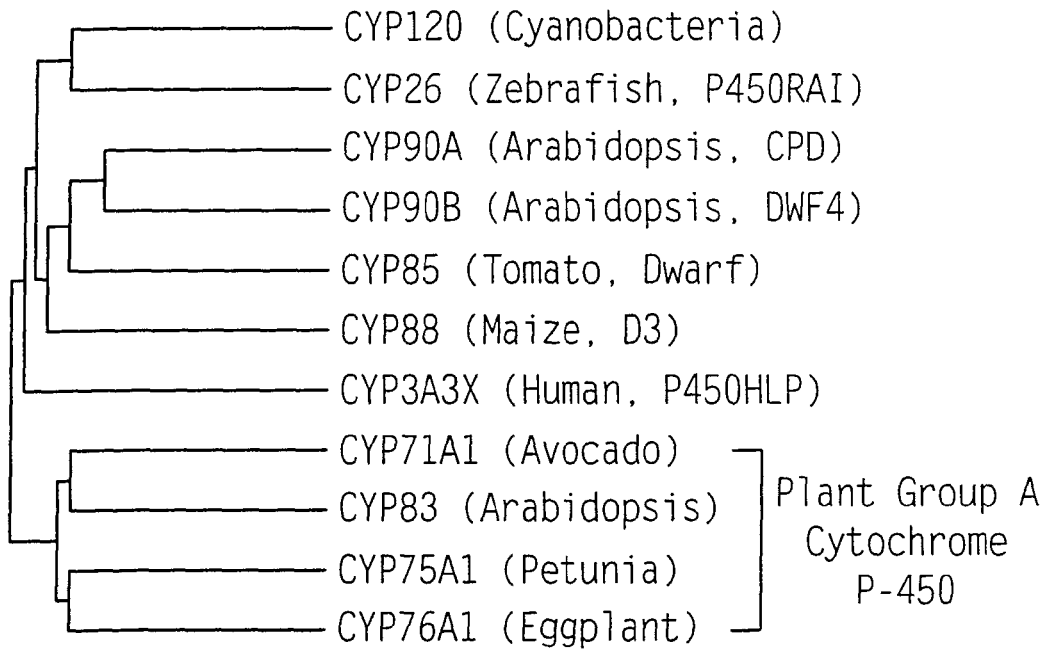
FIG. 4 depicts the phylogenetic Relationship between DWF4 and Selected Cytochrome 450s. DWF4 did not cluster with the group A plant cytochrome P450s that are known to mediate plant-specific reactions (Durst and Nelson 1995). CYP90A, CYP85, and DWF4, which are thought to be involve din BR metabolism, branched from CYP88, which mediates GA biosynthesis. GenBank accession numbers for the group A cytochrome P450s are M32885 (avocado; CYP71A1), P48421 (Arabidopsis; CYP83), P48418 (petunia; CYP75A1), and X71658 (eggplant; CYP76A1). The DISTANCE utility in the Genetics Computer Group software package was employed to calculate the relationships.

Thus, phylogenetic analyses of these seven proteins with cytochrome P450s unique to plants (group A; Durst and Nelson (1995), supra) indicate that DWF4 does not cluster with these cytochrome P450s (FIG. 4). Rather, DWF4 clustered with cytochrome P450s from other organisms: cyanobacteria (CYP120), rat (CYP3A2), human (CYP3A3X), and plants (CYP90, CYP85, and CYP88). DWF4 also deviates from the consensus sequence in the group A heme binding domain in that it possesses a PFGGGPRLCAG (SEQ ID NO:29) sequence in which arginine (R) is substituted for proline (P). However, domain A of DWF4, AGHETS (SEQ ID NO:30), fits the consensus of domain A of group A. These characteristics suggest that DWF4 is a monooxygenase, similar to P450s of group A, that utilizes molecular oxygen as a source of the hydroxyl group, but it mediates some reaction(s) that are not necessarily specific for plants, for instance, steroid hormone biosynthesis, which is a critical event for animals. In fact, the similarity of DWF4 to the rat testosterone 6β-hydroxylase (34%; GenBank accession number 631895) or glucocorticoid-inducible hydroxylase (31%; Molowa et al. 1986; GenBank accession number M13785) supports this idea. Further, the similarity that DWF4 shares with CYP90A and CYP85, 66 and 59%, respectively, is additional proof that it is involved in plant steroid biosynthesis (Bishop et al. 1996; Szekeres et al. 1996).

Example 4

The dwf4 Phenotype

As formally defined, a plant with a dwarf phenotype is one that has a short, robust stem and short, dark green leaves. dwf4 mutants are significantly smaller than the wild type and are dark green in color. They have short, rounded leaves. Again, the dwf4 phenotype is reminiscent of the light-regulatory mutant det2 (Chory et al., supra); however, complementation analysis has shown that the two mutations are not allelic, with the dwf4 mutation mapping to the lower arm of chromosome 3 and det2 mapping to chromosome 2 (Chory et al. supra). The results presented in Table 1 show that soil-grown wf4 plants attained a height of <3 cm at 5 weeks, whereas wild-type plants grew to >25 cm. Moreover, individual organs, such as leaves, were invariably shorter in dwarf plants. dwf4 siliques were also markedly shorter than those of the wild type and were infertile. The loss of fertility of dwf4 was due to the reduced length of the stamen filaments relative to the gynoecium, which resulted in mature pollen deposition on the ovary wall rather than on the stigmatic surface. Hand pollination of dwf4 flowers with either mutant or wild-type pollen resulted in good seed set without significantly changing the size of the siliques.

TABLE 1

The Development of Wild-Type and dwf4-1 plants

| Measurement | Wild-Type[a] | Dwf4-1[a] |
|---|---|---|
| | Five Weeks | |
| Height | 25.8 ± 2.6 cm | 2.8 ± 0.3 cm |
| Leaf blade length[b] | 1.72 ± 0.36 cm | 0.96 ± 0.15 cm |
| No. inflorescences | 0.77 ± 0.10 cm | 0.99 ± 0.18 |
| No. rosettes | 7.1 ± 0.9 | 13.5 ± 1.3 |
| | Other | |
| start of flowering | 21.5 days | 25.9 days |
| mature siliques length | 1.16 ± 0.07 cm | 0.29 ± 0 cm |
| No. seeds per Siliques | 37.7 ± 3.3 | 0.0 |
| Final no. of siliques | 336.5 ± 90.6 | 988.4 ± 214.2 |
| Height at maturity | 27.0 ± 2.7 | 11.6 ± 1.0 cm |

Figure 5:
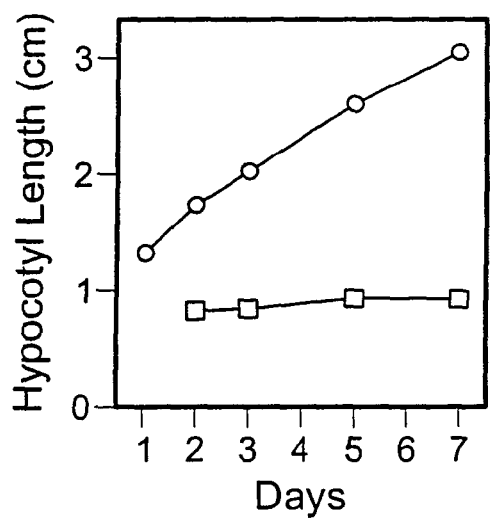
FIG. 5 depicts a comparison of wild-type and dwf4 hypocotyl growth rates. Circles indicate wild-type and square indicate dwf4. Each data point represents the average of 10 seedlings.

[a]results shown are the average ± SD of measurements taken from 10 plants
[b]measurements taken from the second pair of leaves Another feature of dwf4 plants is a reduction in apical dominance, as was evident by the threefold increase in the number of inflorescences at 5 weeks of age (Table 1). Mutants also had twice the number of rosette leaves, which may be explained by a prolonged vegetative phase in the dwf4 plants. Development of flowers on the primary inflorescence was delayed by ~4 days in dwf4, but the flowering phase was significantly longer in the mutant, with senescence of the last flower occurring at 98 days compared with ~57 days for the wild type. One result of this delay in senescence was that dwf4 plants contained almost three times the number of siliques as did the wild type (Table 1). The reduced stature observed in soil-grown dwf4 was also observed in hypocotyls of agar-grown seedlings. Measurements of hypocotyl length over time indicated that not only were dwf4 seedlings shorter than wild-type seedlings immediately after germination but also that the rate of growth was retarded in the mutants (FIG. 5). In addition, dwf4 hypocotyls reached their terminal length in <5 days, whereas wild-type seedlings continued to grow.

In sum, the dwf4 phenotype can be described as being due to both primary and secondary effects of reduced cell elongation. The primary effect is simply a reduction in the length of individual organs exclusively along their normal growth axis; that is, organ width is not reduced (Table 1). The secondary effects of reduced cell elongation are themselves due to the reduction in organ length. The dark green color of the leaves, for example, may be due exclusively to the existence of a wild-type number of chloroplasts in a significantly smaller cell. Similarly, the sterility of mutants is a consequence of the shortness of the stamens, which fail to deposit their pollen on the stigmatic surface. In addition to the morphological alterations of dwf4, mutants display delayed development, the first sign of which occurs at flowering (Table 1). Because rosette leaves are produced continuously during vegetative development, delayed flowering results in dwf4 rosettes having almost twice the number of leaves observed in the wild type.

Example 5

The Growth Defect of dwf4 Is Due to a Reduction in Cell Length

Both the short stature and the reduced growth rate of dwf4 could be due to a defect in cell division or cell elongation or both. To distinguish between these possibilities, we analyzed sections from 7-day-old hypocotyls and 5-week-old inflorescence stems, by light microscopy, as described in Example 1. To minimize variations due to the developmental stage of the sample, we always took the stem sections from the fourth internode. As shown in Table 2, the average cell size in dwf4 is significantly smaller than in wild-type plants, whereas no differences were detected in the number of cells along the length of either organ between the wild type and dwf4. Therefore, the short stature and reduced organ length of dwf4 are largely or exclusively due to a failure of individual cells to elongate. No differences were observed in the number of cell layers contained in the wild type and dwf4.

TABLE 2

Cell Length in Wild-Type and dwf4 plants

| Measurement | Wild-type | dwf4 |
|---|---|---|
| Average cell length in hypocotyl: 7 day old plant | 92.7 μm | 32.2 μm |
| Average cell length in stem: 5-week old plant | 79.2 μm | 15.0 μm |

The small size of dwf4 cells offers a possible explanation of the dark green color of the mutant plants. Chlorophyll measurements were taken, and leaf mesophyll protoplasts were prepared, stained, and measured to visualize and count chloroplasts, as described in Methods. Although there were no significant differences in total chlorophyll content, the chlorophyll a/b ratio, or the absorption spectra between wild-type plants and mutants, the mean plane area (the apparent two-dimensional surface area of mounted cells) of dwf4 leaf mesophyll protoplasts was 376 mm$^2$, whereas that of wild-type protoplasts was 599 mm$^2$. The two-dimensional comparison of plane area represents a dramatic reduction in volume for dwf4 cells. However, the number of chloroplasts per cell was only slightly lower: the mean number of chloroplasts per cell was 40 for dwf4 and 44 for the wild type. Therefore, dwf4 cells contain a greatly increased number of chloroplasts per unit cell volume. As a consequence, the chloroplasts are brought closer to each other making the color of the leaves appear darker. Chloroplast size was the same in both lines.

Thus, the rate of growth was significantly reduced in agar-grown dwf4 seedlings, which ceased to grow when their hypocotyl length was <20% of the final wild-type length. Because all of the cells in a hypocotyl before the initiation of leaf development are present in the embryo, the initial growth of seedlings is due exclusively to cell expansion, which therefore must be reduced in dwf4. A similar situation applies to soil-grown plants. Five weeks after germination, well after plants had bolted, dwf4 plants were shorter than wild-type plants (Table 1). Although the mutants continued growing for several weeks more than did the wild type, they remained shorter through senescence. That cell elongation is the direct cause of this decreased growth is shown by measurements of cell length both in 7-day-old hypocotyls (Table 2) and in 5-week-old stems (Table 2). Not only is the reduction in cell length in good agreement with the reduction in organ length, but insofar as could be determined, there is no difference in the number of cells between dwf4 and wild-type plants.

Figure 6:
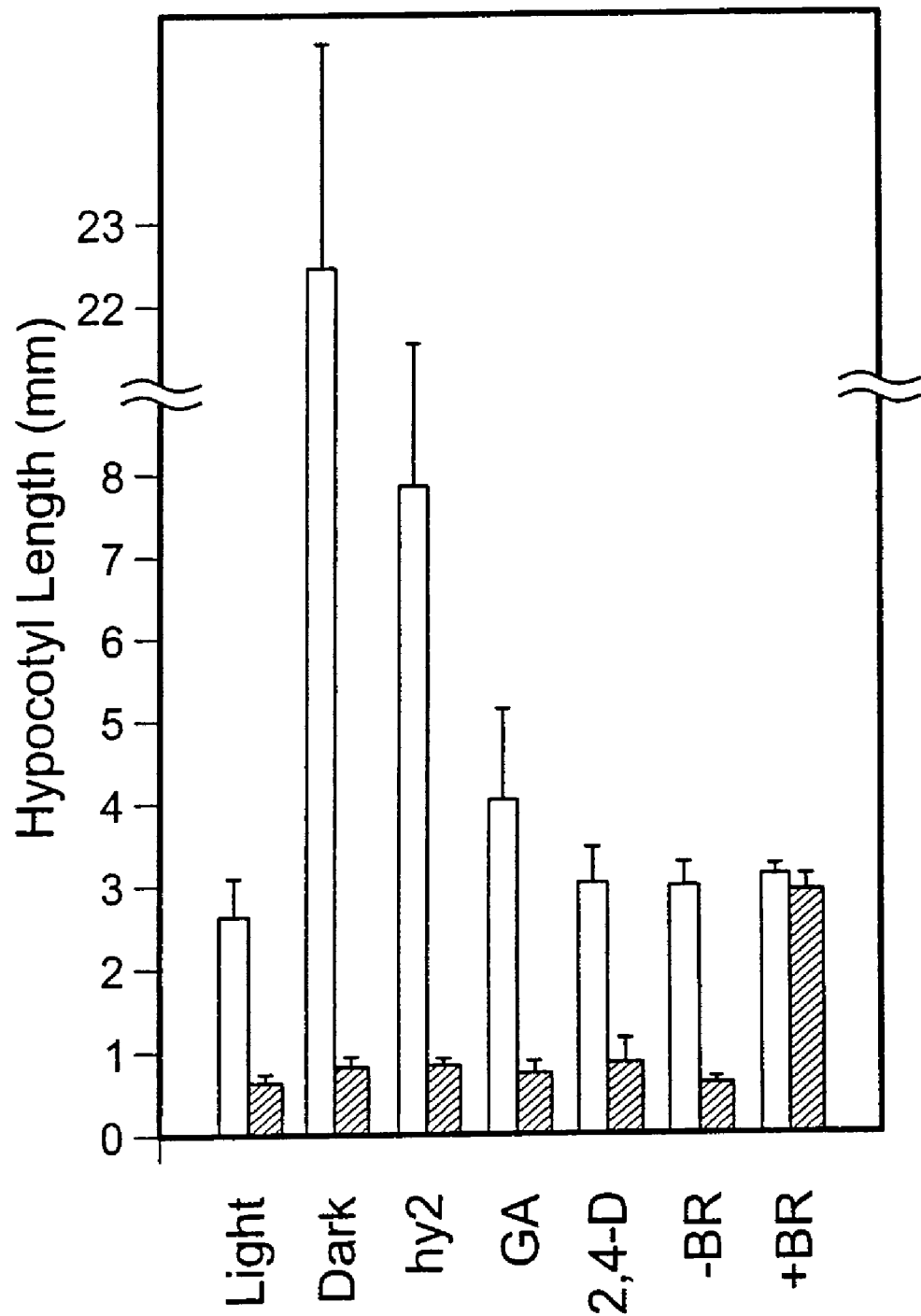
FIG. 6 depicts responses to cell elongation signals. BL measurements were performed with dwf4-3 and the corresponding wild-type control, Enkheim. Open bars indicate the wild type. Filled bars indicate dwf4. Lines above the bars represent one standard deviation. On the horizontal axis, "light" refers to light-grown controls; "dark" refers to dark-grown controls; "hy2" refers to DWF4 and dwf4 plants in a hy2 background; "GA" refers to plants grown in $10^{-5}$ M GA; "2,4-D" refers to plants grown in $10^{-8}$ M 2,4-D "BR" refers to liquid-grown controls; and "+BR" refers to liquid-grown controls with $10^{-8}$ M BL.

Organ growth by cell elongation in plants occurs as part of normal development in response to a variety of input signals. Mutants that are defective in these signaling pathways invariably fail to elongate normally in response to the appropriate stimuli. A mutant with a block at a step that is common to several individual pathways would therefore be expected to have defective responses to all of the corresponding signals. dwf4 appears to be such a mutant. FIG. 6 shows that elongation induced by the hy2 mutation is blocked in a dwf4 hy2 double mutant. Not surprisingly, in view of this result, dwf4 failed to display hypocotyl elongation as a response to growth in complete darkness. In addition, dwf4 was capable of perceiving GA, but its response was severely composed. This mutant could also respond to the inhibitory effects of auxin but was incapable of auxin-stimulated elongation. It was only exogenous BL that fully restored wild-type length to dwf4 hypocotyls (Choe et al. (1998), supra).

Because dwf4 failed to respond to at least three independent signaling pathways but responded fully to only one, the most likely explanation for the dwarf phenotype is therefore that a fully functional BR system is required for a full response to GA, auxin, and deetiolation. From the perspective of cellular economy, it may be advantageous that the downstream elements involved in cell elongation are shared among at least some of the signaling pathways that evoke this response. The interaction of various pathways at a common step provides the plant with a potential point for the integration of signals produced by diverse independent stimuli. Our results indicate that BRs act at this downstream step.

Example 6 dwf4 Is Specifically Rescued by Brs

The reduced length of cells in dwf4 hypocotyls and inflorescence stems is indicative of a failure of these cells to elongate during development. A variety of endogenous and environmental signals is responsible for stimulating elongation in plants; therefore, a series of experiments was performed to determine whether dwf4 is affected in a specific signaling pathway or is blocked in elongation as a response to various signals.

Of the endogenous (hormonal) signals that might be deficient in dwarf plants, an obvious candidate is GA, because gibberellin-deficient mutants are shorter in stature than are the wild-type plants (Koornneef and Van der Veen, supra). Our results, however, indicate that dwf4 is not defective in the synthesis of gibberellins. When germinated on $10^{-5}$M GA, wild-type seedlings demonstrated an elongation response (FIG. 6), whereas dwf4 seedlings responded minimally, if at all. At $10^{-4}$ M GA, wild-type seedlings elongated slightly more than at $10^{-5}$ M, but the dwf4 seedlings were essentially saturated for elongation at $10^{-5}$ M GA. Similar results were obtained when soil-grown plants were sprayed with 1 mM GA once inflorescences first became visible: dwf4 inflorescence stems elongated by only 28% above the untreated controls, whereas those of the wild type elongated by 45% above the untreated controls. Mutants that owe their reduced stature to decreased levels of endogenous gibberellins can be fully rescued by added hormone (Koornneef and Van der Veen, supra; Talon et al., supra). In addition, dwf4 seeds germinate in the absence of exogenously supplied GA. Our results therefore suggest that dwf4 is not deficient in endogenous GA. A corollary conclusion from this experiment is the demonstration that dwf4 is capable of detecting GA; that is, it is not likely to be affected in signal perception but rather is defective in the extend to which it can respond to this signal.

Auxin can also stimulate cell elongation. This effect is especially visible in young seedlings (Klee and Estelle, supra). The response of wild-type and dwf4 plants to auxin was tested by growing seedlings for 10 days on vertically oriented plates containing various concentrations of the synthetic auxin 2,4-D. At all concentrations assayed, inhibition of root growth was evident. FIG. 6 shows that at $10^{-8}$ M 2,4-D, hypocotyl elongation in wild-type and dwf4 seedlings was similar to that of the controls. Higher concentrations of auxin were inhibitory for both wild-type and dwf4 seedlings, and lower concentrations had no effect. In view of the inhibition of root growth, it is clear that dwf4 is not auxin resistant; rather, its elongation response is compromised.

As mentioned above, the most obvious exogenous signal for plants is light. Therefore, to investigate whether light-regulated cell elongation is altered in dwf4, wild-type and dwf4 seedlings were grown in the dark, as described in Example 1. FIG. 6 shows that as expected, wild-type seedlings displayed hypocotyl elongation typical of etiolated growth. By contrast, dark-grown dwf4 seedlings were only slightly longer than those grown in the light. To assess the relationship between the dwf4 phenotype and light sensing by dwf4, the mutation was crossed into a mutant defective in the HY2 GENE. All by mutants share the common phenotype of an elongated hypocotyl that mimics part of the etiolation response in the light. Specifically, hy2 is deficient in active phytochrome because chromophore biosynthesis does not take place (Chory et al. (1989a) Plant Cell 1:867-880). FIG. 6 shows that dwf4 hy2 double mutants displayed a dwarfed phenotype indistinguishable from that of dwf4 HY2 (light-grown control); therefore, the elongation block due to the dwf4 mutation is epistatic to a defect in phytochrome activity.

In the course of our studies, we prepared a genomic library from dwf4-1, from which we isolated a clone in which a fragment of T-DNA interrupts a gene encoding a putative cytochrome P450 steroid hydroxylase. Because BRs have been shown to elicit elongation in *Arabidopsis* (Clouse et al. (1993) *J. Plant Growth Regul.* 12:61-66) and because BR-deficient mutants have been recently described (Kauschmann et al. (1996), supra, Li et al. (1996), supra; Szekeres et al., supra), we tested the effect of BL on *Arabidopsis* seedlings by germinating seeds in liquid medium containing different amount of BL. As shown in FIG. 6, the dwf4 hypocotyls were restored to wild-type height by $10^{-6}$ M BL. This, together with our identification of a disrupted gene encoding a putative BR biosynthetic enzyme, strongly suggests that the phenotype of dwf4 is specifically due to a defect in BR biosynthesis (see Choe et al. (1998 *Plant Cell* 10:231-243).

Thus, the results indicate that BL is involved at or near a downstream control point where multiple signaling pathways interact. First, as shown in FIG. 6, BL is required for cell elongation as a response to darkness as well as GA and auxin. In addition, previous studies (Kauschmann et al. (1996), supra; Li et al. (1996), supra; Szekeres et al. (1996), supra) and the work described herein show that BR can compensate for the cell elongation defect of mutants as diverse as det2, cpd, dwf4, det1, cop1, and dwfl. This places BRs downstream of all the cellular functions affected in these mutants. Finally, at least one of the BR biosynthetic genes has been shown to be modulated by light, cytokinins, and the carbon source (Szekeres et al. (1996), supra).

Mutations in axr2 result in a dwarf growth habit and a dark-grown phenotype with short hypocotyl and open cotyledons (Timpte et al. (1992), supra. In addition, axr2 mutants are resistant to auxin, ethylene, and abscisic acid and have defective root and shoot gravitropism. The dwarf phenotype in axr2 mutants has been shown to be due to reduced cell elongation and is rescued by BL (Szekeres et al. (1996), supra). This suggests that tat least one of the multiple hormone signaling pathways affected in axr2 involves a BR-dependent step. Mutations at another locus, acaulis1, also have a significant reduction in cell elongation, but the defect is confined to inflorescence stems and leaves (Tsukaya et al. (1993) *Development* 118:751-764). Flowers are fully fertile and mature into normal-sized siliques with normal seed set. There is no change in hypocotyl length. If BRs are directly involved in this apparently organ-specific signaling pathway, it may be due to organ-specific responsiveness to individual BR species. With regard to the mechanism of action of BRs, at the moment one can only speculate that the target may be a component of the cell expansion machinery. Perhaps steroid signaling initiates a series of events leading to cell with loosening.

Example 7

The Elongation Defect of dwf4 Leads to a Light-Regulatory Phenotype

The BR-deficient mutant det2 was originally identified as defective in regulation by light (Chory et al. (1991), supra). Given the similarity of det2 and dwf4 phenotypes and functions and in view of the observation that dwf4 is epistatic to hy2, one can predict that the etiolation response, which includes significant hypocotyl elongation, would not be normal in dwf4. To assess to what extent the etiolation response is affected by BR-dependent cell elongation, we grew dwf4 and wild-type plants on agar under continuous light or in complete darkness, as described above in Example 1. After 7 days of growth in the light, wild-type seedlings displayed open and expanded cotyledons as well as emerging leaf buds. In contrast the overall appearance of light-grown dwf4 seedlings was strikingly similar to that of det2 (Chory et al. (1991), supra). dwf4 hypocotyls were very short, and the cotyledons were smaller than those of the wild type, displaying significant epinastic growth. As expected, dark-grown wild-type seedlings had a typical etiolated appearance, with a highly elongated hypocotyl and closed, unexpanded cotyledons. However, dwf4 hypocotyls failed to elongate. That the dwf4 mutation can abolish the elongation component of the etiolation response is in agreement with the notion that the block in cell elongation in dwf4 is specifically a BR-dependent process.

In addition to short hypocotyls, dark-grown dwf4 seedlings displayed partially open cotyledons and leaf primordial, with up to four leaf buds clearly visible. This has not been observed with the wild type, although it occurs with certain light-regulatory mutants (Chory et al. (1998b), supra; Deng et al. (1991 Genes Dev. 5:1172-1182; Wei and Deng (1992), supra). dwf4 leaf development continued in the darkness for several weeks, resulting in significant expansion of rosette leaves. These results indicate that dwf4 plants can initiate what is normally a photomorphogenic pathway in the absence of light. Although this is often diagnostic of a light-regulatory mutant, wild-type *Arabidopsis* can perform leaf development and even flowering in complete darkness when grown in liquid culture (Araki and Komeda (1993) *Plant J.* 4:801-811).

The cause for this dark-flowering effect is not understood; therefore, the possibility exits that leaf development in dark-grown dwf4 is related to dark flowering and not to a light-regulatory defect. For example, perhaps the proximity of the dwf4 shoot apical meristem to the surface of the agar, due to the shortness of the hypocotyls, mimics some effect of submerged culture, such as a high water potential or a high concentration of some nutrient. To test this possibility, wild-type seedlings were grown in complete darkness for 6 weeks in vertically oriented dishes to maximize contact between the seedling and the medium. Wild-type seedlings grown in this fashion displayed open cotyledons and underwent at least partial leaf development. In fact, all wild-type seedlings grown along the surface of the agar showed development of an inflorescence with at least one cauline leaf and a terminal flower bud. We conclude, therefore, that the appearance of leaves in dark-grown dwf4 may be due simply to its short size and the culture conditions.

A number of light-regulatory mutants have been described that undergo photomorphogenesis in the dark at the cellular level. In mutants such as cop1, cop8, cop9, cop10, and cop11, stomata undergo photomorphogenic maturation (Deng and Quail (1992), supra; Wei and Deng (1992), supra; Wei et al. (1994), supra); of these cop1 and copy9 as well as det1 (Chory et al. (1989b), supra) also initiate differentiation of plastids into chloroplasts. To determine whether dwf4 plants undergo photomorphogenic cellular differentiation in the dark, we analyzed cotyledons from light- and dark-grown plants by transmission and scanning electron microscopy. Analysis of plastids in thin sections from 7-day-old dark-grown seedlings showed no difference between the wild type and dwf4. Both lines contained normal chloroplasts when grown in the light, whereas dark-grown seedlings contained etioplasts, with their characteristic prolamellar body and no significant organization of thylakoids. Analysis of stomatal structures on the underside of cotyledons from 7-day-old seedlings indicates that stomatal development was not completed in the dark, because the stomatal opening was occluded in both lines. The majority of light-regulatory mutants analyzed to date displayed light-grown morphology in the dark without concomitant chloroplast or stomatal development. As in these mutants, therefore, the dwf4 mutation uncouples the developmental pathway of seedling morphology from that of light-regulated cellular differentiation.

An additional feature of many light-regulatory mutants is that photomorphogenesis in the dark is accompanied by expression of genes that normally are light induced (Chory et al. (1989b), supra, Chory et al. (1991), supra; Deng et al. (1991), supra; Wei and Deng (1992), supra; Hou et al. (1993), supra; Wei et al. (1994), supra). To assess whether dwf4 is able to induce light-regulated transcripts in the dark, we compared the activity of a CAB promoter fused to the *Escherichia coli* gene uidA, encoding β-glucuronidase (GUS), in light- and dark-grown dwarf and wild-type plants. The CAB-uidA fusion in pOCA107-2 (Li et al. (1994) *Genes Dev.* 8:339-349) was crossed into dwf4, and F2 dwarf and wild-type pants were grown in the dark or light for 12 days, followed by determination of GUS activity by fluorometry (Gallagher (1992). Quantitation of GUS activity by fluorometry" in GUS Protocols, S. R. Gallagher, ed (New York: Academic Press), pp. 47-59).

The results demonstrated that when grown in the light, both wild-type and dwf4 seedlings contained GUS activity, which was significantly reduced in both lines when grown in the dark. Moreover, dark-grown dwf4 seedlings displayed no GUS activity above the background present in dark-grown wild-type plants. The absence of light-induced gene expression in the dark is a distinguishing feature of certain cop and det mutants, such as cop2, cop3 and det3. Because we have shown that the defect in cell elongation of dwf4 is specifically rescued by BRs, even in the presence of light, we conclude that this is not a light-regulatory mutant. That its phenotype is partially deetiolated or constitutively photomorphogenic is a secondary effect of its reduced stature and the growth conditions.

Example 8

Abnormal Skotomorphogenesis as a Consequence of the Dwarf Growth Habitat

When dwf4 is grown in the light, its morphology is similar to that of various cop and det mutants, with multiple short stems, short rounded leaves, loss of fertility due to reduced stamen length, and delayed development (FIG. 6). Dark-grown dwf4 seedlings possess short hypocotyls, open cotyledons, and developing leaves. Therefore, it is tempting to speculate that this mutant may be defective in the control of light-regulated processes. On the other hand, because a dark-flowering phenotype has been demonstrated for liquid-grown *Arabidopsis* (Araki and Komeda (1993), supra), and given that agar medium is mostly water, it is especially significant that it is the dwarf seedlings, whose apical meristems are very close to the agar surface, that display a light-grown phenotype in the dark. Furthermore, because wild-type seedlings grown along the surface of the agar reproduce the dark-flowering phenotype, it is possible that the apparent light-regulatory defect of dwarf seedlings is a dark-flowering response. This possibility is strengthened by the observation that wild-type seedlings (ecotype Wassilewskija [Ws-2]) grown in the dark on horizontally oriented plates occasionally bend down and touch the agar surface and these seedlings invariably produce leaves.

In addition, of the eight DWF4 loci identified in this laboratory, only the shortest mutants displayed open cotyledons and leaf bud development; in the case of dwf1 (Feldmann et al. (1989), supra), this aberrant skotomorphogenesis is confined to the most severely affected alleles. In addition to the presence of a short hypocotyl and at least partially open cotyledons in the dark, cop1 (Deng and Quail (1992), supra), det1 (Chory et al. (1989b), supra), and det3 (Cabrera y Poch et al. (1993) *Plant J.* 4:671-682) have been shown to initiate leaf formation in the dark. In mutants such as cop1, cop8, cop9, cop10, and cop11, stomata undergo photomorphogenic maturation (Deng and Quail (1992), supra; Wei and Deng (1992), supra; Wei et al. (1994)), supra); of these, cop1 and cop9 as well as det1 (Chory et al. (1989b), supra) also initiate differentiation of plastids into chloroplasts. dwf4 displayed, in addition to a light-grown dwarf phenotype, a dark-growth phenotype of short hypocotyls, open cotyledons, and developing leaves; however, in contrast with the light-regulatory defect seen with whole plants, the cellular differentiation phenotype was unaffected. In dark-grown dwarf seedlings, stomata did not complete their development, and differentiation of chloroplasts was not observed. The absence of a cellular light-regulatory phenotype in dwf4 is similar to that of a number of photomorphogenic mutants, such as det2, det3, cop2, cop3, and cop4 (Chory et al. (1991), supra; Cabrera y Poch et al. (1993), supra; Hou et al. (1993), supra).

In view of the dark-flowering phenotype on agar and the absence of a light-regulatory defect in differentiating cells, we conclude that at least in the case of dwf4, aberrant skotomorphogenesis may be a consequence of a dwarf growth habit rather than dwarfism being part of a defect in the control of light=regulated processes. This effect may also explain the light-regulatory phenotype found in other mutants with severely reduced height, such as axr2 (Timpte et al. (1992), supra), and strong alleles of dwf1, both of which are also rescued by exogenous BRs (Szekeres et al. (1996), supra.

Example 9

Feeding Experiments with BR Biosynthetic Intermediates

In view of the results described above, we hypothesized that DWF4 mediates one or more of several steroid hydroxylation steps in the BR biosynthetic pathway. To test this, dwf4 was grown on all of the available biosynthetic intermediates in the BR biosynthetic pathways and examined to ascertain which intermediates could rescue the dwarf phenotype. In addition to the intermediates belonging to the early C-6 oxidation and late C-6 oxidation pathways (Choi et al. (1997), supra), 22α-hydroxycampesterol (22-OHCR), 6α-hydroxy-castasterone (6-OHCT) (Takatsuto et al. (1997) *J. Chem. Res.* (synop.) 11:418-419), and 6α-hydroxycastasterone (6-OHCS) (S. Takatsuto, T. Watanabe, T. Noguchi, and S. Fujioka, unpublished data) were synthesized and tested.

Germinated seedlings were transferred to media supplemented with one of the intermediates or BL to pinpoint the step catalyzed by DWF4. Cathasterone (CT; early C-6 oxidation pathway), 6-OHCT, 6-deoxocathasterone (6-deoxoCT; late C-6 oxidation pathway), and 22-OHCR, and all of the downstream compounds belonging to each branch, rescued the light-grown dwf4 phenotype, whereas the known precursors failed to cause an elongation response. Rescued seedlings exhibited greatly elongated cotyledonary petioles and expanded cotyledons, moderately elongated hypocotyls, and leaves that were larger and not as curled compared with nonrescued dwarfs. In addition, the rescued seedlings were less green than the dwarfs. These experiments were conducted in liquid media. Feeding experiments performed in the dark yielded similar results.

Dose-response tests on the putative substrates and products of DWF4 were also performed. dwf4 seedlings failed to respond to 6-oxocampestanol (6-oxoCN) even at high concentrations ($3\times10^{-6}$ M). However, on CT the overall morphology of dwf4 was essentially rescued to wild-type phenotype at $3\times10^{-7}$ M and higher, whereas with 6-deoxoCT, rescue occurred with as little as $10^{-7}$ M and may have even been inhibitory at higher concentrations. Of particular interest is the more dramatic response of the epicotyls versus the smaller response of the hypocotyls to CT. This same phenomenon was true for seedlings treated with $>10^{-7}$ M 6-deoxoCT. At concentrations $>10^{-7}$ M, the seedlings displayed an inhibition in hypocotyl and root elongation as well as cotyledon and leaf expansion.

In a dose-response experiment performed in the dark, the seedlings failed to respond to 6-oxoCN ($10^{-8}$ to $3\times10^{-6}$ M). A higher concentration of CT for dark-grown seedlings, compared with light-grown seedlings, $3\times10^{-6}$ M (FIG. 5B), was required to convert the hypocotyl to a length similar to that of the wild type. High concentrations of 6-deoxoCT caused dramatic elongation but were less effective at rescuing dwf4 hypocotyls to wild-type phenotype.

To determine whether the results of the seedling feeding experiments could be applicable to soil-grown mature plants, 6-week-old dwf4 plants were treated with BR intermediates and BL. Concentrations of applied intermediates were adjusted empirically to optimize responses. Consistent with the results obtained from the seedlings experiments, only 22α-hydroxylated compounds can rescue the dwf4 phenotype. The elongation response was only observed in the young tissues of the inflorescence, regardless of whether the BRs were applied locally or sprayed over the entire plant. In contrast to the striking elongation of the peduncles and pedicels, fertility was not restored by BR treatment. The sterility in dwf4 is hypothesized to be mechanical, which means that the filaments are shorter than the carpels such that the pollen is shed onto the ovary walls rather than onto the stigmatic surface. In fact, if dwf4 plants are hand pollinated using dwf4 pollen, fertility increases.

Figure 7:
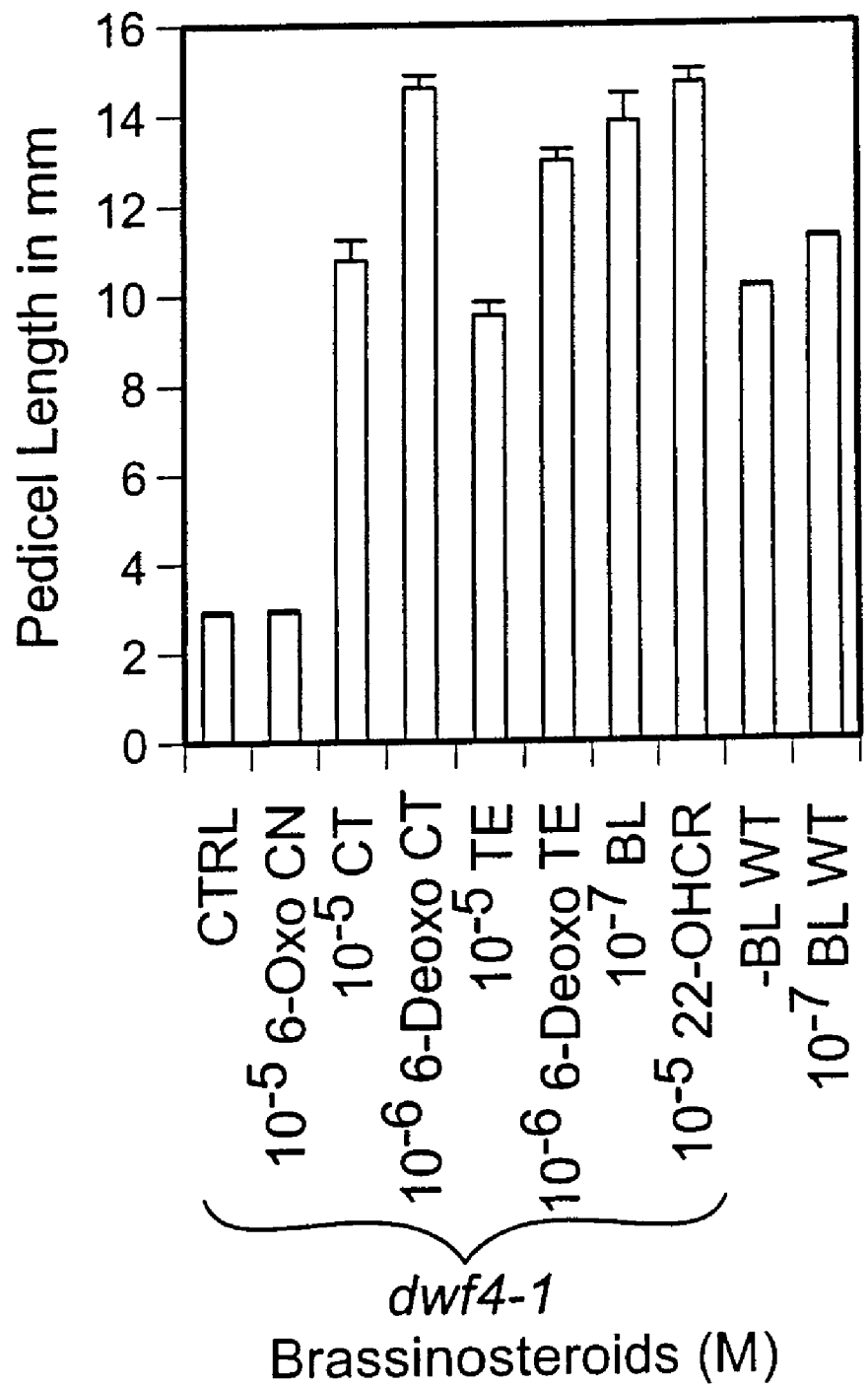
FIG. 7 depicts pedicel elongation of dwf4 mature plants in response to exogenous application of BR. Measurements were performed with the BR-fed plants. dwf4-1 plants were more sensitive to intermediates belonging to the late C-6 oxidation pathway ($10^{-6}$ M 6-deoxoCT and $10^{-6}$ M 6-deoxo TE) compared with compounds in the early C-6 pathway ($10^{-5}$ M CT and $10^{-5}$ M TE). BL ($10^{-7}$ M) induced almost the same amount of elongation with one-tenth the concentration of its precursors. Rescue by 22-OHCR ($10^{-5}$ M), which is structurally similar to the presumed precursor CR, except for a 22α-hydroxyl functional group, shows that the only defect in dwf4 is the C-22 hydroxylation reaction. Complementing intermediates and BL induced dramatic elongation in the elongating zone of the inflorescence and pedicel, but fertility was not increased. Data represent the means +SE of 15 to 20 pedicels. "CTRL" refers to control; "WT" refers to wild type.

Pedicels displayed a more consistent response to exogenously applied BRs than did internodes, which led us to quantify the sensitivity of pedicels to these compounds. As shown in FIG. 7, dwf4 pedicels were more sensitive to BR intermediates belonging to the late C-6 oxidation pathway, 6-deoxoCT ($10^{-6}$ M) and 6-deoxoteasterone (6-deoxoTE; $10^{-6}$ M), compared with CT ($10^{-5}$ M) and teasterone (TE; $10^{-5}$ M) of the early C-6 oxidation pathway. The end product of the BR pathway, BL ($10^{-7}$ M), possessed the highest bioactivity. This concentration induced approximately the same degree of response as its precursor compounds at $10^{-6}$ M. Finally, application of 22-OHCR ($10^{-5}$ M also resulted in a dramatic elongation response (FIG. 7).

Rescue of dwf4 by 22-hydroxylated steroids confirms that the missing step in dwf4 is hydroxylation at the C-22 position. IN fact, we found that the chemically synthesized 22-OHCR was also effective in rescuing dwf4 (FIG. 7) hydroxylation at C-22. these results indicate that there is no defect other than 22α-hydroxylation in dwf4 plants.

In BR biosynthesis, Fujioka and Sakurai (1997b), supra have demonstrated that there are at least two branched biochemical pathways to the end product BL (FIG. 1; Fujioka and Sakurai (1997a), supra, Fujioka and Sakurai (1997b), supra; Sakurai and Fujioka (1997), supra). Depending on the oxidation state of C-6, they are referred to as the early or late C-6 oxidation pathways. In the early pathway, the C-6 is oxidized to a ketone at campestanol (CN), whereas in the late pathway it is oxidized at 6-deoxocastasterone (6-deoxoCS). Otherwise, the two pathways share equivalent reactions. Our results from the experiments with the available BR intermediates clearly demonstrate that dwf4 is defective in the 22α-hydroxylation steps in each of the pathways. Application of all 22α-hydroxylated intermediates in these pathways, such as CT and 6-deoxoCT, cause dramatic elongation of dwf4 plants, but compounds not hydroxylated at C-22 had no effect. This results also suggests that DWF4 recognizes at least two substrates: N and 6-oxoCN. It seems reasonable to hypothesize that the same results will be found for CPD, a 23α-hydroxylase; that is, it will use 6-deoxoCT as well as CT as substrate.

The rescue of dwf4 by 22-OHCR is an important observation. First, it confirms DWF4 as a 22α-hydroxylase. Second, this result suggests that 22-OHCR was metabolized to induce the same responses as other complementing BRs. This is not just a general effect because our unpublished data show that another dwarf mutant that we have identified in our screens, dwf8-1, is not rescued by this compound. Finally, these feeding experiments suggest that the metabolism of 22-OHCR may represent a new subpathway in the BR biosynthetic pathway. If this compound also exists in vivo and constitutes the first step in a separate subpathway by analogy to the chemical structure, the C-6 hydroxylated BRs, for example, 6-OHCT, 6-hydroxyteasterone, and so on, may be possible intermediates in this network. If so, the intermediates in this pathway may play a role as bridging molecules between the early and late C-6 oxidation pathways. Alternatively, it might be possible that 22-OHCR merges into one of the two pathways to be metabolized. In this case, the late C-6 oxidation pathway is the best candidate; our unpublished data show that 22-OHCR is more effective in the light in rescuing the dwf4 phenotype, which is true for all of the intermediates in the late C-6 oxidation pathway.

Currently, biochemical feeding studies suggest that the two pathways merge to produce BL or CS (Yokota et al. (1991), Metabolism and biosynthesis of brassinosteriods. In Brassinosteroids: Chemistry, Bioactivity, and Application, H. G. Cutler, T. Yokota, and G Adam, eds (Washington, D.C.: American Chemical Society), pp. 86-96; Yokota, et al. (1997) *Plant Physiol.* 115(suppl.):169; FIG. 1). Several lines of evidence indicate that seemingly redundant pathways can be utilized to respond toe environmental or developmental signals. First, the pathways could respond to specific signals. For instance, it is possible that various cues such as light, dark, or developmental signals play a role in regulating these subpathways. Our feeding experiments consistently showed that BRs in the late C-6 oxidation pathway are more effective at promoting cell elongation in light-grown plants (dwf4 and wild type; FIG. 7) and that the BRs belonging to the early C-6 oxidation pathway are more active in dark-grown seedlings. Thus it may be possible that the late C-6 oxidation pathway operates in the light and that the early C-6 oxidation pathway functions primarily in the dark. Second, rather than a simple merger of branched pathways to BL as an end product, each intermediate may have nascent bioactivity. The in vivo ratio or composition of BRs at different oxidation statues may result in different responses. Noticeably distinctive phenotypes for the various BR dwarfs, defective in different biosynthetic steps, support this idea. Third, the biosynthetic rate of each pathway toward production of the end product may differ. In this case, the biosynthetic rate could be modulated by controlling the level of gene expression or the activity of participating enzymes. Certain signals, requiring different rates of BR biosynthesis, may induce one of the subpathways, which would then affect the concentration of the intermediates in one pathway relative to the other.

Of the steps in BR biosynthesis in Madagascar periwinkle, the 22α-hydroxylation reaction has been suggested to be the rate-limiting step (Fujioka et al. (1995a) *Biosci. Biotech. Biochem.* 59:1543-1547). In periwinkle, the endogenous level of CT was as low as one-twenty thousandth of CR; however, CT was almost 500 times more active than 6-oxoCN in the rice-lamina inclination assay (Fujioka et al. (1995b) *Biosci. Biotech. Biochem.* 59:1973-1975). Based on these results, we propose that the step encoded by DWF4 serves as the rate limiting reacting and that once past this step, the intermediates are easily converted to the end product. Although biochemical studies on DWF4 need to be performed to ascertain whether it mediates the rate-limiting step, DWF4 seems to be greatly downregulated compared with CPD, the next enzyme in the pathway; RT-PCR revealed that the DWF4 transcript is much less abundant than the CPD transcript.

Example 10

A. Promoter and Overexpression Constructs

Two promoter constructs were used for the DWF4-promoter:GUS(D4G) analysis. For promoter fusions, polymerase chain reaction (PCR) products spanning 1.1 kb DNA upstream of the translation initiation site were amplified using primers D4XLINIT (5'-TAGGATC-CAGCTAGTTTCTCTCTCTCTCT-3') (SEQ ID NO:16) and a T7 primer (5'TAATACGACTCACTATAGGG-3') (SEQ ID NO:17). For template for PCR, a DWF4 genomic clone subcloned into pBluescript SK-vector (Stratagene La Jolla, Calif.) was used as described herein. The PCR products were restricted with SalI and BamHI, and ligated into the same restriction site of a promoterless GUS vectors pBI101; this 1.1 kb promoter:GUS construct as named pD4GL. For the pD4GS construct, pD4GL was digested with HindIII, the small restriction fragment was removed, and the remaining vector with the partial promoter was self-ligated. The constructs were introduced into *Agrobacterium* strain GV3101 through electroporation.

For a DWF4 overexpression construct, PCR products were made by using D40VERFA (5'-GAATTCTAGAATGTTC-GAAACAGAGCATCATA-3') (SEQ ID NO:18) and D4R2 (5'CCGAACATCTTTGAGTGCTT-3') (SEQ ID NO:10) primers and Wassilewskija-2 (Ws-2) genomic DNA. The PCR products were cut with XbaI and HindIII, and inserted into the same restriction sites of genomic clone SCH25 containing a 2.5 kb HindIII fragment of the DWF4 DNA corresponding to the 3' half of the gene. The resulting recombinant DNA clone pD4CDS, containing the whole coding sequence from the translation initiation site to 694 by downstream of the stop codon, was cut with XbaI and transferred to an overexpression vector pART27 (Gleave (1992), *Plant Molec. Bio.* 20:1203-1207). The resulting binary construct was named POD4. This construct was introduced into *Agrobacterium* through electroporation.

B. Spray Transformation

Since it has been shown that *Agrobacterium*-mediated transformation can work by seed infection (Feldmann and Marks (1987) *Molec. Gen. Genet.* 208:1-9) or by simply dipping the host plants into *Agrobacterium* culture, we decided to try spraying the *Agrobacterium* directly onto the plants. In addition to spraying, the "floral dip" method was used as described (Clough and Bent (1998), infra). About 20 Wassilewskija-2 (Ws-2) wild-type and dwf4-4 seeds were sprinkled on 10 cm pots, and thinned to 5-6 plants per pot 10 days (wild type) and 20 days (dwf4-4) after germination. When the primary inflorescences of the wild type reached 3-4 cm in height, they were decapitated to induce axilary bolts. dwf4-4 plants were used without decapitation. For the preparation of *Agrobacterium*, a single colony selected on 20 μg/ml kanamycin in Luria-Bertani (LB) medium (10 g bacto-tryptone, 5 g bacto-yeast extract, 10 g NaCl per liter, pH7) was inoculated into 100 ml liquid LB media, and grown for 3 days. One $OD_{600}$ unit equivalent cells were used to inoculate 100 ml LB media. The overnight grown cells were collected by centrifugation, and resuspended with transformation media as described in Clough and Bent (1998), infra (5% sucrose and 0.05% Silwet L-77, ($OD_{600}$=1). The *Agrobacterium* suspension was sprayed onto plants on the third day after decapitation. To avoid physical contact with possibly hazardous Silwet vapor, protective glasses were used and the spraying was done in a fume hood. To test the efficiency of repeated spraying, plants were sprayed every third day (3×). Sprayed plants were grown to maturity and seeds harvested. For seed sterilization 0.07 g seeds were surface sterilized by treating for 2 min in 70% ethanol, 15 min in bleach solution consisting of 5% Clorox and 1% SDS, followed by three rinses with sterile water. To plate the seeds 25 ml of sterile top agar (0.15% agar) was added to the sterilized seeds and the seed mixture was poured onto Murashige and Skoog solid plate (100×15 mm, Murashige and Skoog salts, 5% sucrose, 0.08% agar, pH6) supplemented with kanamycin or hygromycin at 60 μg/ml and 40 μg/ml, respectively. Twelve days after germination kanamycin resistant were transferred to single pots, and grown to maturity. T2 seeds were collected from individual transformants (T1), and plated again on the selection media to determine segregation ratios for drug-resistant versus sensitive plants. *Arabidopsis* transformants were named *Arabidopsis* Overexpressor of DWF4 (AOD4) when harboring an overexpression construct pOD4, and DWF4-promoter: GUS (D4G) for transformants containing a GUS fusion gene. Homozygosity for the transgene was determined when no sensitive T4 seedlings segregated from >500 T3 individuals. Morphometric analysis of AOD4 lies and GUS histochemical analysis of D4GL plants was performed using plants homozygous for the transgene.

For histochemical analysis of the D4GL plants, seeds were plated on M&S plates and grown in the dark and light. Seedlings were harvested at the designated dates and stained overnight using a substrate mixture (0.1 M $NaPO_4$, pH 7, 10 mM EDTA, 0.5 mM $K_3Fe(CN)_6$, 0.5 mM $K_4FE(CN)_6$, 1 mM X-glucuronide, and 0.1% Triton X-100). Seedlings cleared with 90% ethanol were rehydrated before taking pictures using a Stemi SV11 dissecting microscope (Zeiss, N.Y.).

Transgenic tobacco plants (TOD4) harboring the pOD4 constructs were produced in the plant tissue culture laboratory at the University of Arizona. Protocols for the regeneration of transgenic plants from lead discs of *Nicotiana tabacum* var *Samsun* will be provided on request. Fifteen independent transformants for both the control and OD4 constructs were grown fro seeds. Morphological analysis of the TOD4 lines was performed using T2 plants in the course of growth for 4 months in the green house (30° C.). Methods for *Arabidopsis* growth and RNA gel blot analysis were previously described herein. Briefly, seeds of wild type and the two AOD4 lines were germinated on M&S agar media. 10 days after germination, 20 seedlings confirmed to be resistant to kanamycin were transferred to a single pot. Various morphological traits (Table 3) were measured. To determine the seed production, after 8 weeks from germination, plants were further dried for two weeks at room temperature. Seeds were harvested from an individual plant and weighted. To measure the seed size, seeds were magnified 3 times under the dissecting microscope, the width and the length of five seeds from each plant were measured to the nearest tenth of mm.

C. DWF4 Transcription is Localized to Zones of Cell Division and Elongation

To localize BR biosynthesis, RNA gel blot analysis with total RNA isolated from nine different tissues of three-week old plants was performed. The DWF4 transcript was barely detectable in shoot tips, roots, dark-grown seedlings, callus and axilary buds, but the levels were below the detectable limit in the other tissues examined, including stems, siliques, pedicels, and rosette leaves. For finer localization of the expression, the expression of the GUS reporter gene controlled by the DWF4 promoter was examined.

Prior to performing DWF4-promoter:GUS gene fusion analysis, a 1.1 kb fragment of DNA upstream of the DWF4 translation start site was tested to ensure that it contained all of the necessary sequence elements for proper transcriptional control of DWF4. dwf4-4 plants were transformed with a 4.8 kb construct consisting of a 1.1 kb promoter region and 3.7 kb that contained the complete DWF4 coding sequence. For *Agrobacterium*-mediated transformation of *Arabidopsis* plants, a "spray transformation" protocol was employed rather than traditional methods. Spray transformation yielded a comparable number of transformants relative to the traditional "floral dip" (Clough and Bent (198) *Plant J.* 16:735-743) or "vacuum infiltration" methods (Bechtold et al. (198) *Methods Mol. Biol.* 82:259-266). Interestingly, repeated spraying resulted in an increased number of transformants. Transformants harboring the DWF4 genomic DNA displayed a wild type phenotype, suggesting that the promoter segment contained the necessary information for proper expression of the gene.

For histochemical staining analysis of transgenic plants harboring the DWF4-promoter::GUS(D4G) recombinant gene, two different D4G constructs were made and tested. D4GL contained the 1.1 kb promoter fragment, whereas D4GS carried only a TATA-like promoter region (280 bp). GUS staining in 20 independent transformants containing D4GS was either not detected or inconsistent between transformants. However, the 20 transgenic plants containing D4GL displayed a consistent GUS staining pattern, suggesting that the 1.1 kb promoter is required for the proper transcriptional control of DWF4.

Analyses of GUS staining patters in T2 plants homozygous for D4GL revealed that GUS activity was present in tissues with actively dividing or elongating cells. These include shoot apical meristems, leaf primordia, collet (the junction between hypocotyl and root), and root tips, including lateral root primordia, as shown in 6-day old light-grown seedlings. Interestingly, dark-grown seedlings displayed GUS activity in cotyledons whereas the staining was not detectable in the cotyledons of light-grown seedlings. In adult plants, GUS activity was detected in floral primordia, carpels, and the basal end of the filaments of unopened flowers, whereas GUS activity in sepals, petals, and mature pedicels was not detected. The shoot tips, bases of emerging branches, and primordia of axilary inflorescences were GUS positive, whereas elongated internodes were native. Embryos in the seeds of the fully elongated siliques were weakly positive for GUS staining, suggesting a role for BRs in embryo development. Leaf primordia, young leaves, expanding leaf margins, and the base of petioles displayed GUS activity, but old leaf blades were negative for GUS staining The tissues positive for GUS staining confirmed the expression pattern examined by northern analysis with the tissue-specific RNA.

Since DWF4 is proposed to be a key enzyme in the BR biosynthetic pathway, DWF4 transcription could be regulated by an end-product feedback mechanism. To this end, D4GL was expressed in different genetic backgrounds including two BR deficient mutants, dwf7-1 and dwf8-1, and a BR-enriched line, AOD4. GUS activity was increased in dwf7-1 and dwf8-1 but decreased in AOD4 lines. DWF7 is a C-5 desaturase that acts in the sterol specific part of the pathway. D4GL activity in dwf7-1 was found in the same tissues as wild type but, dwf8-1 is defective in a BR biosynthetic step downstream of CPD. In dwf8-1 is defective in a BR biosynthetic step downstream of CPD. In dwf8-1, the intensity of the D4GL activity was noticeably stronger as compared to wild type but the expression patterns were relatively diffuse. dwf8-1 was also found to express GUS at nascent sites as compared to wild type. In wild type, D4GL expression in the cotyledons of light-grown seedlings was not detected, but dwf8-1 displayed considerable D4GL activity in the cotyledons. Also in contrast to wild type, GUS activity was detected throughout the hypocotyls of dwf8-1 light-grown seedlings, suggesting that D4GL transcription is upregulated in dwf8-1 in a more general manner. Conversely, GUS activity was greatly reduced in AOD4-4 plants. Also, in AOD4 plants GUS activity in the root tip and collet was completely eliminated, whereas the shoot tip retained residual activity, suggesting that increased levels of BRs in AOD44 may have results in lower GUS activity. The down-regulation of GUS activity was similarly found if D4GL plants were exogenously supplied with $10^{-6}$ M24-epibrassinolide (epi-BL). Seedlings treated with epi-BL displayed greatly reduced GUS activity in tissues normally stained in untreated control plants, suggesting that exogenously applied epi-BL effectively down-regulates D4GL activity. However, hypocotyls of D4GL plants supplemented with $10^{-4}$ M $GA_3$, while longer than controls, did not display an increase in GUS staining in shoots and roots. This suggests that $GA_3$ or $GA_3$-induced elongation did not affect ID4GLI transcription in these tissues.

D. DWF4 Overexpression Results in Elongated Hypocotyls in *Arabidopsis* and Tobacco Seedlings A DWF4 overexpression construct (pOD4) was made by placing the DWF4 genomic DNA under the control of the CaMV 35S promoter. RNA gel blot analysis, with total RNA isolated from the transgenic lines containing the overexpression construct, showed that DWF4 transcripts were greatly increased in both *Arabidopsis* and tobacco, whereas the level was not readily detectable in either wild type or in dwf4-1 plants. Similar to increased mRNA transcripts, the 80 independent AOD4 transgenic plants had longer hypocotyls and inflorescences.

To compare the phenotypic effects resulting form the endogenous and exogenous addition of BRs, the length of roots and hypocotyls of 16 seedlings of dwf4, wild-type controls, wild-type plants supplemented with $10^{-6}$ M epi-BL, and two independent AOD4 lines, grown for 12 days in the light or dark was measured. As described herein, dwf4-1 displayed greatly reduced hypocotyl length both in the light and dark as compared to wild type. Wild-type roots are shortened when grown in the dark, but dwf4-1 root length was not significantly reduced in the dark compared with the reduction in hypocotyl length. When epi-BL is added, light-grown wild type seedlings developed elongated hypocotyls, whereas roots were shorter than untreated control plants. These characteristic responses of wild-type plants to epi-BL treatment were similar in two independent AOD4 lines. The hypocotyl length of light-grown AOD4 seedlings was comparable to that of seedlings treated exogenously with epi-BL. However, dark-grown hypocotyls showed a dramatic increase in length as compared to controls with our without epi-BL. Inhibition of root growth was also obvious in the AOD4 lines. Furthermore the increased hypocotyl length and reduced root length were consistently observed in 15 independent transformants of tobacco (TOD4) harboring a pOD4 construct. This results suggests that the *Arabidopsis* DWF4 enzyme also catalyzes BR biosynthesis in tobacco.

E. DWF4 Overexpression Results in Increased Plant Height, Bigger Leaves, and Increased Seed Production As shown in Table 3, the effects of DWF4 overexpression on plant growth were monitored during the course of development. The number of rosette leaves at bolting was not significantly different between wild-type and AOD4 plants (Table 3). The inflorescence height of wild type and two independent AOD4 liens were comparable 20 days after germination (DAG). Later, the AOD4 lines outgrow wild type. Surprisingly, AOD4 lines continue to grow beyond 35 DAG at the time wild-type plants ceased elongation. At maturity, the height of AOD4 lines was 135% (AOD4-65) and 142% (AOD4-73) that of wild type, respectively. Similarly TOD4 also displayed a 14% increase in plant height as compared to the control. Interestingly, the increased inflorescence length in AOD4 plants seemed to be at the cost of stem stiffness. During development, AOD4 plants tend to fall over earlier than the Ws-2 wild type. In addition to plant height, comparison of rosette leaf size between wild type and $AOD_4$ indicates that leaves, both rosette and cauline, are larger, specially in adult plants. TOD4 plants also possessed leaves that were larger, and had longer petioles relative to the control. Furthermore, additional secondary branches were found both in *Arabidopsis* and tobacco overexpression lines. In AOD4 plants, this additional branching was associated with >2 times increased number of siliques per plant, leading to a 33 and 59% increase in seed production (Table 3). The increased seed production in the AOD4 lines was mainly due to the increased number of seeds per plant than increase in the seed size, because the size was not significantly increased (Table 3). In addition to the increased number of seeds, the length of siliques as well as the length of an internode between the first siliques in a main inflorescence and the base of plant was increased (Table 3).

Figure 8:
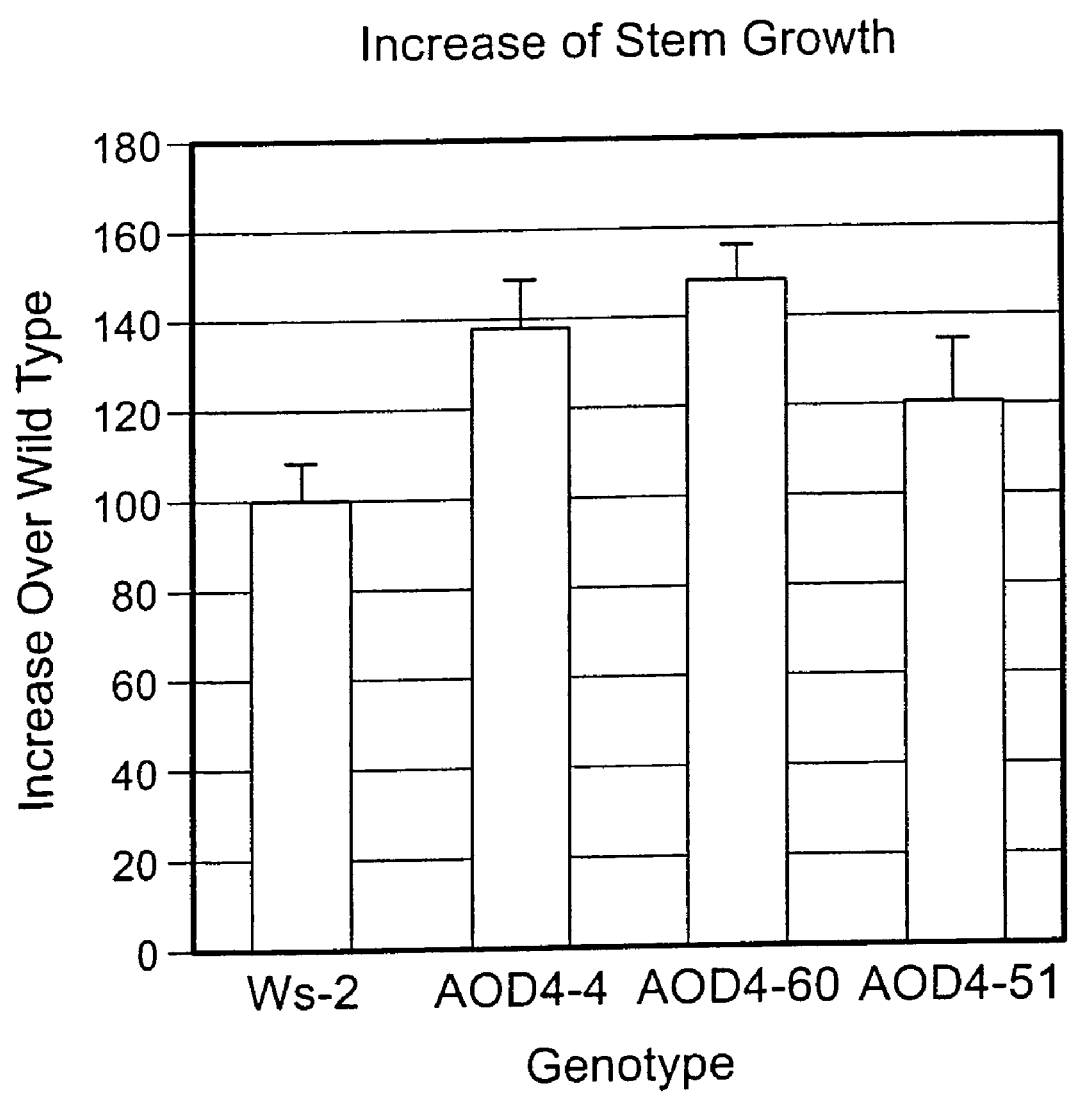
FIG. 8 depicts the increase in inflorescence growth of three transformants which overexpress dwf4 as compared to wild type (Ws-2). The length of inflorescences of DWF4 overexpression lines increased ore than 20% compared to that of wild type. The length of the plant was measured at maturity. Each date point is a mean value of more than 9 plants, except AOD4-60 which represents 2 plants.
Figure 9:
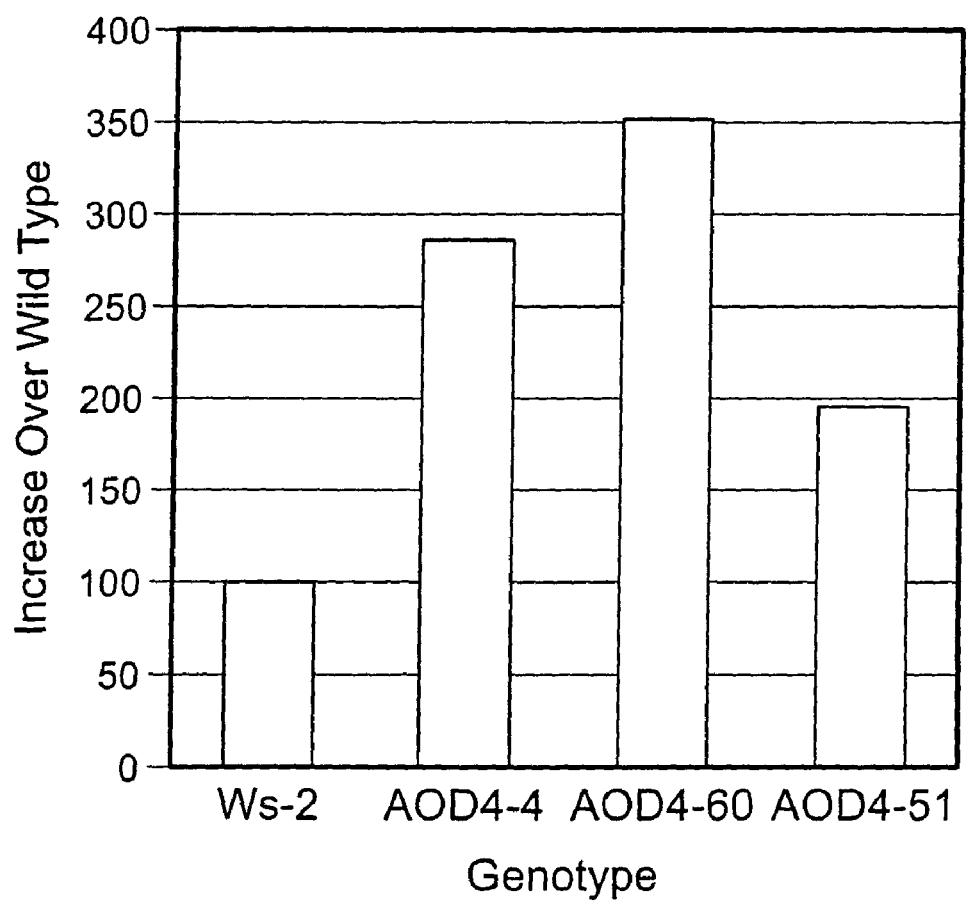
FIG. 9 depicts the increase in seed production of three transformants which overexpress dwf4 as compared to wild type (Ws-2). Seeds were harvested from individual plants of each genotype (n>5). Seeds from each plant were weighed and a mean value calculated. The Figure shows percent increase over wild type.
Figure 12:
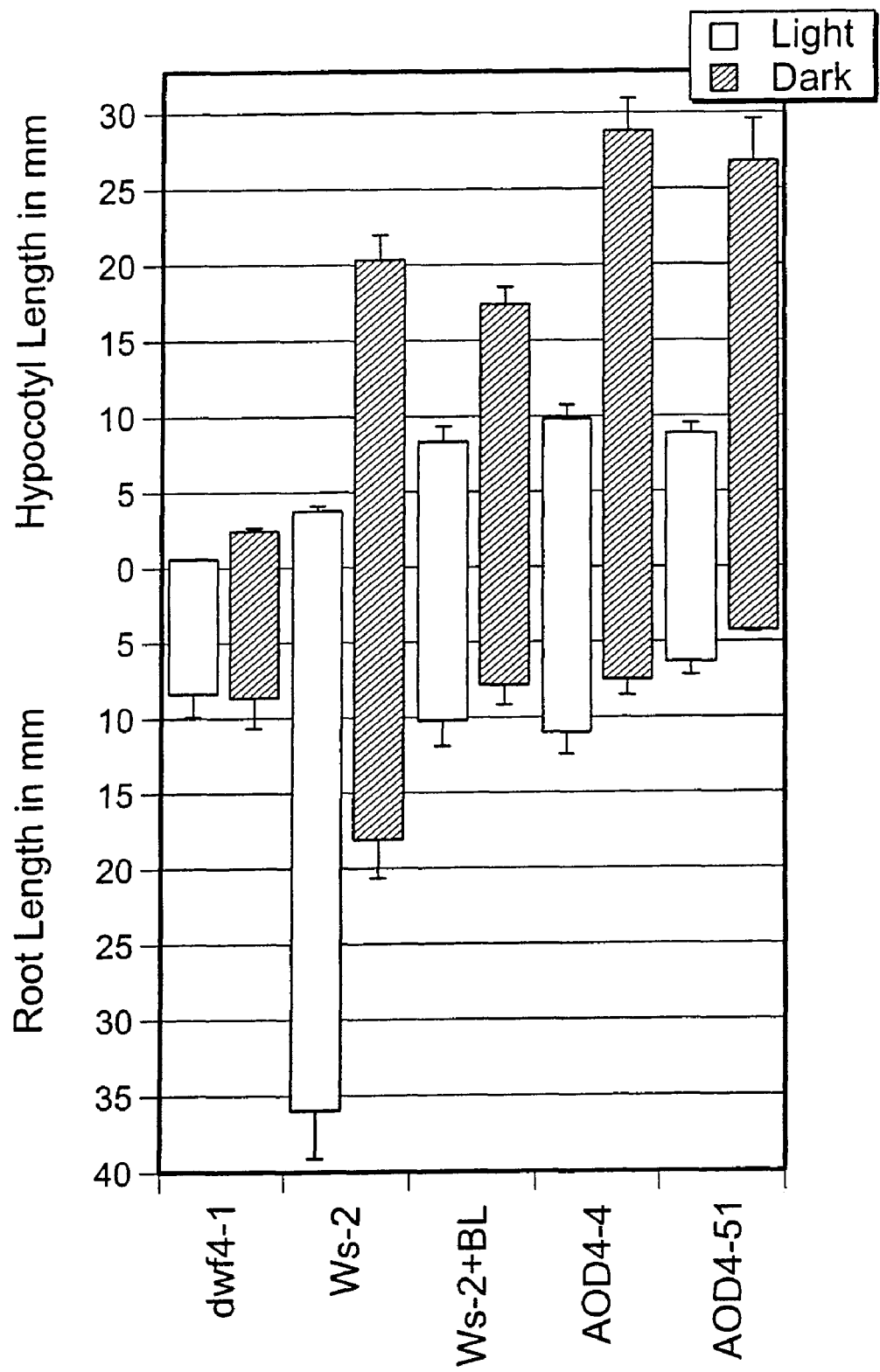
FIG. 12 depicts seedling phenotypes of twelve-day-old dwf4-1, wild type, epi-BL-treated wild type, and AOD4 lines grown in the light and dark, particularly quantification of hypocotyl and root growth. The average lengths of 16 seedlings are displayed with the standard deviation. Increased BR concentration supplied exogenously or endogenously resulted in both elongated hypocotyls and shortened roots.

FIG. 8 shows that stem growth is increased more than 20% compared to wild type in DWF4 overexpression lines and FIG. 9 shows that seed production is increased significantly over wild type in the DWF4-overexpressed lines. FIG. 12 depicts hypocotyl length and root length in light and dark. Further, the height of AOD4 lines was greater than wild type over the days examined. In addition, although wild type plants ceased growth around five weeks after germination, AOD4 plants continued to grow up to seven weeks.

TABLE 3

Morphological comparison among control and AOD4 lines.

| | WS-2 | AOD-65 | AOD-73 | Percent increase over Ws-2 | |
| --- | --- | --- | --- | --- | --- |
| | | | | AOD4-65 | AOD4-73 |
| Size | | | | | |
| Height in cm[1] | 11.4 ± 1.8 | 15.4 ± 3.3 | 16.8 ± 3.8 | 135 | 147 |
| Silique in mm | 13.7 ± 2.0 | 18.4 ± 2.5 | 20.0 ± 3.2 | 134 | 145 |
| Seed length in mm | 0.47 ± 0.04 | 0.51 ± 0.05 | 0.49 ± 0.03 | 108 | 105 |
| Seed width in mm | 0.29 ± 0.03 | 0.32 ± 0.03 | 0.3 ± 0.03 | 110 | 102 |
| Number | | | | | |
| Rosette | 5.1 ± 0.5 | 5.2 ± 0.4 | 5.7 ± 0.5 | 100 | 112 |
| Branch[2] | 9 ± 3 | 23.4 ± 5.7 | 21.6 ± 6.8 | 260 | 240 |
| Siliques | 106.7 ± 33.6 | 373.5 ± 107.5 | 344.2 ± 47.1 | 350 | 325 |
| Seed production[3] (mg/plant) | 164 ± 48 | 218 ± 33 | 261 ± 37 | 133 | 159 |

[1]Between rosette and the first siliques (N > 12)
[2]Number of branches bearing siliques (N > 12)
[3]Weight of seeds per individual plant (N > 12)

Thus, the DWF4 locus is defined by at least four mutant alleles. One of these is the result of a T-DNA insertion. Plant DNA flanking the insertion site was cloned and used as a probe to isolate the entire DWF4 gene. Sequence analysis revealed that DWF4 encodes a cytochrome P450 monooxygenase with 43% identity to the putative *Arabidopsis* steroid hydroxylating enzyme CONSTITUTIVE PHOTOMORPHO-GENESIS AND DWARFISM. Sequence analysis of two other mutant alleles revealed deletions or a premature stop codon, confirming that DWF4 had been cloned. This sequence similarity suggests that DWF4 functions in specific hydroxylation steps during BR biosynthesis. The dwarf phenotype can be rescued with exogenously supplied brassinolide. dwf4 mutants display features of light-regulatory mutants, but the dwarfed phenotype is entirely and specifically brassinosteriod dependent; no other hormone can rescue dwf4 to a wild-type phenotype. Feeding studies utilizing BR intermediates showed that only 22α-hydroxylated BRs rescued the dwf4 phenotype, confirming that DWF4 acts as a 22α-hydroxylase. In adult plants, strong GUS staining (indicative of dwf4 expression) was found in the primordia of axilary inflorescences and secondary branches, and in young developing flowers. GUS expressing tissues correspond to the tissues sensitive to exogenously applied BRs leading to the hypothesis that these tissues are putative brassinolide biosynthetic sites. The inflorescence height of DWF4 overexpressing lines increased >35% in *Arabidopsis* (AOD4) and 14% in tobacco (TOD4) as compared to control plants at maturity. The total number of branches and siliques increased >2-fold in AOD4 plants, leading up to a 59% increase in seed production. The phenotypes of dwf4, DWF4, and AOD4 plants suggest that the degree of DWF4 transcription is associated with the degree of BR effects. In sum, it appears be possible to engineer agricultural plants with increased biomass and seed yield.

What is claimed is:

1. A transgenic plant comprising at least one exogenous polynucleotide, said exogenous polynucleotide comprising a control element linked to a nucleic acid encoding a CYP90B cytochrome P450 polypeptide.

2. A transgenic plant prepared by a process comprising introducing into a plant cell at least one polynucleotide comprising a control element operably linked to a nucleic acid encoding a cytochrome P450 CYP90B polypeptide, under conditions wherein said plant cell is transformed, and growing said plant from said transformed plant cell.

3. The plant of claim 1 or 2, wherein said plant is a monocot.

4. The plant of claim 1 or 2, wherein said plant is a dicot.

5. The plant of claim 1 or 2, wherein said control element directs expression in vegetative tissue of said plant.

6. The plant of claim 1 or 2, wherein said control element directs expression in leaf tissue.

7. A transgenic plant cell comprising at least one exogenous polynucleotide, said exogenous polynucleotide comprising a control element linked to a nucleic acid encoding a CYP90B cytochrome P450 polypeptide.

8. The plant cell of claim 7, wherein said plant cell is from a monocotyledonous plant.

9. The plant cell of claim 7, wherein said plant cell is from a dicotyledonous plant.

10. The plant cell of claim 7, wherein said control element directs expression in vegetative tissue of a plant.

11. The plant cell of claim 10, wherein said vegetative tissue is leaf tissue.

12. A cultured plant tissue comprising a transgenic plant cell, said transgenic plant cell comprising at least one exogenous polynucleotide, said exogenous polynucleotide comprising a control element linked to a nucleic acid encoding a CYP90B cytochrome P450 polypeptide.

13. The plant tissue of claim 12, wherein said transgenic plant cell is from a monocotyledonous plant.

14. The plant tissue of claim 12, wherein said transgenic plant cell is from a dicotyledonous plant.

15. The plant tissue of claim 12, wherein said control element directs expression in vegetative tissue of said plant.

16. The plant tissue of claim 15, wherein said vegetative tissue is leaf tissue 1.

* * * * *

SEQUENCE LISTING

```
<160> NUMBER OF SEQ ID NOS: 30

<210> SEQ ID NO 1
<211> LENGTH: 6888
<212> TYPE: DNA
<213> ORGANISM: Arabidopsis thaliana

<400> SEQUENCE: 1
atgtgggtat tatattgttg ggttcggttt gagctacaat ataaatttcg tgtttctggt      60
tattctgttc acatgatttg agtttggttc tcaatttgga ttccaagata attaaatatt     120
aaaattcatt taaaatattt acaagtaatt aattatcttt acattgtatt gttataacaa     180
aatatctatc tttggtatat gagaaaatat ggagtttgga atttataata ataaaggaaa     240
taatcgattc catttggttg gattacacag ttaagttttt gtgtttcttt tgttatatgt     300
atatgagtaa atcaaaaaga gtattgattg aagtgtaaac atatttcgtt atgacccca      360 aaaaaaaaaa aaaaacaaac aaacaaaccc cccccgat  atagtttttg gttctggatt     420
aggtttattt gatcataatt acatgcatca tttctttgat tactatgaag attttcttac     480
caattaaaat ttcgaattca tatctcttga ttattaaatt aaatacgagt gtgaatatcc     540
```

```
gtttatcgat cactccaatc atgattatga ttcttgtgct aatccagcaa attattaaca    600
agagtattga gaaaaaaccg aaaataagaa aagggaaaga gtagtgaccc atggagtatg    660
tgaataatta tcaaagagaa taagagatga caaccaaaag gttgtggaat aatggtccct    720
gccagctttc tctcacaatc aatatcgacc ctatttggat tttctggata ttcgttaaaa    780
tttgcgataa cgattgtgaa aaatatttta tttgttagct gatctcaata ttatgttcca    840
ggtatttgca taatcttctg tttaaagcat attttgtctt tcttttgtt tcgtttctct      900 taactatata ttatcgcgga tatatgataa caatgatata tcacaaaaca attgtctggg    960
accattttga ataaactttt tctcaaacat tacgggacac tggactcgac ccttaaaata    1020
cgattttaca gcgtcactag ttgagattac tagcataaag cataaaggac ccgttcaagc    1080
tatttataca aagttacaaa ctgaatatag cttgaaatcc tttagaaaat tttggaatta    1140
ccggttgtta tgtaaatata gatttagtgg taaacaaata tgttaatcaa ttagtggtca    1200
acatatacat aattccttac agaaaaaaca aacttaagag aagttaacat atccatatat    1260
gggtatgcta tacctttcac gtatgctata ctagagacta agaatagtt atgtgatgtc      1320 gataaatgaa attcacacgc gtggtaataa ttatgggacc gtatgttacg atcactgcaa    1380
atatcattct tggttggtca acaataaaaa caaaaacaag aaaaaaagaa aacgattttt    1440
cttggattcc attcaatgat ctaaaatgca tagatctttt gggttacagt ttcgaagtcc    1500
tctacaagcg tgtaaccatc tgcaactatt aaattgcttt ctttaatgca tctttaacat    1560
atttattgtt agttggaatt taataagagc gaacttgtaa cattacaata tttatattag    1620
atactagtat gtgattattc caaatacata ctttggatgt ttaaacttaa tcttgtttct    1680
tcctacggta taaatattaa tcatcgaggt aaaaaaagtt ttgtcttatt ttcgcgatgc    1740
atgaaggata aacctaatga ctttaatttt ttgaaaatgt aacccttta ctcatagatt      1800 aattaccgta tgttttttgtt gccataatga cagcctctac aactgtgata gtcaattttt    1860
tctgcaaata ttaaattagg aattcaatgc tactatcaat agaagaaaca gctgagtatt    1920
acattttaat ttaaagacaa aatttttgaa aaatgttata atttctaaca atattattaa    1980
aatatgatgc ctataatgta tttcctatgt tcttaaaata tttttttta tatttagtta      2040 taaatacatt atgaaccaat aatagttggt gaattcaaat atctccatta atatttttg      2100 aaatctacaa attattaata tttagtcaat aacaatgcat agaaagttcc aaaaaaaatt    2160
ttgttaacag aaacttccaa atttttttt tttatggaac aagaaataac agatagaaaa      2220
ctattttgtt gtggaatgga agtagtaata tacattaagc aaatttttaaa aaattatata    2280 agcctatacg cgctcaaagt atgttatcta gtaggtgtaa ttaataatgc atggtgcgat    2340
tcagaattgg gacaacaatg aaaacggaat taaaatatta actttaaaat aaataaaaat    2400
ttgagtaaat gtgttttctg actattgagg ggcaaaaaaa agacaatgcc aaaagtctac    2460
gggtttgact gtccagttcg gtaataatct aataactctg tctttgaccg cacgctcgtg    2520 tagggtcct tctgacattt tcactgttct accccctactc gtgagcccac ccttttccca    2580
tatcctaagg gtaattttgg aaatcccaat ttaaaccgat tgagaccgta ccggacttcc    2640
tgggattctg ctggagcatt tatcaaaaat tattagcacg aatgggttta ttaatttaaa    2700
aactcacaac ttgatcagat aaaatttcat aaacactttt acgatggatt cgtacgatct    2760
atctaatgac ttttttttt ctaccacggt ggatgaaagt tatagtacta ttagccagag      2820
acaattgatt atagatatat ccattaatcc atgatattta tgatataaat agctgttaaa    2880
ctatttcagc atcgcagctt tctgcaactt ttgttttaa tttaagagtt taataaataa      2940
```

```
aagtattaaa aggagcataa cgaggcaaca aaagtaatga acacggagaa acaaaagcca   3000
tgaagctcat tggttagttt aagcttaata agaagatttt attaaatttt aatgacgatg   3060
ataacaatta tattttctga cttctttaaa acccctctt acaaacagaa gctccctttt    3120
tcagtagaag tccgattccc aatcttaaag acaaagccat tagaaagaga aagtgagtga   3180
gagagagaga gaaactagct ccatgttcga aacagagcat catactctct tacctcttct   3240
tcttctccca tcgcttttgt ctcttcttct cttcttgatt ctcttgaaga gaagaaatag   3300
aaaaaccaga ttcaatctac ctccgggtaa atccggttgg ccatttcttg gtgaaaccat   3360
cggttatctt aaaccgtaca ccgccacaac actcggtgac ttcatgcaac aacatgtctc   3420
caagtaaaca acaacatctt ccaaaaactc aaaaaaataa atcctctgtt tttgaaattt   3480
gactaatgtt gtttatttta caggtatggt aagatatata gatcgaactt gtttggagaa   3540
ccaacgatcg tatcagctga tgctggactt aatagattca tattacaaaa cgaaggaagg   3600
ctctttgaat gtagttatcc tagaagtata ggtgggattc ttgggaaatg gtcgatgctt   3660
gttcttgttg gtgacatgca tagagatatg agaagtatct cgcttaactt cttaagtcac   3720
gcacgtctta gaactattct acttaaagat gttgagagac atactttgtt tgttcttgat   3780
tcttggcaac aaaactctat tttctctgct caagacgagg ccaaaaaggt ttttattttt   3840
atcttttatt ttgctaaatt ttttgtttta tgaatcttta gagtttctaa cttttttttt   3900
tttaattgaa cagtttacgt ttaatctaat ggcgaagcat ataatgagta tggatcctgg   3960
agaagaagaa acagagcaat taagaaagaa gtatgtaact ttcatgaaag gagttgtctc   4020
tgctcctcta aatctaccag gaactgctta tcataaagct cttcaggtac atttattttt   4080
ttttgctgta aagtcacaaa ctctcattat aggttttaa ttttatttta tgtgttaaat    4140
aaaatatcta aaatggttgt gtagtcacga gcaacgatat tgaagttcat tgagaggaaa   4200
atggaagaga gaaaattgga tatcaaggaa gaagatcaag aagaagaaga agtgaaaaca   4260
gaggatgaag cagagatgag taagagtgat catgttagga aacaaagaac agacgatgat   4320
cttttgggat gggttttgaa acattcgaat ttatcgacgg agcaaattct cgatctcatt   4380
cttagtttgt tatttgccgg acatgagact tcttctgtag ccattgctct cgctatcttc   4440
ttcttgcaag cttgccctaa agccgttgaa gagcttaggg taagataatt ataacagcac   4500
aagttaatta ctaccaaatt gttacgtatt atataagtta ttatagaatt attctattag   4560
aatatacgat gaaaaagta tgtatattta attgtcacta attttatgtt tattgattta    4620 tactttgaa ggaagagcat cttgagatcg cgagggccaa gaaggaacta ggagagtcag    4680
aattaaattg ggatgattac aagaaaatgg actttactca atgtgtatgt tactatcatt   4740
ctcattattt attctatgtt catatgattt atgatgaaac caaaattatt gattttttt    4800 ttggtgtgtg tgaaggttat aaatgaaact cttcgattgg gaaatgtagt taggttttg    4860 catcgcaaag cactcaaaga tgttcggtac aaaggtaaaa ctttacgtac aaaattttta   4920
aataatgaaa tccggaatat tgaaatctta ttggatgaaa aatattaaaa taatttacat   4980
ttcttaatgt tggaaaaaag gatacgatat ccctagtggg tggaaagtgt taccggtgat   5040
ctcagccgta catttggata attctcgtta tgaccaacct aatctcttta atccttggag   5100
atggcaacag gtaaataaaa agtttctctc gttaactatc gaaaattagt gtatagtttt   5160
ttcatctatt gcatgaatag atacgtccta cgtgatttac ctatctatag atactatacg   5220
agaactatta atctggcaaa aacttttat tattattatc tttcaagtta gatcttaaca    5280
cgtcatggat cattgatcac atgaaagcat ataaattaaa aataagagag agaaagagac   5340
```

-continued

```
gtgttggtgt aagtgtacgt gaagacaatt aattagtagg atggtatgtc tttaatgacg    5400
taggagctgc ctaaatattc ttataatcgt gaccgttgat ttattattag tcacggcttt    5460
gatacaattt aagatttgac ggacgatggt accacggctt tgacggatct cacacgcccg    5520
atgacttgta cgtgcgttag attctgccac gttgactggt tttaatactt agatttataa    5580
ctctattaat tataacaact atcaaatcgg cgaattagag aaatatacta tatagtatta    5640
ttatgattat tatgagataa tactttatga aataagataa taatggtagt catgatgtta    5700
tagtgagtgg ggaaggtaag aggtggtgag agatgattaa tgaccccacg tggtgtggtg    5760
ccaacaagca cgtgttcttc ttccttttt cttcccaact tctttttttg ggggtttatt    5820
gtgatttata aaatcggttt gtcgtttttt tttgtgacga gcagcaaaac aacggagcgt    5880
catcgtcagg aagtggtagt ttttcgacgt ggggaaacaa ctacatgccg tttggaggag    5940
ggccaaggct atgtgctggt tcagagctag ccaagttaga aatggcagtg tttattcatc    6000
atctagttct taaattcaat tgggaattag cagaagatga tcaaccattt gcttttcctt    6060
ttgttgattt tcctaacggt ttgcctatta gggtttctcg tattctgtaa aaaaaaaaa    6120
agatgaaagt attttattc tcttcttttt ttttgataa ttttaaatca ttttttttgc    6180
ccaatgatat ataaaaattt ggataaataa tattattgga tattcgtttt ttagttcggg    6240
tttgagaaaa gggtttcgac tttcgaaagt ggacgatgta tatagattgg gagctaggtt    6300
gagtctttgg acatttgtat tggatgttgt tgattattag tgtcgacact attaaacctt    6360
aaatgggctt tctataaggc ccaattatat tacgattata acaaagtgac aacttttact    6420
tcgtttttga tccgaagcaa taacaaattg tcaaatacca acacaagaa ttatgtaaac    6480
actcgtgtgt gtctagtggg aaatcattgg gctggagact gaacatcaga acacaagaaa    6540
cctgtcaatt atggatacac ctcctatgac ggtttccaaa ctttatcttg attcttatcg    6600
tgttacattg acacaaagag ttaggtgtca aaaggactaa atgaataaca atagctctca    6660
ggataagaag gttcataaaa tggtttcttt attttgagaa gaaagagaga ggagctttta    6720
ctgtttcttg ggtcctattc cttaaatga gagggtttcg ttttacttc ttctatctca    6780
tcatctttag gatcctcttc tagacgagta aagtaatcct cgttaccaag caatggtctc    6840
atcttttgaa gacaggtctt ttccaagtcc tagttcaggc caaagctt                 6888
```

<210> SEQ ID NO 2
<211> LENGTH: 513
<212> TYPE: PRT
<213> ORGANISM: Arabidopsis thaliana

<400> SEQUENCE: 2

```
Met Phe Glu Thr Glu His His Thr Leu Leu Pro Leu Leu Leu Leu Pro
  1               5                  10                  15

Ser Leu Leu Ser Leu Leu Leu Phe Leu Ile Leu Leu Lys Arg Arg Asn
             20                  25                  30

Arg Lys Thr Arg Phe Asn Leu Pro Pro Gly Lys Ser Gly Trp Pro Phe
         35                  40                  45

Leu Gly Glu Thr Ile Gly Tyr Leu Lys Pro Tyr Thr Ala Thr Thr Leu
     50                  55                  60

Gly Asp Phe Met Gln Gln His Val Ser Lys Tyr Gly Lys Ile Tyr Arg
 65                  70                  75                  80

Ser Asn Leu Phe Gly Glu Pro Thr Ile Val Ser Ala Asp Ala Gly Leu
                 85                  90                  95

Asn Arg Phe Ile Leu Gln Asn Glu Gly Arg Leu Phe Glu Cys Ser Tyr
            100                 105                 110
```

Pro Arg Ser Ile Gly Gly Ile Leu Gly Lys Trp Ser Met Leu Val Leu
        115                 120                 125

Val Gly Asp Met His Arg Asp Met Arg Ser Ile Ser Leu Asn Phe Leu
130                 135                 140

Ser His Ala Arg Leu Arg Thr Ile Leu Leu Lys Asp Val Glu Arg His
145                 150                 155                 160

Thr Leu Phe Val Leu Asp Ser Trp Gln Gln Asn Ser Ile Phe Ser Ala
                165                 170                 175

Gln Asp Glu Ala Lys Lys Phe Thr Phe Asn Leu Met Ala Lys His Ile
            180                 185                 190

Met Ser Met Asp Pro Gly Glu Glu Thr Glu Gln Leu Lys Lys Glu
        195                 200                 205

Tyr Val Thr Phe Met Lys Gly Val Val Ser Ala Pro Leu Asn Leu Pro
    210                 215                 220

Gly Thr Ala Tyr His Lys Ala Leu Gln Ser Arg Ala Thr Ile Leu Lys
225                 230                 235                 240

Phe Ile Glu Arg Lys Met Glu Arg Lys Leu Asp Ile Lys Glu Glu
                245                 250                 255

Asp Gln Glu Glu Glu Val Lys Thr Glu Asp Glu Ala Glu Met Ser
            260                 265                 270

Lys Ser Asp His Val Arg Lys Gln Arg Thr Asp Asp Leu Leu Gly
        275                 280                 285

Trp Val Leu Lys His Ser Asn Leu Ser Thr Glu Gln Ile Leu Asp Leu
    290                 295                 300

Ile Leu Ser Leu Leu Phe Ala Gly His Glu Thr Ser Ser Val Ala Ile
305                 310                 315                 320

Ala Leu Ala Ile Phe Phe Leu Gln Ala Cys Pro Lys Ala Val Glu Glu
                325                 330                 335

Leu Arg Glu Glu His Leu Glu Ile Ala Arg Ala Lys Lys Glu Leu Gly
            340                 345                 350

Glu Ser Glu Leu Asn Trp Asp Asp Tyr Lys Lys Met Asp Phe Thr Gln
        355                 360                 365

Cys Val Ile Asn Glu Thr Leu Arg Leu Gly Asn Val Val Arg Phe Leu
    370                 375                 380

His Arg Lys Ala Leu Lys Asp Val Arg Tyr Lys Gly Tyr Asp Ile Pro
385                 390                 395                 400

Ser Gly Trp Lys Val Leu Pro Val Ile Ser Ala Val His Leu Asp Asn
                405                 410                 415

Ser Arg Tyr Asp Gln Pro Asn Leu Phe Asn Pro Trp Arg Trp Gln Gln
            420                 425                 430

Gln Asn Asn Gly Ala Ser Ser Gly Ser Gly Ser Phe Ser Thr Trp
        435                 440                 445

Gly Asn Asn Tyr Met Pro Phe Gly Gly Pro Arg Leu Cys Ala Gly
    450                 455                 460

Ser Glu Leu Ala Lys Leu Glu Met Ala Val Phe Ile His His Leu Val
465                 470                 475                 480

Leu Lys Phe Asn Trp Glu Leu Ala Glu Asp Gln Pro Phe Ala Phe
                485                 490                 495

Pro Phe Val Asp Phe Pro Asn Gly Leu Pro Ile Arg Val Ser Arg Ile
            500                 505                 510

Leu

<210> SEQ ID NO 3

```
<211> LENGTH: 24
<212> TYPE: DNA
<213> ORGANISM: Artificial Sequence
<220> FEATURE:
<223> OTHER INFORMATION: Primer: D4OVERF

<400> SEQUENCE: 3
atgttcgaaa cagagcatca tact                                          24

<210> SEQ ID NO 4
<211> LENGTH: 21
<212> TYPE: DNA
<213> ORGANISM: Artificial Sequence
<220> FEATURE:
<223> OTHER INFORMATION: Primer: D4PRM

<400> SEQUENCE: 4
cctcgatcaa agagagagag a                                             21

<210> SEQ ID NO 5
<211> LENGTH: 29
<212> TYPE: DNA
<213> ORGANISM: Artificial Sequence
<220> FEATURE:
<223> OTHER INFORMATION: Primer: D4RTF

<400> SEQUENCE: 5
ttcttggtga aaccatcggt tatcttaaa                                     29

<210> SEQ ID NO 6
<211> LENGTH: 26
<212> TYPE: DNA
<213> ORGANISM: Artificial Sequence
<220> FEATURE:
<223> OTHER INFORMATION: Primer: D4RTR

<400> SEQUENCE: 6
tatgataagc agttcctggt agattt                                        26

<210> SEQ ID NO 7
<211> LENGTH: 21
<212> TYPE: DNA
<213> ORGANISM: Artificial Sequence
<220> FEATURE:
<223> OTHER INFORMATION: Primer: D4F1

<400> SEQUENCE: 7
cgaggcaaca aaagtaatga a                                             21

<210> SEQ ID NO 8
<211> LENGTH: 21
<212> TYPE: DNA
<213> ORGANISM: Artificial Sequence
<220> FEATURE:
<223> OTHER INFORMATION: Primer: D4R1

<400> SEQUENCE: 8
gttagaaact ctaaagattc a                                             21

<210> SEQ ID NO 9
<211> LENGTH: 23
<212> TYPE: DNA
<213> ORGANISM: Artificial Sequence
<220> FEATURE:
<223> OTHER INFORMATION: Primer: D4F2

<400> SEQUENCE: 9
```
gattcttggc aacaaaactc tat                    23

<210> SEQ ID NO 10
<211> LENGTH: 20
<212> TYPE: DNA
<213> ORGANISM: Artificial Sequence
<220> FEATURE:
<223> OTHER INFORMATION: Primer: D4R2

<400> SEQUENCE: 10
ccgaacatct ttgagtgctt                        20

<210> SEQ ID NO 11
<211> LENGTH: 26
<212> TYPE: DNA
<213> ORGANISM: Artificial Sequence
<220> FEATURE:
<223> OTHER INFORMATION: Primer: D4F3

<400> SEQUENCE: 11
gtgtgaaggt tataaatgaa actctt                 26

<210> SEQ ID NO 12
<211> LENGTH: 24
<212> TYPE: DNA
<213> ORGANISM: Artificial Sequence
<220> FEATURE:
<223> OTHER INFORMATION: Primer: D4R3

<400> SEQUENCE: 12
ggtttaatag tgtcgacact aata                   24

<210> SEQ ID NO 13
<211> LENGTH: 22
<212> TYPE: DNA
<213> ORGANISM: Artificial Sequence
<220> FEATURE:
<223> OTHER INFORMATION: Primer: D4F4

<400> SEQUENCE: 13
ccgatgactt gtacgtgcgt ta                     22

<210> SEQ ID NO 14
<211> LENGTH: 24
<212> TYPE: DNA
<213> ORGANISM: Artificial Sequence
<220> FEATURE:
<223> OTHER INFORMATION: Primer: D4F5

<400> SEQUENCE: 14
gcgaagcata taatgagtat ggat                   24

<210> SEQ ID NO 15
<211> LENGTH: 26
<212> TYPE: DNA
<213> ORGANISM: Artificial Sequence
<220> FEATURE:
<223> OTHER INFORMATION: Primer: D4R5

<400> SEQUENCE: 15
gttggtcata acgagaatta tccaaa                 26

<210> SEQ ID NO 16
<211> LENGTH: 29
<212> TYPE: DNA
<213> ORGANISM: Artificial Sequence
<220> FEATURE:

<223> OTHER INFORMATION: Primer: D4XLINIT

<400> SEQUENCE: 16
taggatccag ctagtttctc tctctctct         29

<210> SEQ ID NO 17
<211> LENGTH: 20
<212> TYPE: DNA
<213> ORGANISM: Artificial Sequence
<220> FEATURE:
<223> OTHER INFORMATION: Primer: T7

<400> SEQUENCE: 17
taatacgact cactataggg         20

<210> SEQ ID NO 18
<211> LENGTH: 32
<212> TYPE: DNA
<213> ORGANISM: Artificial Sequence
<220> FEATURE:
<223> OTHER INFORMATION: Primer: D4OVERFA

<400> SEQUENCE: 18
gaattctaga atgttcgaaa cagagcatca ta         32

<210> SEQ ID NO 19
<211> LENGTH: 472
<212> TYPE: PRT
<213> ORGANISM: Arabidopsis thaliana

<400> SEQUENCE: 19

```
Met Ala Phe Thr Ala Phe Leu Leu Leu Ser Ser Ile Ala Ala Gly
  1               5                  10                  15

Phe Leu Leu Leu Arg Arg Thr Arg Tyr Arg Arg Met Gly Leu Pro
                 20                  25                  30

Pro Gly Ser Leu Gly Leu Pro Leu Ile Gly Glu Thr Phe Gln Leu Ile
             35                  40                  45

Gly Ala Tyr Lys Thr Glu Asn Pro Glu Pro Phe Ile Asp Glu Arg Val
         50                  55                  60

Ala Arg Tyr Gly Ser Val Phe Met Thr His Leu Phe Gly Glu Pro Thr
 65                  70                  75                  80

Ile Phe Ser Ala Asp Pro Glu Thr Asn Arg Phe Val Leu Gln Asn Glu
                 85                  90                  95

Gly Lys Leu Phe Glu Cys Ser Tyr Pro Ala Ser Ile Cys Asn Leu Leu
            100                 105                 110

Gly Lys His Ser Leu Leu Leu Met Lys Gly Ser Leu His Lys Arg Met
            115                 120                 125

His Ser Leu Thr Met Ser Phe Ala Asn Ser Ser Ile Ile Lys Asp His
        130                 135                 140

Leu Met Leu Asp Ile Asp Arg Leu Val Arg Phe Asn Leu Asp Ser Trp
145                 150                 155                 160

Ser Ser Arg Val Leu Leu Met Glu Glu Ala Lys Lys Ile Thr Phe Glu
                165                 170                 175

Leu Thr Val Lys Gln Leu Met Ser Phe Asp Pro Gly Glu Trp Ser Glu
            180                 185                 190

Ser Leu Arg Lys Glu Tyr Leu Leu Val Ile Glu Gly Phe Phe Ser Leu
        195                 200                 205

Pro Leu Pro Leu Phe Ser Thr Thr Tyr Arg Lys Ala Ile Gln Ala Arg
    210                 215                 220
```

Arg Lys Val Ala Glu Ala Leu Thr Val Val Met Lys Arg Arg Glu
225                 230                 235                 240

Glu Glu Glu Glu Gly Ala Glu Arg Lys Lys Asp Met Leu Ala Ala Leu
            245                 250                 255

Leu Ala Ala Asp Asp Gly Phe Ser Asp Glu Glu Ile Val Asp Phe Leu
        260                 265                 270

Val Ala Leu Leu Val Ala Gly Tyr Glu Thr Thr Ser Thr Ile Met Thr
        275                 280                 285

Leu Ala Val Lys Phe Leu Thr Glu Thr Pro Leu Ala Leu Ala Gln Leu
        290                 295                 300

Lys Glu Glu His Glu Lys Ile Arg Ala Met Lys Ser Asp Ser Tyr Ser
305                 310                 315                 320

Leu Glu Trp Ser Asp Tyr Lys Ser Met Pro Phe Thr Gln Cys Val Val
            325                 330                 335

Asn Glu Thr Leu Arg Val Ala Asn Ile Ile Gly Gly Val Phe Arg Arg
            340                 345                 350

Ala Met Thr Asp Val Glu Ile Lys Gly Tyr Lys Ile Pro Lys Gly Trp
            355                 360                 365

Lys Val Phe Ser Ser Phe Arg Ala Val His Leu Asp Pro Asn His Phe
370                 375                 380

Lys Asp Ala Arg Thr Phe Asn Pro Trp Arg Trp Gln Ser Asn Ser Val
385                 390                 395                 400

Thr Thr Gly Pro Ser Asn Val Phe Thr Pro Phe Gly Gly Gly Pro Arg
            405                 410                 415

Leu Cys Pro Gly Tyr Glu Leu Ala Arg Val Ala Leu Ser Val Phe Leu
            420                 425                 430

His Arg Leu Val Thr Gly Phe Ser Trp Val Pro Ala Glu Gln Asp Lys
            435                 440                 445

Leu Val Phe Phe Pro Thr Thr Arg Thr Gln Lys Arg Tyr Pro Ile Phe
        450                 455                 460

Val Lys Arg Arg Asp Phe Ala Thr
465                 470

<210> SEQ ID NO 20
<211> LENGTH: 464
<212> TYPE: PRT
<213> ORGANISM: Lycopersicon esculentum

<400> SEQUENCE: 20

Met Ala Phe Phe Leu Ile Phe Leu Ser Ser Phe Phe Gly Leu Cys Ile
1               5                   10                  15

Phe Cys Thr Ala Leu Leu Arg Trp Asn Gln Val Lys Tyr Asn Gln Lys
            20                  25                  30

Asn Leu Pro Pro Gly Thr Met Gly Trp Pro Leu Phe Gly Glu Thr Thr
        35                  40                  45

Glu Phe Leu Lys Leu Gly Pro Ser Phe Met Lys Asn Gln Arg Ala Arg
    50                  55                  60

Tyr Gly Ser Phe Phe Lys Ser His Ile Leu Gly Cys Pro Thr Ile Val
65                  70                  75                  80

Ser Met Asp Ser Glu Leu Asn Arg Tyr Ile Leu Val Asn Glu Ala Lys
                85                  90                  95

Gly Leu Val Pro Gly Tyr Pro Gln Ser Met Ile Asp Ile Leu Gly Lys
            100                 105                 110

Cys Asn Ile Ala Ala Val Asn Gly Ser Ala His Lys Tyr Met Arg Gly
        115                 120                 125

```
Ala Leu Leu Ser Leu Ile Ser Pro Thr Met Ile Arg Asp Gln Leu Leu
        130                 135                 140

Pro Lys Ile Asp Glu Phe Met Arg Ser His Leu Thr Asn Trp Asp Asn
145                 150                 155                 160

Lys Val Ile Asp Ile Gln Glu Lys Thr Asn Lys Met Ala Phe Leu Ser
                165                 170                 175

Ser Leu Lys Gln Ile Ala Gly Ile Glu Ser Thr Ser Leu Ala Gln Glu
            180                 185                 190

Phe Met Ser Glu Phe Phe Asn Leu Val Leu Gly Thr Leu Ser Leu Pro
        195                 200                 205

Ile Asn Leu Pro Asn Thr Asn Tyr His Arg Gly Phe Gln Ala Arg Lys
    210                 215                 220

Ile Ile Val Asn Leu Leu Arg Thr Leu Ile Glu Glu Arg Arg Ala Ser
225                 230                 235                 240

Lys Glu Ile Gln His Asp Met Leu Gly Tyr Leu Met Asn Glu Glu Ala
                245                 250                 255

Thr Arg Phe Lys Leu Thr Asp Asp Glu Met Ile Asp Leu Ile Ile Thr
            260                 265                 270

Ile Leu Tyr Ser Gly Tyr Glu Thr Val Ser Thr Thr Ser Met Met Ala
        275                 280                 285

Val Lys Tyr Leu His Asp His Pro Lys Val Leu Glu Glu Leu Arg Lys
    290                 295                 300

Glu His Met Ala Ile Arg Glu Lys Lys Lys Pro Glu Asp Pro Ile Asp
305                 310                 315                 320

Tyr Asn Asp Tyr Arg Ser Met Arg Phe Thr Arg Ala Val Ile Leu Glu
                325                 330                 335

Thr Ser Arg Leu Ala Thr Ile Val Asn Gly Val Leu Arg Lys Thr Thr
            340                 345                 350

Gln Asp Met Glu Ile Asn Gly Tyr Ile Ile Pro Lys Gly Trp Arg Ile
        355                 360                 365

Tyr Val Tyr Thr Arg Glu Leu Asn Tyr Asp Pro Arg Leu Tyr Pro Asp
    370                 375                 380

Pro Tyr Ser Phe Asn Pro Trp Arg Trp Met Asp Lys Ser Leu Glu His
385                 390                 395                 400

Gln Asn Ser Phe Leu Val Phe Gly Gly Gly Thr Arg Gln Cys Pro Gly
                405                 410                 415

Lys Glu Leu Gly Val Ala Glu Ile Ser Thr Phe Leu His Tyr Phe Val
            420                 425                 430

Thr Lys Tyr Arg Trp Glu Glu Ile Gly Gly Asp Lys Leu Met Lys Phe
        435                 440                 445

Pro Arg Val Glu Ala Pro Asn Gly Leu Arg Ile Arg Val Ser Ala His
450                 455                 460

<210> SEQ ID NO 21
<211> LENGTH: 444
<212> TYPE: PRT
<213> ORGANISM: Synechocystis sp.

<400> SEQUENCE: 21

Met Ile Thr Ser Pro Thr Asn Leu Asn Ser Leu Pro Ile Pro Pro Gly
1               5                   10                  15

Asp Phe Gly Leu Pro Trp Leu Gly Glu Thr Leu Asn Phe Leu Asn Asp
            20                  25                  30

Gly Asp Phe Gly Lys Lys Arg Gln Gln Gln Phe Gly Pro Ile Phe Lys
        35                  40                  45
```

-continued

Thr Arg Leu Phe Gly Lys Asn Val Ile Phe Ile Ser Gly Ala Leu Ala
 50                  55                  60

Asn Arg Phe Leu Phe Thr Lys Glu Gln Glu Thr Phe Gln Ala Thr Trp
 65                  70                  75                  80

Pro Leu Ser Thr Arg Ile Leu Leu Gly Pro Asn Ala Leu Ala Thr Gln
                 85                  90                  95

Met Gly Glu Ile His Arg Ser Arg Arg Lys Ile Leu Tyr Gln Ala Phe
            100                 105                 110

Leu Pro Arg Thr Leu Asp Ser Tyr Leu Pro Lys Met Asp Gly Ile Val
        115                 120                 125

Gln Gly Tyr Leu Glu Gln Trp Gly Lys Ala Asn Glu Val Ile Trp Tyr
130                 135                 140

Pro Gln Leu Arg Arg Met Thr Phe Asp Val Ala Ala Thr Leu Phe Met
145                 150                 155                 160

Gly Glu Lys Val Ser Gln Asn Pro Gln Leu Phe Pro Trp Phe Glu Thr
                165                 170                 175

Tyr Ile Gln Gly Leu Phe Ser Leu Pro Ile Pro Leu Pro Asn Thr Leu
            180                 185                 190

Phe Gly Lys Ser Gln Arg Ala Arg Ala Leu Leu Leu Ala Glu Leu Glu
        195                 200                 205

Lys Ile Ile Lys Ala Arg Gln Gln Gln Pro Pro Ser Glu Glu Asp Ala
210                 215                 220

Leu Gly Ile Leu Leu Ala Ala Arg Asp Asp Asn Asn Gln Pro Leu Ser
225                 230                 235                 240

Leu Pro Glu Leu Lys Asp Gln Ile Leu Leu Leu Phe Ala Gly His
                245                 250                 255

Glu Thr Leu Thr Ser Ala Leu Ser Ser Phe Cys Leu Leu Gly Gln
            260                 265                 270

His Ser Asp Ile Arg Glu Arg Val Arg Gln Glu Gln Asn Lys Leu Gln
        275                 280                 285

Leu Ser Gln Glu Leu Thr Ala Glu Thr Leu Lys Lys Met Pro Tyr Leu
290                 295                 300

Asp Gln Val Leu Gln Glu Val Leu Arg Leu Ile Pro Pro Val Gly Gly
305                 310                 315                 320

Gly Phe Arg Glu Leu Ile Gln Asp Cys Gln Phe Gln Gly Phe His Phe
                325                 330                 335

Pro Lys Gly Trp Leu Val Ser Tyr Gln Ile Ser Gln Thr His Ala Asp
            340                 345                 350

Pro Asp Leu Tyr Pro Asp Pro Glu Lys Phe Asp Pro Glu Arg Phe Thr
        355                 360                 365

Pro Asp Gly Ser Ala Thr His Asn Pro Pro Phe Ala His Val Pro Phe
370                 375                 380

Gly Gly Gly Leu Arg Glu Cys Leu Gly Lys Glu Phe Ala Arg Leu Glu
385                 390                 395                 400

Met Lys Leu Phe Ala Thr Arg Leu Ile Gln Gln Phe Asp Trp Thr Leu
                405                 410                 415

Leu Pro Gly Gln Asn Leu Glu Leu Val Val Thr Pro Ser Pro Arg Pro
            420                 425                 430

Lys Asp Asn Leu Arg Val Lys Leu His Ser Leu Met
        435                 440

<210> SEQ ID NO 22
<211> LENGTH: 519
<212> TYPE: PRT
<213> ORGANISM: Zea mays

<400> SEQUENCE: 22

```
Met Leu Gly Val Gly Met Ala Ala Val Leu Leu Gly Ala Val Ala
 1               5                  10                  15
Leu Leu Leu Ala Asp Ala Ala Arg Arg Ala His Trp Trp Tyr Arg
                20                  25                  30
Glu Ala Ala Glu Ala Val Leu Val Gly Ala Val Ala Leu Val Val Val
                35                  40                  45
Asp Ala Ala Arg Arg Ala His Gly Trp Tyr Arg Glu Ala Ala Leu
        50                  55                  60
Gly Ala Ala Arg Arg Ala Arg Leu Pro Pro Gly Glu Met Gly Trp Pro
 65                 70                  75                  80
Leu Val Gly Gly Met Trp Ala Phe Leu Arg Ala Phe Lys Ser Gly Lys
                    85                  90                  95
Pro Asp Ala Phe Ile Ala Ser Phe Val Arg Arg Phe Gly Arg Thr Gly
               100                 105                 110
Val Tyr Arg Ser Phe Met Phe Ser Ser Pro Thr Val Leu Val Thr Thr
           115                 120                 125
Ala Glu Gly Cys Lys Gln Val Leu Met Asp Asp Ala Phe Val Thr
       130                 135                 140
Gly Trp Pro Lys Ala Thr Val Ala Leu Val Gly Pro Arg Ser Phe Val
145                 150                 155                 160
Ala Met Pro Tyr Asp Glu His Arg Arg Ile Arg Lys Leu Thr Ala Ala
                165                 170                 175
Pro Ile Asn Gly Phe Asp Ala Leu Thr Gly Tyr Leu Pro Phe Ile Asp
                180                 185                 190
Arg Thr Val Thr Ser Ser Leu Arg Ala Trp Ala Asp His Gly Gly Ser
            195                 200                 205
Val Glu Phe Leu Thr Glu Leu Arg Arg Met Thr Phe Lys Ile Ile Val
        210                 215                 220
Gln Ile Phe Leu Gly Gly Ala Asp Gln Ala Thr Thr Arg Ala Leu Glu
225                 230                 235                 240
Arg Ser Tyr Thr Glu Leu Asn Tyr Gly Met Arg Ala Met Ala Ile Asn
                245                 250                 255
Leu Pro Gly Phe Ala Tyr Arg Gly Ala Leu Arg Ala Arg Arg Leu
                260                 265                 270
Val Ala Val Leu Gln Gly Val Leu Asp Glu Arg Arg Ala Ala Arg Ala
            275                 280                 285
Lys Gly Val Ser Gly Gly Val Asp Met Met Asp Arg Leu Ile Glu
290                 295                 300
Ala Gln Asp Glu Arg Gly Arg His Leu Asp Asp Glu Ile Ile Asp
305                 310                 315                 320
Val Leu Val Met Tyr Leu Asn Ala Gly His Glu Ser Ser Gly His Ile
                325                 330                 335
Thr Met Trp Ala Thr Val Phe Leu Gln Glu Asn Pro Asp Met Phe Ala
            340                 345                 350
Arg Ala Lys Ala Glu Gln Glu Ala Ile Met Arg Ser Ile Pro Ser Ser
        355                 360                 365
Gln Arg Gly Leu Thr Leu Arg Asp Phe Arg Lys Met Glu Tyr Leu Ser
    370                 375                 380
Gln Val Ile Asp Glu Thr Leu Arg Leu Val Asn Ile Ser Phe Val Ser
385                 390                 395                 400
Phe Arg Gln Ala Thr Arg Asp Val Phe Val Asn Gly Tyr Leu Ile Pro
                405                 410                 415
```

```
Lys Gly Trp Lys Val Gln Leu Trp Tyr Arg Ser Val His Met Asp Pro
            420                 425                 430

Gln Val Tyr Pro Asp Pro Thr Lys Phe Asp Pro Ser Arg Trp Glu Gly
            435                 440                 445

His Ser Pro Arg Ala Gly Thr Phe Leu Ala Phe Gly Leu Gly Ala Arg
        450                 455                 460

Leu Cys Pro Gly Asn Asp Leu Ala Lys Leu Glu Ile Ser Val Phe Leu
465                 470                 475                 480

His His Phe Leu Leu Gly Tyr Lys Leu Ala Arg Thr Asn Pro Arg Cys
                485                 490                 495

Arg Val Arg Tyr Leu Pro His Pro Arg Pro Val Asp Asn Cys Leu Ala
                500                 505                 510

Lys Ile Thr Arg Val Gly Ser
            515

<210> SEQ ID NO 23
<211> LENGTH: 492
<212> TYPE: PRT
<213> ORGANISM: Danio rerio

<400> SEQUENCE: 23

Met Gly Leu Tyr Thr Leu Met Val Thr Phe Leu Cys Thr Ile Val Leu
  1               5                  10                  15

Pro Val Leu Leu Phe Leu Ala Ala Val Lys Leu Trp Glu Met Leu Met
             20                  25                  30

Ile Arg Arg Val Asp Pro Asn Cys Arg Ser Pro Leu Pro Pro Gly Thr
         35                  40                  45

Met Gly Leu Pro Phe Ile Gly Glu Thr Leu Gln Leu Ile Leu Gln Arg
     50                  55                  60

Arg Lys Phe Leu Arg Met Lys Arg Gln Lys Tyr Gly Cys Ile Tyr Lys
 65                  70                  75                  80

Thr His Leu Phe Gly Asn Pro Thr Val Arg Val Met Gly Ala Asp Asn
                 85                  90                  95

Val Arg Gln Ile Leu Leu Gly Glu His Lys Leu Val Ser Val Gln Trp
            100                 105                 110

Pro Ala Ser Val Arg Thr Ile Leu Gly Ser Asp Thr Leu Ser Asn Val
        115                 120                 125

His Gly Val Gln His Lys Asn Lys Lys Ala Ile Met Arg Ala Phe
    130                 135                 140

Ser Arg Asp Ala Leu Glu His Tyr Ile Pro Val Ile Gln Gln Glu Val
145                 150                 155                 160

Lys Ser Ala Ile Gln Glu Trp Leu Gln Lys Asp Ser Cys Val Leu Val
                165                 170                 175

Tyr Pro Glu Met Lys Lys Leu Met Phe Arg Ile Ala Met Arg Ile Leu
            180                 185                 190

Leu Gly Phe Glu Pro Glu Gln Ile Lys Thr Asp Glu Gln Glu Leu Val
        195                 200                 205

Glu Ala Phe Glu Glu Met Ile Lys Asn Leu Phe Ser Leu Pro Ile Asp
    210                 215                 220

Val Pro Phe Ser Gly Leu Tyr Arg Gly Leu Arg Ala Arg Asn Phe Ile
225                 230                 235                 240

His Ser Lys Ile Glu Glu Asn Ile Arg Lys Lys Ile Gln Asp Asp Asp
                245                 250                 255

Asn Glu Asn Glu Gln Lys Tyr Lys Asp Ala Leu Gln Leu Leu Ile Glu
            260                 265                 270
```

```
Asn Ser Arg Arg Ser Asp Glu Pro Phe Ser Leu Gln Ala Met Lys Glu
            275                 280                 285

Ala Ala Thr Glu Leu Leu Phe Gly Gly His Glu Thr Thr Ala Ser Thr
290                 295                 300

Ala Thr Ser Leu Val Met Phe Leu Gly Leu Asn Thr Glu Val Val Gln
305                 310                 315                 320

Lys Val Arg Glu Val Gln Glu Lys Val Glu Met Gly Met Tyr Thr
                325                 330                 335

Pro Gly Lys Gly Leu Ser Met Glu Leu Leu Asp Gln Leu Lys Tyr Thr
                340                 345                 350

Gly Cys Val Ile Lys Glu Thr Leu Arg Ile Asn Pro Val Pro Gly
            355                 360                 365

Gly Phe Arg Val Ala Leu Lys Thr Phe Glu Leu Asn Gly Tyr Gln Ile
            370                 375                 380

Pro Lys Gly Trp Asn Val Ile Tyr Ser Ile Cys Asp Thr His Asp Val
385                 390                 395                 400

Ala Asp Val Phe Pro Asn Lys Glu Glu Phe Gln Pro Glu Arg Phe Met
                405                 410                 415

Ser Lys Gly Leu Glu Asp Gly Ser Arg Phe Asn Tyr Ile Pro Phe Gly
                420                 425                 430

Gly Gly Ser Arg Met Cys Val Gly Lys Glu Phe Ala Lys Val Leu Leu
            435                 440                 445

Lys Ile Phe Leu Val Glu Leu Thr Gln His Cys Asn Trp Ile Leu Ser
450                 455                 460

Asn Gly Pro Pro Thr Met Lys Thr Gly Pro Thr Ile Tyr Pro Val Asp
465                 470                 475                 480

Asn Leu Pro Thr Lys Phe Thr Ser Tyr Val Arg Asn
                485                 490

<210> SEQ ID NO 24
<211> LENGTH: 504
<212> TYPE: PRT
<213> ORGANISM: Homo sapiens

<400> SEQUENCE: 24

Met Ala Leu Ile Pro Asp Leu Ala Met Glu Thr Trp Leu Leu Leu Ala
1               5                   10                  15

Val Ser Leu Val Leu Leu Tyr Leu Tyr Gly Thr His Ser His Gly Leu
                20                  25                  30

Phe Lys Lys Leu Gly Ile Pro Gly Pro Thr Pro Leu Pro Phe Leu Gly
            35                  40                  45

Asn Ile Leu Ser Tyr His Lys Gly Phe Cys Met Phe Asp Met Glu Cys
        50                  55                  60

His Lys Lys Tyr Gly Lys Val Trp Gly Phe Tyr Asp Gly Gln Gln Pro
65                  70                  75                  80

Val Leu Ala Ile Thr Asp Pro Asp Met Ile Lys Leu Val Leu Val Lys
                85                  90                  95

Glu Cys Tyr Ser Val Phe Thr Asn Arg Glu Pro Phe Gly Pro Val Gly
            100                 105                 110

Phe Met Lys Ser Ala Ile Ser Ile Ala Glu Asp Glu Glu Trp Lys Arg
        115                 120                 125

Leu Arg Ser Leu Leu Ser Pro Thr Phe Thr Ser Gly Lys Leu Lys Glu
    130                 135                 140

Met Val Pro Ile Ile Ala Gln Tyr Gly Asp Val Leu Val Arg Asn Leu
145                 150                 155                 160
```

```
Arg Arg Glu Arg Glu Thr Gly Lys Pro Val Thr Leu Lys Asp Val Phe
                165                 170                 175

Gly Ala Tyr Ser Met Asp Val Ile Thr Ser Ser Phe Gly Val Asn
            180                 185                 190

Val Asp Ser Leu Asn Asn Pro Gln Asp Pro Leu Val Glu Asn Thr Lys
        195                 200                 205

Lys Leu Leu Arg Phe Asp Phe Leu Asp Pro Phe Leu Ser Ile Thr
    210                 215                 220

Val Phe Pro Phe Leu Ile Pro Ile Leu Glu Val Leu Asn Ile Cys Val
225                 230                 235                 240

Phe Pro Arg Glu Val Thr Asn Phe Leu Arg Lys Ala Val Lys Arg Met
                245                 250                 255

Lys Glu Ser Arg Leu Glu Asp Thr Gln Lys His Arg Val Asp Phe Leu
                260                 265                 270

Gln Leu Met Ile Asp Ser His Lys Asn Ser Lys Glu Thr Glu Ser His
            275                 280                 285

Lys Ala Leu Ser Asp Leu Glu Leu Val Ala Gln Ser Ile Ile Phe Ile
        290                 295                 300

Phe Ala Gly Tyr Glu Thr Thr Ser Ser Val Leu Ser Phe Ile Met Tyr
305                 310                 315                 320

Glu Leu Ala Thr His Pro Asp Val Gln Gln Lys Leu Gln Glu Glu Ile
                325                 330                 335

Asp Ala Val Leu Pro Asn Lys Ala Pro Pro Thr Tyr Asp Thr Val Leu
                340                 345                 350

Gln Met Glu Tyr Leu Asp Met Val Val Asn Glu Thr Leu Arg Leu Phe
            355                 360                 365

Pro Ile Ala Met Arg Leu Glu Arg Val Cys Lys Lys Asp Val Glu Ile
        370                 375                 380

Asn Gly Met Phe Ile Pro Lys Gly Trp Val Val Met Ile Pro Ser Tyr
385                 390                 395                 400

Ala Leu His Arg Asp Pro Lys Tyr Trp Thr Glu Pro Glu Lys Phe Leu
                405                 410                 415

Pro Glu Arg Phe Ser Lys Lys Asn Lys Asp Asn Ile Asp Pro Tyr Ile
                420                 425                 430

Tyr Thr Pro Phe Gly Ser Gly Pro Arg Asn Cys Ile Gly Met Arg Phe
            435                 440                 445

Ala Leu Met Asn Met Lys Leu Ala Leu Ile Arg Val Leu Gln Asn Phe
        450                 455                 460

Ser Phe Lys Pro Cys Lys Glu Thr Gln Ile Pro Leu Lys Leu Ser Leu
465                 470                 475                 480

Gly Gly Leu Leu Gln Pro Glu Lys Pro Val Val Leu Lys Val Glu Ser
                485                 490                 495

Arg Asp Gly Thr Val Ser Gly Ala
            500

<210> SEQ ID NO 25
<211> LENGTH: 575
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (1)...(575)
<223> OTHER INFORMATION: Xaa = Any Amino Acid or No Amino Acid

<400> SEQUENCE: 25
```

```
Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Leu Leu Ser Xaa Xaa Ala Leu Xaa Val Xaa
         35                  40                  45

Leu Xaa Leu Ala Ala Arg Arg Xaa Xaa Xaa Arg Tyr Xaa Xaa Xaa Xaa
 50                  55                  60

Xaa Xaa Xaa Xaa Arg Arg Lys Xaa Leu Pro Pro Gly Thr Met Gly Leu
65                   70                  75                  80

Pro Xaa Leu Gly Glu Thr Leu Gln Phe Leu Lys Xaa Xaa Xaa Xaa Xaa
             85                  90                  95

Xaa Pro Gly Asp Phe Xaa Lys Glu Arg Val Xaa Xaa Tyr Gly Xaa Xaa
             100                 105                 110

Xaa Xaa Ile Tyr Lys His Leu Phe Gly Glu Pro Thr Ile Xaa Ser Xaa
         115                 120                 125

Asp Ala Glu Leu Asn Arg Phe Xaa Leu Xaa Asn Glu Gly Xaa Lys Leu
130                 135                 140

Phe Xaa Cys Xaa Xaa Pro Ala Ser Xaa Xaa Gly Xaa Leu Gly Lys Xaa
145                 150                 155                 160

Ser Leu Xaa Ala Xaa Xaa Gly Xaa Glu His Lys Arg Met Arg Xaa Leu
             165                 170                 175

Leu Xaa Ser Xaa Phe Ser Xaa Xaa Xaa Xaa Leu Asp His Xaa Leu Pro
         180                 185                 190

Xaa Ile Asp Arg Xaa Val Arg Ser Xaa Leu Xaa Xaa Trp Xaa Xaa Xaa
     195                 200                 205

Xaa Gln Lys Xaa Xaa Ile Val Xaa Xaa Xaa Glu Xaa L

```
                          420              425              430
Ile Val Gly Gly Xaa Phe Arg Xaa Ala Xaa Lys Asp Val Glu Ile Asn
            435              440              445

Gly Tyr Xaa Ile Pro Lys Gly Trp Lys Val Xaa Tyr Ser Ile Arg Ala
        450              455              460

Val His Leu Asp Pro Asp Xaa Tyr Pro Asp Pro Glu Lys Phe Asn Pro
465              470              475              480

Xaa Arg Trp Xaa Xaa Lys Xaa Xaa Xaa Ser Asn Ser Xaa Xaa Xaa
                485              490              495

Xaa Xaa Xaa Xaa Xaa Xaa Xaa Asn Xaa Xaa Pro Phe Gly Gly Gly Pro
            500              505              510

Arg Leu Cys Pro Gly Lys Glu Leu Ala Lys Leu Glu Met Xaa Val Phe
            515              520              525

Leu His Arg Leu Val Gln Xaa Phe Trp Glu Leu Ala Xaa Xaa Xaa Asp
        530              535              540

Xaa Xaa Xaa Lys Leu Val Xaa Phe Pro Thr Xaa Arg Pro Xaa Asp Asn
545              550              555              560

Leu Pro Ile Lys Val Xaa Xaa Arg Asp Xaa Xaa Xaa Xaa Xaa Xaa
                565              570              575

<210> SEQ ID NO 26
<211> LENGTH: 11
<212> TYPE: PRT
<213> ORGANISM: Artificial Sequence
<220> FEATURE:
<223> OTHER INFORMATION: Heme binding domain
<220> FEATURE:
<221> NAME/KEY: VARIANT
<222> LOCATION: 4
<223> OTHER INFORMATION: Xaa = Ala, Ser, or Val
<220> FEATURE:
<221> NAME/KEY: VARIANT
<222> LOCATION: 8
<223> OTHER INFORMATION: Xaa = Any Amino Acid
<220> FEATURE:
<221> NAME/KEY: VARIANT
<222> LOCATION: 10
<223> OTHER INFORMATION: Xaa = Pro, Ala, or Val

<400> SEQUENCE: 26

Pro Phe Gly Xaa Gly Arg Arg Xaa Cys Xaa Gly
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Heme binding domain

<400> SEQUENCE: 27

Pro Phe Gly Gly Phe Pro Arg Leu Cys Pro Gly Lys Glu Leu
1               5                   10

<210> SEQ ID NO 28
<211> LENGTH: 17
<212> TYPE: PRT
<213> ORGANISM: Artificial Sequence
<220> FEATURE:
<223> OTHER INFORMATION: Signature sequence
<220> FEATURE:
<221> NAME/KEY: VARIANT
<222> LOCATION: 1,13,15,16
<223> OTHER INFORMATION: Xaa = Any Amino Acid

<400> SEQUENCE: 28
```

```
Xaa Leu Leu Phe Ala Gly His Glu Thr Thr Ser Ser Xaa Ile Xaa Xaa
  1               5                  10                  15
Ala

<210> SEQ ID NO 29
<211> LENGTH: 11
<212> TYPE: PRT
<213> ORGANISM: Artificial Sequence
<220> FEATURE:
<223> OTHER INFORMATION: Exemplary sequence

<400> SEQUENCE: 29

Pro Phe Gly Gly Gly Pro Arg Leu Cys Ala Gly
  1               5                  10

<210> SEQ ID NO 30
<211> LENGTH: 6
<212> TYPE: PRT
<213> ORGANISM: Arabidopsis thaliana

<400> SEQUENCE: 30

Ala Gly His Glu Thr Ser
  1               5
```